United States Patent
Woods et al.

(10) Patent No.: US 9,428,732 B2
(45) Date of Patent: Aug. 30, 2016

(54) COMPOSITIONS AND METHODS FOR DIFFERENTIATING PLURIPOTENT STEM CELLS INTO PRIMITIVE BLOOD CELLS AND USES THEREOF

(71) Applicant: Primorigen Biosciences, Inc., Madison, WI (US)

(72) Inventors: Niels-Bjarne Woods, Furuland (SE); Roger Ronn, Lund (SE); Carolina Guibentif, Lund (SE)

(73) Assignee: Primorigen Biosciences, Inc., Madison, WI (US)

( * ) Notice: Subject to any disclaimer, the term of this patent is extended or adjusted under 35 U.S.C. 154(b) by 0 days.

(21) Appl. No.: 13/706,067

(22) Filed: Dec. 5, 2012

(65) Prior Publication Data

US 2013/0171110 A1 Jul. 4, 2013

Related U.S. Application Data

(60) Provisional application No. 61/566,940, filed on Dec. 5, 2011.

(51) Int. Cl.
| | |
|---|---|
| C12N 5/078 | (2010.01) |
| C12N 5/0783 | (2010.01) |
| C12N 5/0789 | (2010.01) |
| C12N 5/0781 | (2010.01) |
| A61K 35/14 | (2015.01) |

(52) U.S. Cl.
CPC ........... *C12N 5/0634* (2013.01); *C12N 5/0635* (2013.01); *C12N 5/0636* (2013.01); *C12N 5/0646* (2013.01); *C12N 5/0647* (2013.01); *A61K 35/14* (2013.01); *C12N 2500/24* (2013.01); *C12N 2500/38* (2013.01); *C12N 2501/02* (2013.01); *C12N 2501/04* (2013.01); *C12N 2501/065* (2013.01); *C12N 2501/125* (2013.01); *C12N 2501/14* (2013.01); *C12N 2501/145* (2013.01); *C12N 2501/15* (2013.01); *C12N 2501/155* (2013.01); *C12N 2501/165* (2013.01); *C12N 2501/2302* (2013.01); *C12N 2501/2307* (2013.01); *C12N 2501/2315* (2013.01); *C12N 2501/26* (2013.01); *C12N 2501/385* (2013.01); *C12N 2501/71* (2013.01); *C12N 2501/80* (2013.01); *C12N 2501/999* (2013.01); *C12N 2506/02* (2013.01); *C12N 2506/45* (2013.01)

(58) Field of Classification Search
CPC ........... A61K 35/12; A61K 2035/124; A61K 38/00; A61K 48/00; A61K 35/28; C12N 2310/121; C12N 15/113; C12N 2501/385; C12N 2510/00
USPC ................ 424/93.7; 435/366, 377
See application file for complete search history.

(56) References Cited

U.S. PATENT DOCUMENTS

| | | | |
|---|---|---|---|
| 7,790,458 B2 | 9/2010 | Xu et al. | |
| 8,093,049 B2 | 1/2012 | Tseng et al. | |
| 8,168,428 B2 | 5/2012 | Zon et al. | |
| 2009/0220461 A1 | 9/2009 | Suckow et al. | |
| 2009/0220462 A1 | 9/2009 | Chute | |
| 2009/0285786 A1* | 11/2009 | Zon et al. | 424/93.7 |
| 2010/0216181 A1 | 8/2010 | Daigh et al. | |
| 2010/0240132 A1* | 9/2010 | Lanza et al. | 435/455 |

FOREIGN PATENT DOCUMENTS

| | | |
|---|---|---|
| WO | WO 2007/033330 A2 | 3/2007 |
| WO | WO 2009/135206 A1 | 11/2009 |
| WO | WO 2010/138782 | * 12/2010 |

OTHER PUBLICATIONS

Houck KA et al. (1988). Norepinephrine modulates the growth-inhibitory effect of transforming growth factor-beta in primary rat hepatocyte cultures. Journal of Cellular Physiology, v135, p. 551-555.*
Theodosiou et al. (2010). From carrot to clinic: an overview of the retinoic acid signaling pathway. Cell Mol Life Sci, v67, p. 1423-1445.*
Tsonis et al. (2000). Role of Retinoic Acid in Lens Regeneration. Developmental Dynamics, v219, p. 588-593.*
Takamatsu et al. (2008). The first potent subtype-selective retinoid x receptor (RXR) agonist possessing a 3-isopropoxy-4-isopropylphenylamino moiety, NEt-3IP (RXRalpha/beta-dual agonist). ChemMedChem, v3(5), p. 780-787.*
Karadag et al. (2009). Review of Methods to Determine Antioxidant Capacities. Food Anal Methods, v2, p. 41-60.*
de Graff et al. (2008). Selective structure-based virtual screening for full and partial agonists of the beta2 adrenergic receptor. J Med Chem, v51, p. 4978-4985.*
Yong et al. (2009). The p38 MAPK inhibitors for the treatment of inflammatory diseases and cancer. Expert Opinion on Investigational Drugs, v18(2), p. 1893-1905.*
Clapier et al. (2009). The biology of chromatin remodeling complexes. Annu Rev Biochem, v78, p. 273-304.*
Gottlicher et al. (2001). Valproic acid defines a novel class of Hdac inhibitors inducing differentiation of transformed cells. EMBO J, v20(24), p. 6969-6978.*
Nakajima et al. (1995). FR901228, a potent antitumor antibiotic, is a novel histone deacetylase inhibitor. Exp Cell Res, v241(1), p. 126-133.*
Duvic et al (2007). Vorinostat: a new oral histone deacetylase inhibitor approved for cutaneous T-cell lymphoma. Expert Opin Investig Drugs, v16(7), p. 111-1120.*
Ghiani et al. (1999). Neurotransmitter receptor activation triggers p27Kip1 and p21CIP1 accumulation and G1 cell cycle arrest in oligodendrocyte progenitors. Development, v126, p. 1077-1090.*
Aiken et al. (2009). beta2-Adrenoreceptor ligands regulate osteoclast differentiation in vitro by direct and indirect mechanismsArchives of Biochemistry and Biophysics, v482, p. 96-102.*

(Continued)

*Primary Examiner* — Scott Long
*Assistant Examiner* — Sean C Barron
(74) *Attorney, Agent, or Firm* — Charles S. Sara, Esq.; Daniel A. Blasiole; DeWitt Ross & Stevens S.C.

(57) ABSTRACT

Compositions and methods that employ various combinations of such factors as retinoic acid signaling inhibitors, antioxidants, BMP4, VEGF, prostaglandin $E_2$ pathway stimulants, TPO, SCF, FLT-3, EPO, TGFβ1, p38 MAPK inhibitors, beta adrenergic receptor agonists, cell cycle inhibitors, RXR agonists, Cripto, and chromatin remodelers to drive differentiation of pluripotent stem cells towards primitive blood cells. Uses of such primitive blood cells are provided.

19 Claims, 23 Drawing Sheets

(56) References Cited

OTHER PUBLICATIONS

Aitken et al. (2009). b2-Adrenoreceptor ligands regulate osteoclast differentiation in vitro by direct and indirect mechanisms. Archives of Biochemistry and Biophysics, v482, p. 96-102.*
Ishitsuka et al. (2008). p38 mitogen-activated protein kinase inhibitor LY2228820 enhances bortezomib-induced cytotoxicity and inhibits osteoclastogenesis in multiple myeloma; therapeutic implications. Bone British Journal of Haematology, v141, p. 598-606.*
Graichen et al. (2008). Enhanced cardiomyogenesis of human embryonic stem cells by a small molecular inhibitor of p38 MAPK. Differentiation, v76, p. 357-37.*
Hayase et al. (1997). Osteoclast development from hematopoietic stem cells: Apparent divergence of the osteoclast lineage prior to macrophage commitment. Exp Hematol, v25(1), p. 19-25.*
Rocha et al. (2006). Clinical Use of Umbilical Cord Blood Hematopoietic Stem Cells. Biol Blood Marrow Transplant, v12(1 Suppl 1), p. 34-41.*
North et al. (2007). Prostaglandin E2 regulates vertebrate haematopoietic stem cell homeostasis. Nature, v447, p. 1007-1011.*
Xu et al. (2002). HDAC3 is crucial in shear- and VEGF-induced stem cell differentiation toward endothelial cells. Nature Biotechnology, v20, p. 1261-1264.*
Zeng et al. (2006). HDAC3 is crucial in shear- and VEGF-induced stem cell differentiation toward endothelial cells. JCB, 174(7), p. 1059-1069.*
Ledran et al. (2008). Efficient Hematopoietic Differentiation of Human Embryonic Stem Cells on Stromal Cells Derived from Hematopoietic Niches. Cell Stem Cell, v3, p. 85-98.*
Fehling et al. (2003). Tracking mesoderm induction and its specification to the hemangioblast during embryonic stem cell differentiation. Development, v130, p. 4217-4227.*
Aulehla et al., *Signaling gradients during paraxial mesoderm development*, Cold Spring Harb Perspect Biol. Feb. 2010; 2(2):a000869.
Bhatia et al., *Hematopoietic development from human embryonic stem cells*, Hematology/the Education Program of the American Society of Hematology 200'7; p. 11-6.
Bhatia et al., *Hematopoiesis from human embryonic stem cell*, Ann NY Acad Sci. Jun. 2007;1106:219-22. Epub Mar. 1, 2007.
Charoudeh et al., *Identification of an NK/T cell-restricted progenitor in adult bone marrow contributing to bone marrow-and thymic-dependent NK cells*, Blood 2010, 116(2):183-92.
Choi et al., *Identification of the hemogenic endothelial progenitor and its direct precursor in human pluripotent stem cell differentiation cultures*, Cell. Rep. 2012 Sep. 27, 201; 2(3):553-67.
Chute et al., *Inhibition of aldehyde dehydrogenase and retinoid signaling induces the expansion of human hematopoietic stem cells*, PNAS Aug. 1, 2006, vol. 103, No. 31, 11707-11712.
Deimling et al., *Retinoic acid regulates anterior-posterior patterning within the lateral plate mesoderm*, Mech Dev. 126 (2009) 913-23.
De Jong et al., *Interaction of retinoic acid and scl controls primitive blood development*, Blood Jul. 15, 2010; 116(2):201-9.
Duester et al., *Retinoic acid synthesis and signaling during early organogenesis*Cell. Sep. 19, 2008; 134(6):921-31. Doi:10.1016/j.cell.2008.09.002.
Ema et al., *Deletion of the selection cassette, but not cis-acting elements, in targeted Flk 1-lacZ allele reveals Flk1 expression in multipotent mesodermal progenitors*, Blood 2006, 107:111-1117.
Goldie et al., *Cell signaling directing the formation and function of hemogenic endothelium during murine embryogenesis*, Blood, 2008, 112:3194-3204.
Huang et al., *mSin3A Regulates Murine Erythroleukemia Cell Differentiation through Association with the TAL1 (or SCL) Transcription Factor*, Mol. Cell Biol., 2000, 20(6):2248-59.
Ishiguro et al., *Inhibition of all-trans retinoic acid-induced granulocytic differentiation of WEHI-3B $D^+$cells by forced expression of SCL (TAL1) and GATA-1*, Leuk. Res. Sep. 2009, 33(9): 1249-1254.
Ledran et al., *Efficient Hematopoietic Differentiation of Human Embryonic Stem Cells on Stromal Cells Derived from Hematopoietic Niches*, Stem Cell 3, 85-98, Jul. 2008.
Levi et al., *Aldehyde dehydrogenase 1a1 is dispensable for stem cell function in the mouse hematopoietic and nervous systems*, Blood 2009; 113:1670-1680.
Ma et al., *A DEAB-sensitive aldehyde dehydrogenase regulations hematopoietic stem and progenitor cells development during primitive hematopoiesis in zebrafish embryos*, Leukemia 2010; 24:2090-2099.
Muramoto et al., *Inhibition of Aldehyde Dehydrogenase Expands Hematopoietic Stem Cells with Radioprotective Capacity*, Stem Cells, 2010;28: 523-534.
Murphey et al., *A chemical genetic screen for cell cycle inhibitors in zebrafish embryos*, Chem Biol Drug Des., 2006 68:213-219.
Purton et al., *All-trans retinoic acid enhances the long-term repopulating activity of cultured hematopoietic stem cells*, Blood, vol. 95, No. 2, pp. 470-477, 2000.
Safi et al., *Pharmacological Manipulation of the RAR/RXR Signaling Pathway Maintains the Repopulating Capacity of Hematopoietic Stem Cells in Culture*, Mol Endocrinol, Feb. 2009, 23(2):188-201.
Szatmari et al., *The retinoid signaling pathway inhibits hematopoiesis and uncouples from the hox genes during hematopoietic development*, Stem Cells 2010; 28(9): 1518-1539.
Tian et al., *Bioluminescent Imaging Demonstrates that Transplanted Human Embryonic Stem Cell-Derived $CD34^+$Cells Preferentially Develop into Endothelial Cells*, Stem Cells 2009;27:2675-2685.
Wang et al., *Generation of hematopoietic repopulating cells from human embryonic stem cells independent of ectopic HOXB4 expression*, JEM, vol. 201, No. 10, May 16, 2005 1603-1614.
Woods et al., *Brief Report: Efficient Generatin of Hematopoietic Precursers and Progenitors from Human Pluripotent Stem Cell Lines*, Stem Cells 2011; 29:1158-1163.
Yu et al., *Retinoic acid enhances the generation of hematopoietic progenitors from human embryonic stem cell—derived hematovascular precursors*, Blood 2010; 116: 4786-4794.
Yahata et al., *Accumulation of oxidative DNA damage restricts the self-renewal capacity of human hematopoietic stem cells*, Blood Sep. 15, 2011; 118(11):2941-50.
Zhang et al., *SCL expression at critical points in human hematopoietic lineage commitment*, Stem Cells Jun.-Jul. 2005;23(6):852-60.
Zhang et al., *Short-term BMP-4 treatment initiates mesoderm induction in human embryonic stem cells*, Blood, 2008 111:1933-1941.

* cited by examiner

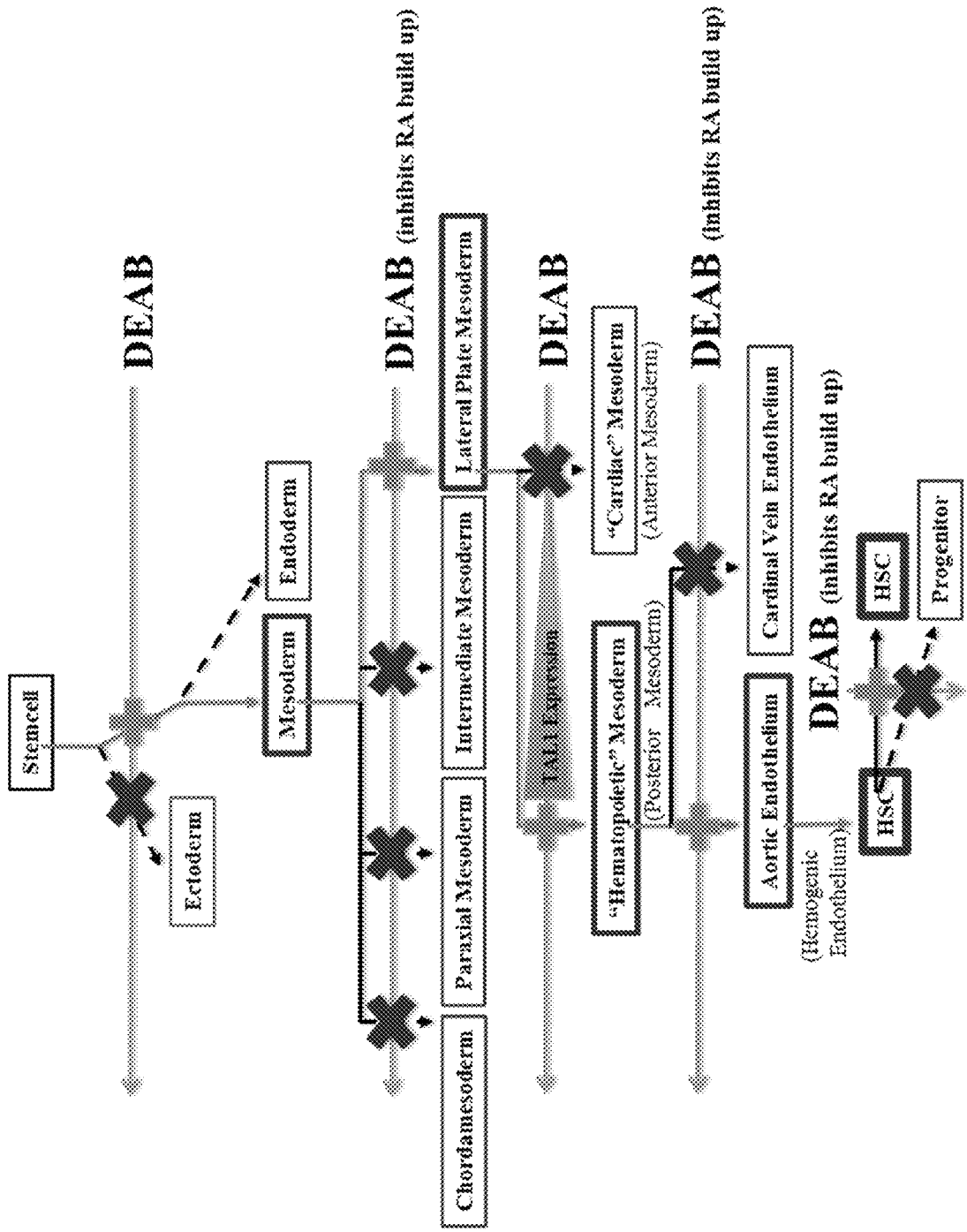

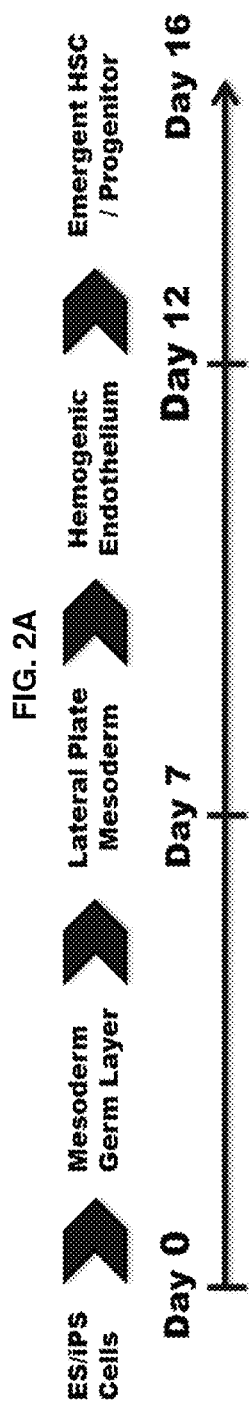

| Method Day | Method Step | Effect of Method Step |
|---|---|---|
| 0 | Generate large, dense, pluripotent stem cell colonies with brownish hue | Ensures high survival of EBs during initial exposure to differentiation medium |
| 1 | Replace half of medium with differentiation medium | EB survival and transition to differentiation medium; EB mesoderm biasing begins |
| 2 | Replace all of medium with differentiation medium | EB mesoderm biasing |
| 4,6 | Replace half of existing differentiation medium with fresh differentiation medium | Removes toxic byproducts and replenish nutrients |
| 8 | Replace half of existing differentiation medium with fresh differentiation medium and plate EBs | Removes toxic byproducts/dead cells and replenishes nutrients; plates properly biased EBs to facilitate generation of hemogenic endothelium-like layer |
| 10,12,14 | Add fresh differentiation medium to existing differentiation medium (day 10) add 1ml fresh to 2ml existing) & (day 12, add 1ml fresh to 3ml existing) & (day 14 add 1ml fresh to 4ml existing) | Dilutes byproducts and replenishes nutrients; continues emergence of endothelial-like supporting layer |
| 16 | Harvest | |

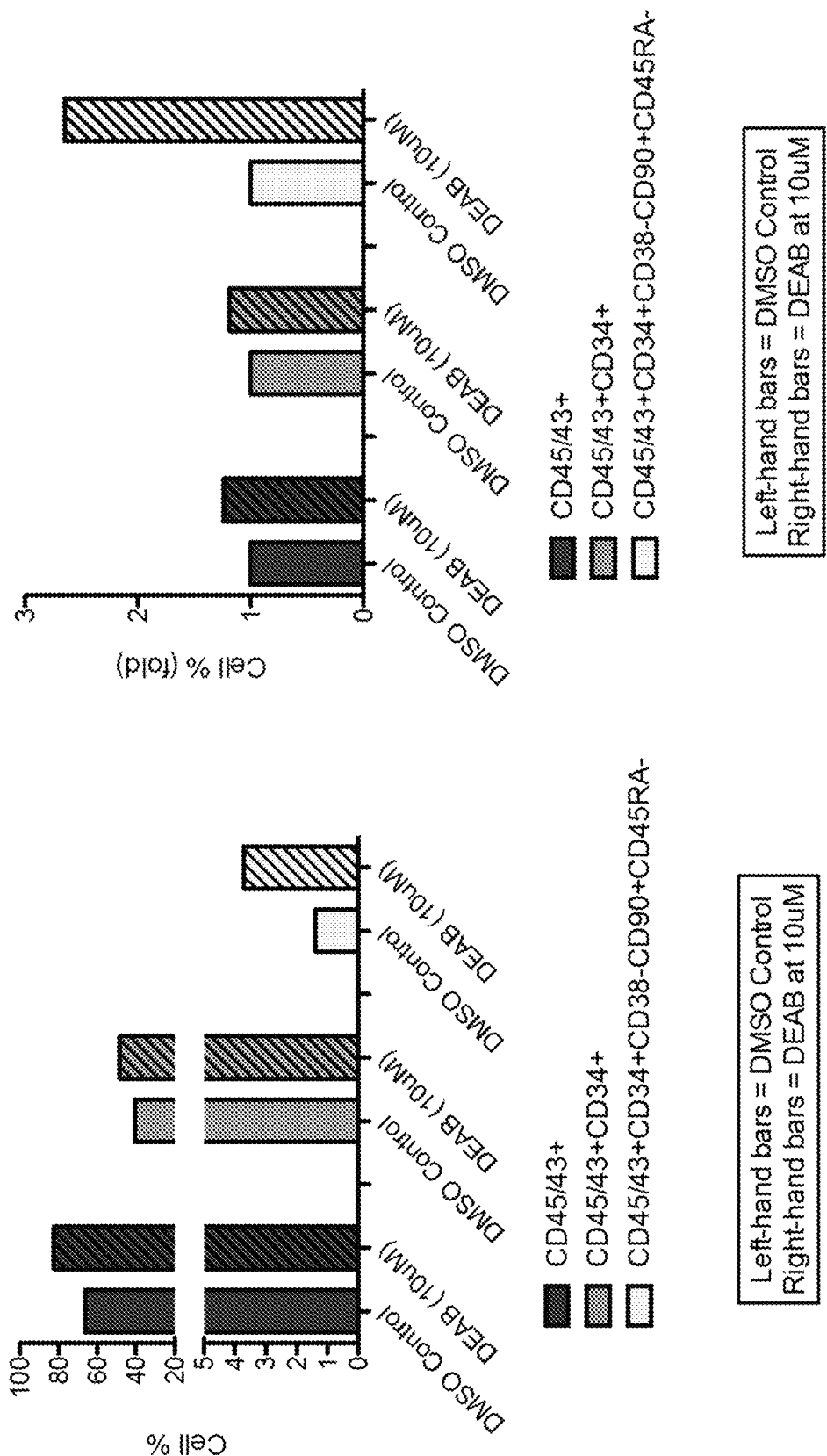

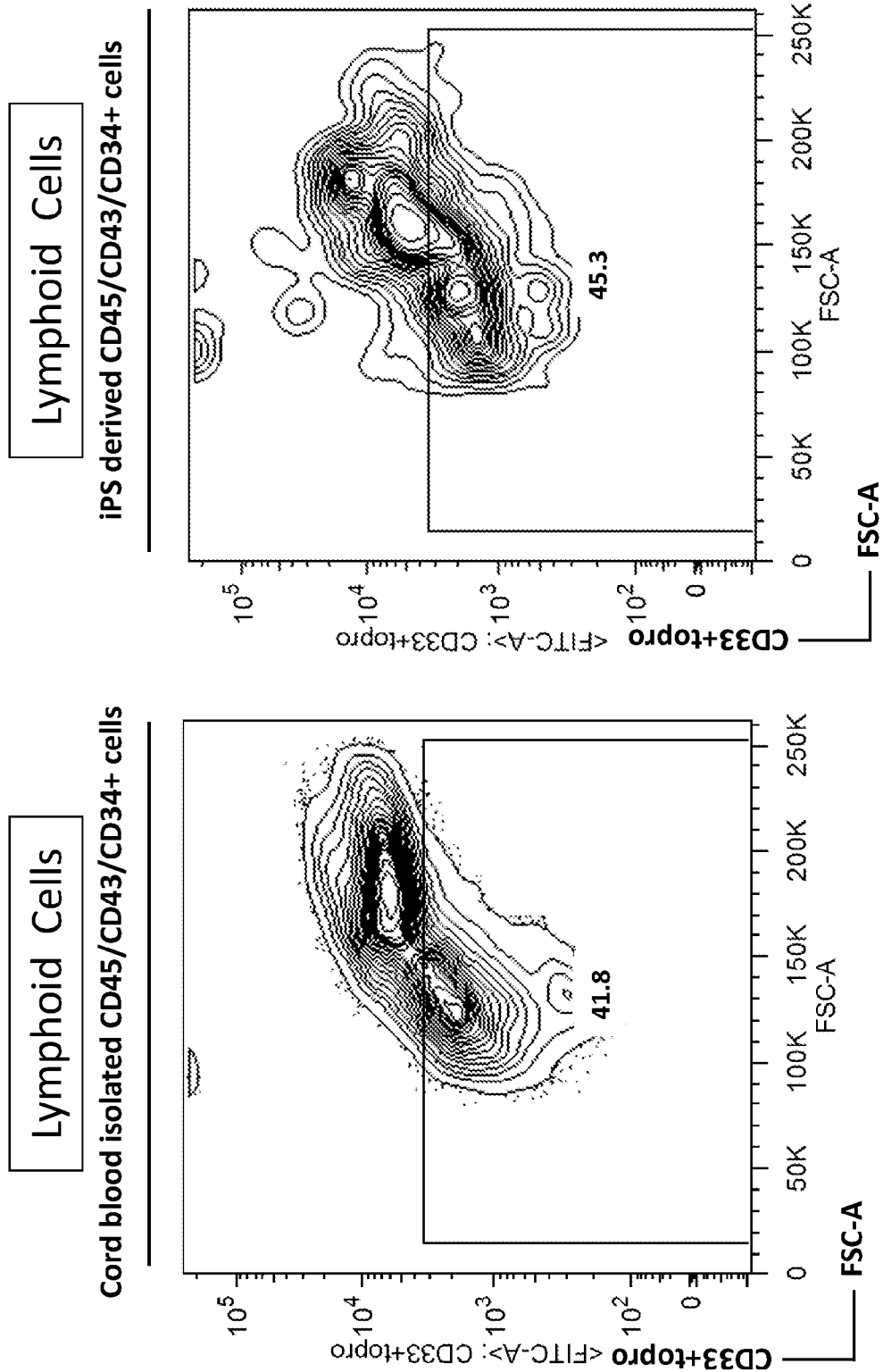

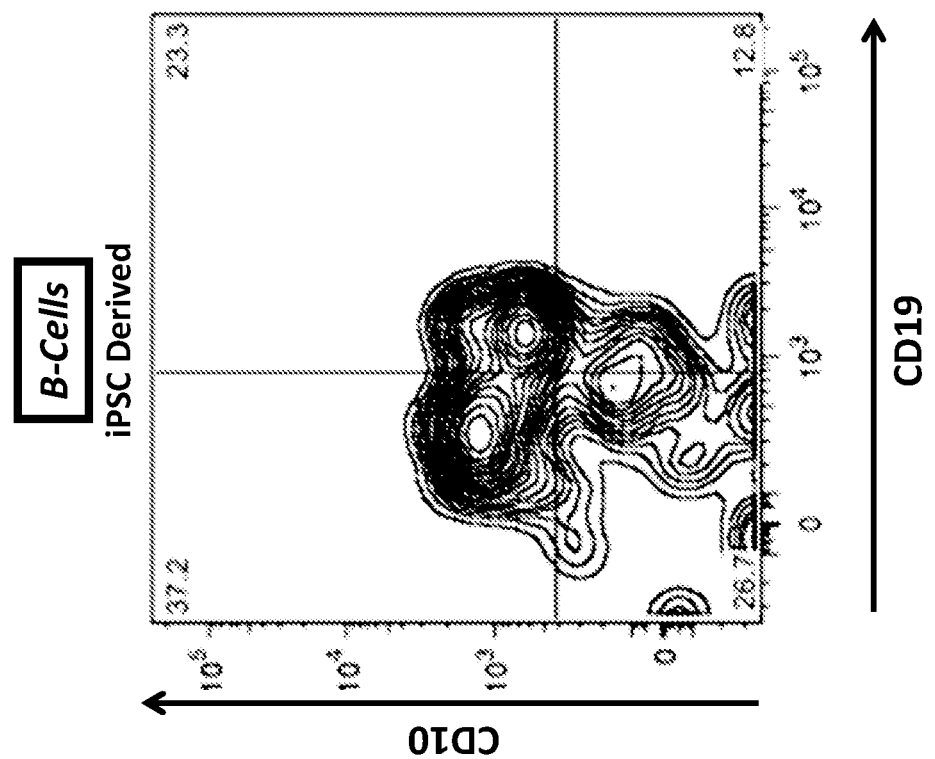
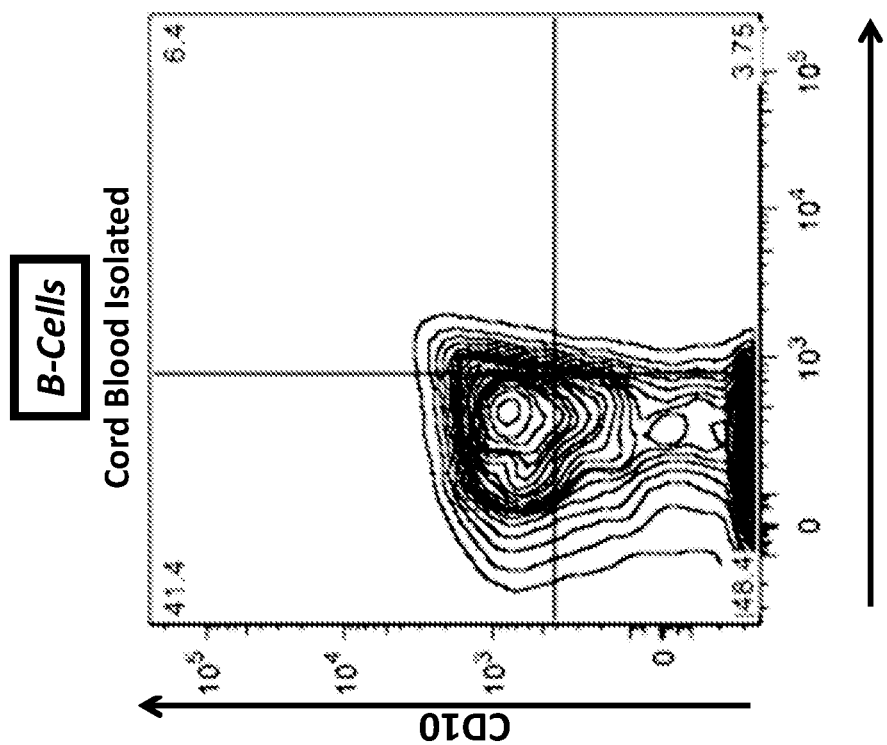
FIG. 7D
FIG. 7C

LY228820 p38 Inhibitor + DEAB increases number of primitive blood cells in ES Cells

| Phenotype | DMSO (DEAB Control) | LY228820 (plus DEAB) | Total % cell number increase |
|---|---|---|---|
| CD45+, CD34+ | 30.2% | 26.6% | |
| CD34+, CD38- | 30.1% | 28.9% | |
| CD90+, CD45RA- | 35.3% | 53.5% | 28% |

FIG. 8A

LY228820 p38 Inhibitor + DEAB increases number of primitive blood cells in iPS Cells

| Phenotype | DMSO (DEAB Control) | LY228820 (plus DEAB) | Total % cell number increase |
|---|---|---|---|
| CD45+, CD34+ | 30.1% | 36.7% | |
| CD34+, CD38- | 29.1% | 42.4% | |
| CD90+, CD45RA- | 28.7% | 54.3% | 336% |

FIG. 8B

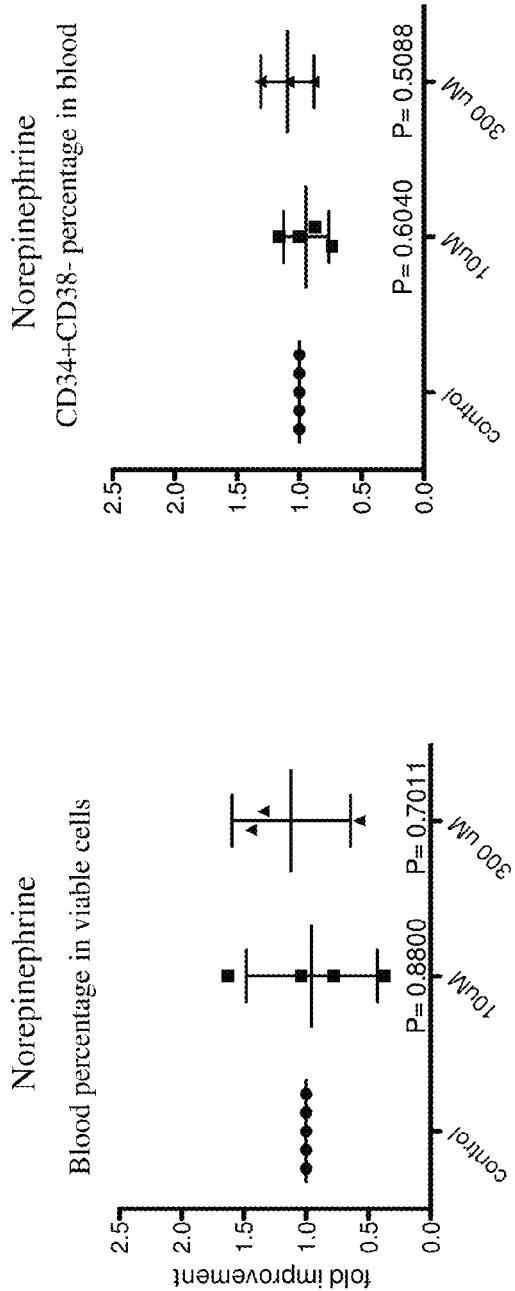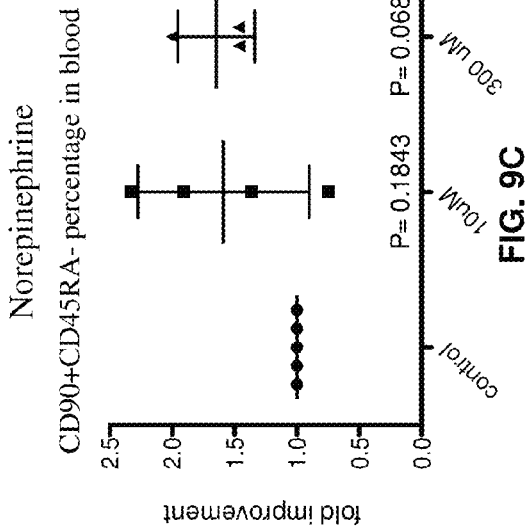

LG101506 inhibitor + DEAB increases number of primitive blood cells in ES cells

| Phenotype | DMSO (DEAB Control) | LG101506 (plus DEAB) | Total % cell number increase |
|---|---|---|---|
| CD45+, CD34+ | 30.2% | 34.7% | |
| CD34+, CD38- | 31.2% | 58.7% | |
| CD90+, CD45RA- | 25.8% | 23.6% | 97% |

FIG. 10A

LG101506 inhibitor + DEAB increases number of primitive blood cells in iPS cells

| Phenotype | DMSO (DEAB Control) | LG101506 (plus DEAB) | Total % cell number increase |
|---|---|---|---|
| CD45+, CD34+ | 29.9% | 33.8% | |
| CD34+, CD38- | 30.9% | 68.3% | |
| CD90+, CD45RA- | 26% | 25.9% | 248% |

FIG. 10B

Sodium Selenite + DEAB effects on number of primitive blood cells in ES Cells

| Phenotype | DMSO (DEAB Control) | Sodium Selenite (plus DEAB) | Total % cell number increase |
|---|---|---|---|
| CD45+, CD34+ | 30.2% | 18% | |
| CD34+, CD38- | 30.1% | 22% | |
| CD90+, CD45RA- | 35.3% | 36.7% | -55% |

FIG. 11A

Sodium Selenite + DEAB increases number of primitive blood cells in PS Cells

| Phenotype | DMSO (DEAB Control) | Sodium Selenite (plus DEAB) | Total % cell number increase |
|---|---|---|---|
| CD45+, CD34+ | 30.1% | 30.2% | |
| CD34+, CD38- | 29.1% | 37% | |
| CD90+, CD45RA- | 28.7% | 31.8% | 41% |

FIG. 11B

| Butein + DEAB increases number of primitive blood cells in ES Cells | | | |
|---|---|---|---|
| Phenotype | DMSO (DEAB Control) | Butein (plus DEAB) | Total % cell number increase |
| CD45+, CD34+ | 30.2% | 34.5% | |
| CD34+, CD38- | 30.1% | 35.9% | |
| CD90+, CD45RA- | 35.3% | 31.1% | 20% |

FIG. 12A

| Butein + DEAB increases number of primitive blood cells in iPS cells | | | |
|---|---|---|---|
| Phenotype | DMSO (DEAB Control) | Butein (plus DEAB) | Total % cell number increase |
| CD45+, CD34+ | 30.1% | 36.9% | |
| CD34+, CD38- | 29.1% | 34.1% | |
| CD90+, CD45RA- | 28.7% | 27.5% | 38% |

FIG. 12B

Valproic Acid + DEAB increases number of primitive blood cells in ES cells

| Phenotype | DMSO (DEAB Control) | Valproic Acid (plus DEAB) | Total % cell number increase |
|---|---|---|---|
| CD45+, CD34+ | 30.2% | 16.8% | |
| CD34+, CD38- | 30.1% | 87.5% | |
| CD90+, CD45RA- | 35.3% | 100% | 458% |

FIG. 13A

Valproic Acid + DEAB increases number of primitive blood cells in iPS cells

| Phenotype | DMSO (DEAB Control) | Valproic Acid (plus DEAB) | Total % cell number increase |
|---|---|---|---|
| CD45+, CD34+ | 30.1% | 13.1% | |
| CD34+, CD38- | 29.1% | 62.5% | |
| CD90+, CD45RA- | 28.7% | 100% | 325% |

FIG. 13B

COMPOSITIONS AND METHODS FOR DIFFERENTIATING PLURIPOTENT STEM CELLS INTO PRIMITIVE BLOOD CELLS AND USES THEREOF

CROSS-REFERENCE TO RELATED APPLICATIONS

This application claims priority under 35 USC §119(e) to U.S. Provisional Patent Application 61/566,940 filed Dec. 5, 2011, the entirety of which is incorporated herein by reference.

FIELD OF THE INVENTION

The invention is directed to compositions and methods for differentiating cells, such as differentiating pluripotent stem cells into primitive blood cells, and downstream uses thereof.

BACKGROUND

The scarcity of human embryonic tissue and the difficulty in manipulating this tissue for research purposes has increased the use of human induced pluripotent stem (iPS) cells and their in vitro differentiation systems. While factors that influence cell development and maturation have been explored, it is difficult to recapitulate embryonic development in vitro. The cell types, cellular niches/structures, and the resulting embryonic patterning are influenced by the artificial conditions in the in vitro setting, which often leads to disorganized, semi-complete development of organ systems.

Current published in vitro protocols demonstrate very limited efficiency in differentiating ES and iPS cells to hematopoietic lineages and, in particular, generating significant numbers of primitive hematopoietic stem cells, hematopoietic progenitors, and hematopoietic cells. This may be attributed partly to the inability of in vitro systems to mimic the processes of embryonic development towards the precursor cells of the hematopoietic system. Additionally, in vitro systems experience unwanted differentiation of ES and iPS cells towards non-blood lineages, such as neuroectoderm and cardiac (anterior lateral plate) mesoderm.

As a consequence, current published in vitro protocols produce insufficient numbers of immature hematopoietic output cells to perform hematopoietic stem cell (HSC) and progenitor or mature cell transplants in patients. It also is difficult to produce enough hematopoietic stem cells, hematopoietic progenitor cells, and hematopoietic cells for research and laboratory use.

The ability to generate hematopoietic stem cells, hematopoietic progenitor cells, and mature blood cells from patient derived induced pluripotent stem (iPS) cells, would enable the generation of an unlimited supply of human leukocyte antigen (HLA)-matched transplantable cells (with or without genetic modification, such as to correct a monogenic disease); these transplantable cells would be used for the treatment of both hematological disorders or malignancies where hematopoietic cell transplantation is required. There is a need for compositions and methods that produce such cells.

SUMMARY OF THE INVENTION

The present invention exploits novel pathways involved in hematopoietic stem and progenitor cell generation and expansion from human ES and iPS cells. Using the components described herein, we specifically enhance the generation of phenotypic adult hematopoietic stem cells and more closely mimic the developmental stages and/or niches of hematopoiesis in the embryo, including the aorta-gonad-mesonephros (AGM) niche environment, from which definitive hematopoiesis and repopulating hematopoietic stem cells are first established in the developing embryo.

As described herein, inhibiting retinoic acid (RA) signaling increases the expression of factors associated with mesoderm specification during germ layer specification and increases hemogenic mesodermal precursors and progenitors. In addition, inhibiting RA results in a 3-fold increase in hematopoietic cells having lymphoid and myeloid differentiation capacity and also having an adult cell surface HSC phenotype. This expansion is obtained without an increase in differentiated blood cells, indicative of increased self-renewal of these primitive multipotent blood cells.

One purpose of the invention is to better direct differentiation of pluripotent stem cells such as ES and iPS cells towards the mesoderm and hematopoietic lineage and thereby increase the efficiency of in vitro blood cell production systems. The system described herein demonstrates the successful recapitulation of the in vivo setting of RA roles during mammalian and human embryonic developmental stages. These results indicate that RA production during development and in the adult is highly regulated and an integral part of achieving tissue and organ development. The methods described herein provide improved protocols for pluripotent stem cell differentiation to blood, including HSCs, for transplantation into patients with hematological disorders and malignancies.

The compositions and methods provided herein ensure that as much of the pluripotent stem cell starting material as possible reaches a developmental state where it carries the capacity to give rise to hematopoietic cells. To avoid losing cells to unwanted differentiation, the system minimizes unwanted disturbances that would negatively affect the process of directed differentiation.

A version of a differentiation medium as provided herein comprises a retinoic acid signaling inhibitor, an antioxidant, and BMP4. The differentiation medium may further comprise one, all, or any subcombination of components selected from the group consisting of a stimulant of prostaglandin E2 pathway, TPO, VEGF, SCF, FLT-3, EPO, and TGFβ1. The differentiation medium may alternatively or additionally further comprise one, all, or any combination of components selected from the group consisting of a p38 MAPK inhibitor, a beta adrenergic receptor agonist, a cell cycle inhibitor, an RXR agonist, Cripto, and a chromatin remodeler. The p38 MAPK inhibitor is preferably LY2228820. The cell cycle inhibitor is preferably rapamycin. The RXR agonist is preferably LG101506. The beta adrenergic receptor agonist may comprise one, all, or any combination of components selected from the group consisting of norepinephrine, epinephrine, salmeterol, and isoproterenol. The chromatin remodeler is preferably valproic acid. The antioxidant may comprise one, all, or any combination of components selected from the group consisting of sodium selenite, butein, glutathione, and N-acetyl cysteine. The retinoic acid signaling inhibitor preferably comprises DEAB.

A version of a differentiation method as provided herein comprises exposing a cell to a differentiation medium as described above or otherwise described herein. The cell exposed to the differentiation medium is preferably a human cell. In certain versions, the cell is exposed to the differentiation medium in the absence of feeder cells. In some versions, the cell preferably comprises a pluripotent stem cell, and the cell is preferably exposed to the differentiation medium for a time and under conditions sufficient to generate a hematopoietic stem cell. The hematopoietic stem cell preferably is capable of further differentiating into a myeloid cell and also is preferably capable of further differentiating into a lymphoid cell. Exposing the cell to the differentiation medium preferably comprises initially exposing the cell to the differentiation medium by adding a volume of the differentiation medium to an existing volume of non-differentiation medium to generate a mixed medium, exposing the cell to the mixed medium, and subsequently replacing substantially all the mixed medium after about 12-48 hours from the initial exposure with a fresh volume of the differentiation medium. After replacing substantially all the mixed medium, a fresh volume of the differentiation medium preferably is added only to an existing volume of the differentiation medium, wherein the existing volume comprises medium exposed to the cell for a period of at least two hours. In certain versions, the cell comprises an intact embryoid body formed for a period of at least 7 days prior to the exposing. The intact embryoid body preferably is exposed to the differentiation medium for a period of at least 5 days prior to plating the embryoid body, which preferably is followed by plating the embryoid body. In certain versions, the embryoid body is plated in the absence of feeder cells. After plating, a fresh volume of the differentiation medium preferably is added only to an existing volume of the differentiation medium without removing any of the existing volume of the differentiation medium, wherein the existing volume comprises medium exposed to the cell for a period of at least 15 minutes. Some versions of the differentiation method further comprise differentiating the hematopoietic stem cell into a cell selected from the group consisting of a myeloid cell and a lymphoid cell. Differentiating the hematopoietic stem cell into a myeloid cell or a lymphoid cell may be performed in vitro, in vivo, or a combination thereof.

The invention further provides methods of engrafting a blood cell in a human subject. One version comprises administering a hematopoietic stem cell generated by a method as described above or a cell differentiated therefrom to the subject.

The objects and advantages of the invention will appear more fully from the following detailed description of the preferred embodiment of the invention made in conjunction with the accompanying drawings.

BRIEF DESCRIPTION OF THE DRAWINGS

FIGS. 1A-B depict schematics of a differentiation pathway from embryonic stem (ES) or induced pluripotent stem (iPS) cells to hematopoietic stem cells (HSCs). FIG. 1A shows the steps affected by DEAB and the effects resulting therefrom in accordance with a differentiation method of the present invention. FIG. 1B shows the steps affected by BMP4 and VEGF and the effects resulting therefrom in accordance with a differentiation method of the present invention.

FIGS. 2A and B depict aspects of a differentiation method of the present invention. FIG. 2A depicts a schematic of the differentiation pathway from embryonic stem (ES) or induced pluripotent stem (iPS) cells to hematopoietic stem cells (HSCs) with respect to a timeline of a differentiation method of the present invention. FIG. 2B depicts a table indicating method steps and effects thereof at select days of a differentiation method corresponding to the method shown in FIG. 2A.

FIG. 3A shows the fold change in phenotypic hematopoietic stem cells (CD45+, CD43+, CD34+, CD38−, CD90+, CD45RA−) for each screened compound relative to a DMSO control. FIG. 3B shows the total hematopoietic stem cell (CD45+, CD43+, CD34+, CD38−, CD90+, CD45RA−) output resulting from each screened compound compared to a DMSO control. FIG. 3C shows the fold increase in total blood cells (CD45+, CD43+) for each screened compound relative to a DMSO control.

FIGS. 4A-D depict results of iPS cells differentiated in media containing DEAB. FIG. 4A shows cell counts of total viable cells, total blood cells (CD45+, CD43+), progenitor cells (CD45+, CD43+, CD34+), and HSCs (CD45+, CD43+, CD34+, CD38−, CD90+, CD45RA−) differentiated in media containing DMSO (left-hand bars/non-hashed) or 10 µM DEAB (right-hand bars/hashed). FIG. 4B shows fold changes in cell counts of total viable cells, total blood cells (CD45+, CD43+), progenitor cells (CD45+, CD43+, CD34+), and HSCs (CD45+, CD43+, CD34+, CD38−, CD90+, CD45RA−) differentiated in media containing DMSO (left-hand bars/non-hashed) or 10 µM DEAB (right-hand bars/hashed). FIG. 4C shows viable cells, total blood cells (CD45+, CD43+), progenitor cells (CD45+, CD43+, CD34+), and HSCs (CD45+, CD43+, CD34+, CD38−, CD90+, CD45RA−) as a percentage of total cells differentiated in media containing DMSO (left-hand bars/non-hashed) or 10 µM DEAB (right-hand bars/hashed). FIG. 4D shows fold change in the percentage viable cells, total blood cells (CD45+, CD43+), progenitor cells (CD45+, CD43+, CD34+), and HSCs (CD45+, CD43+, CD34+, CD38−, CD90+, CD45RA−) with respect to total cells differentiated in media containing DMSO (left-hand bars/non-hashed) or 10 µM DEAB (right-hand bars/hashed).

FIG. 6A shows expression of PAX6. FIG. 6P shows expression of CD38.

FIG. 7A-J depict flow cytometry results of cells in the lymphoid lineage differentiated from cord blood-derived CD45+, CD43+, CD34+ cells and iPS-derived CD45+, CD43+, CD34+. The iPS-derived CD45+, CD43+, CD34+ cells used for differentiating into lymphoid cells were generated in the presence of DEAB in accordance with a method of the present invention FIGS. 7A and B show the population of CD33− cells (box within the heat map graph) sorted out for further lymphoid specific analysis. As CD33+ is a definitive marker for myeloid cells, these boxes represent non-myeloid (CD33−) cells presumed to be lymphoid cells differentiated from cord blood-derived or iPS-derived cells, respectively. FIGS. 7C and D show levels of B-lymphoid cells (CD33−, CD56−, CD10+, CD19+) differentiated from cord blood-derived or iPS-derived cells, respectively. FIGS. 7E and F show levels of T-lymphoid cells (CD56−, CD5+, CD7+) differentiated from cord blood-derived or iPS-derived cells, respectively. FIGS. 7G and H show levels of natural killer (NK) cells (CD16+, CD56+) differentiated from cord blood-derived or iPS-derived cells, respectively. FIGS. 7I and 7J show levels of helper T-lymphoid cells (CD56−, CD4+, CD3+) differentiated from cord blood-derived or iPS-derived cells, respectively.

FIGS. 8A and B depict summaries of flow cytometry results of cells differentiated from pluripotent stem cells in the presence of DEAB with and without the p38 inhibitor LY2228820, FIG. 8A shows the percentage of hematopoietic progenitors (CD45+, CD43+, CD34+; shown as "CD45+, CD34+"), intermediate cells between progenitor and phenotypic hematopoietic stem cells (CD45+, CD43+, CD34+, CD38−; shown as "CD45+, CD38−"), and phenotypic hematopoietic stem cells (CD45+, CD43+, CD34+, CD38−, CD90+, CD45RA−; shown as "CD90+, CD45RA−") among total cells differentiated from H1 ES cells, as well as the total % increase in HSC cell number resulting from exposure to LY2228820. FIG. 8B shows the percentage of hematopoietic progenitors (CD45+, CD43+, CD34+; shown as "CD45+, CD34+"), intermediate cells between progenitor and phenotypic hematopoietic stem cells (CD45+, CD43+, CD34+, CD38−; shown as "CD45+, CD38−"), and phenotypic hematopoietic stem cells (CD45+, CD43+, CD34+, CD38−CD90+, CD45RA−; shown as "CD90+, CD45RA−") among total cells differentiated from iPS cells, as well as the total % increase in HSC cell number resulting from exposure to LY2228820.

FIGS. 9A-C depict summaries of flow cytometry results of cells differentiated from human ES cells in the presence of DEAB (control) with and without various amounts of norepinephrine (10 µM or 300 µM). FIG. 9A shows fold changes in the percentage of blood cells among viable cells. FIG. 9B shows fold changes in the percentage of intermediate cells between progenitor and phenotypic hematopoietic stem cells (CD34+, CD38− cells) among total blood cells (CD45+, CD43+, CD34+, CD38−; shown as "CD34+, CD38−"). FIG. 9C shows fold changes in the percentage of phenotypic hematopoietic stem cells (CD45+, CD43+, CD34+, CD38−, CD90+, CD45RA−; shown as "CD90+, CD45RA−") among total blood cells.

FIGS. 10A and B depict summaries of flow cytometry results of cells differentiated from pluripotent stem cells in the presence of DEAB with and without LG101506. FIG. 10A shows the percentage of hematopoietic progenitors (CD45+, CD43+, CD34+; shown as "CD45+, CD34+"), intermediate cells between progenitor and phenotypic hematopoietic stem cells (CD45+, CD43+, CD34+, CD38−; shown as "CD45+, CD38−"), and phenotypic hematopoietic stem cells (CD45+, CD43+, CD34+, CD38−, CD90+, CD45RA−; shown as "CD90+, CD45RA−") among total cells differentiated from H1 ES cells, as well as the total % increase in HSC cell number resulting from exposure to LG1101506. FIG. 10B shows the percentage of hematopoietic progenitors (CD45+, CD43+, CD34+; shown as "CD45+, CD34+"), intermediate cells between progenitor and phenotypic hematopoietic stem cells (CD45+, CD43+, CD34+, CD38−; shown as "CD45+, CD38−"), and phenotypic hematopoietic stem cells (CD45+, CD43+, CD34+, CD38− CD90+, CD45RA−; shown as "CD90+, CD45RA−") among total cells differentiated from iPS cells, as well as the total % increase in HSC cell number resulting from exposure to LG101506.

FIGS. 11A and B depict summaries of flow cytometry results of cells differentiated from pluripotent stem cells in the presence of DEAB with and without sodium selenite. FIG. 11A shows the percentage of hematopoietic progenitors (CD45+, CD43+, CD34+; shown as "CD45+, CD34+"), intermediate cells between progenitor and phenotypic hematopoietic stem cells (CD45+, CD43+, CD34+, CD38−; shown as "CD45+, CD38−"), and phenotypic hematopoietic stem cells (CD45+, CD43+, CD34+, CD38−, CD90+, CD45RA−−; shown as "CD90+, CD45RA−") among total cells differentiated from H1 ES cells, as well as the total % increase in HSC cell number resulting from exposure to sodium selenite. FIG. 11B shows the percentage of hematopoietic progenitors (CD45+, CD43+, CD34+; shown as "CD45+, CD34+"), intermediate cells between progenitor and phenotypic hematopoietic stem cells (CD45+, CD43+, CD34+, CD38−; shown as "CD45+, CD38−"), and phenotypic hematopoietic stem cells (CD45+, CD43+, CD34+, CD38−, CD90+, CD45RA−; shown as "CD90+, CD45RA−") among total cells differentiated from iPS cells, as well as the total % increase in HSC cell number resulting from exposure to sodium selenite.

FIGS. 12A and B depict summaries of flow cytometry results of cells differentiated from pluripotent stem cells in the presence of DEAB with and without butein. FIG. 12A shows the percentage of hematopoietic progenitors (CD45+, CD43+, CD34+; shown as "CD45+, CD34+"), intermediate cells between progenitor and phenotypic hematopoietic stem cells (CD45+, CD43+, CD34+, CD38−; shown as "CD45+, CD38−"), and phenotypic hematopoietic stem cells (CD45+, CD43+, CD34+, CD38−, CD90+, CD45RA−; shown as "CD90+, CD45RA−") among total cells differentiated from H1 ES cells, as well as the total % increase in HSC cell number resulting from exposure to butein. FIG. 12B shows the percentage of hematopoietic progenitors (CD45+, CD43+, CD34+; shown as "CD45+, CD34+"), intermediate cells between progenitor and phenotypic hematopoietic stem cells (CD45+, CD43+, CD34+, CD38−; shown as "CD45+, CD38−"), and phenotypic hematopoietic stem cells (CD45+, CD43+, CD34+, CD38−, CD90+, CD45RA−; shown as "CD90 CD45RA−" among total cells differentiated from iPS cells as well as the total % increase in HSC cell number resulting from exposure to butein.

FIGS. 13A and B depict summaries of flow cytometry results of cells differentiated from pluripotent stem cells in the presence of DEAB with and without valproic acid. FIG. 13A shows the percentage of hematopoietic progenitors (CD45+, CD43+, CD34+; shown as "CD45+, CD34+"), intermediate cells between progenitor and phenotypic hematopoietic stem cells (CD45+, CD43+, CD34+, CD38−; shown as "CD45+, CD38−"), and phenotypic hematopoietic stem cells (CD45+, CD43+, CD34+, CD38−, CD90+, CD45RA−; shown as "CD90+, CD45RA−") among total cells differentiated from H1 ES cells, as well as the total % increase in HSC cell number resulting from exposure to valproic acid. FIG. 13B shows the percentage of hematopoietic progenitors (CD45+, CD43+, CD34±; shown as "CD45+, CD34+"), intermediate cells between progenitor and phenotypic hematopoietic stem cells (CD45+, CD43+, CD34+, CD38−; shown as "CD45+, CD38−"), and phenotypic hematopoietic stem cells (CD45+, CD43+, CD34+, CD38−, CD90+, CD45RA−; shown as "CD90+, CD45RA−") among total cells differentiated from iPS cells, as well as the total % increase in HSC cell number resulting from exposure to valproic acid.

DETAILED DESCRIPTION OF THE INVENTION

Figure 1B:
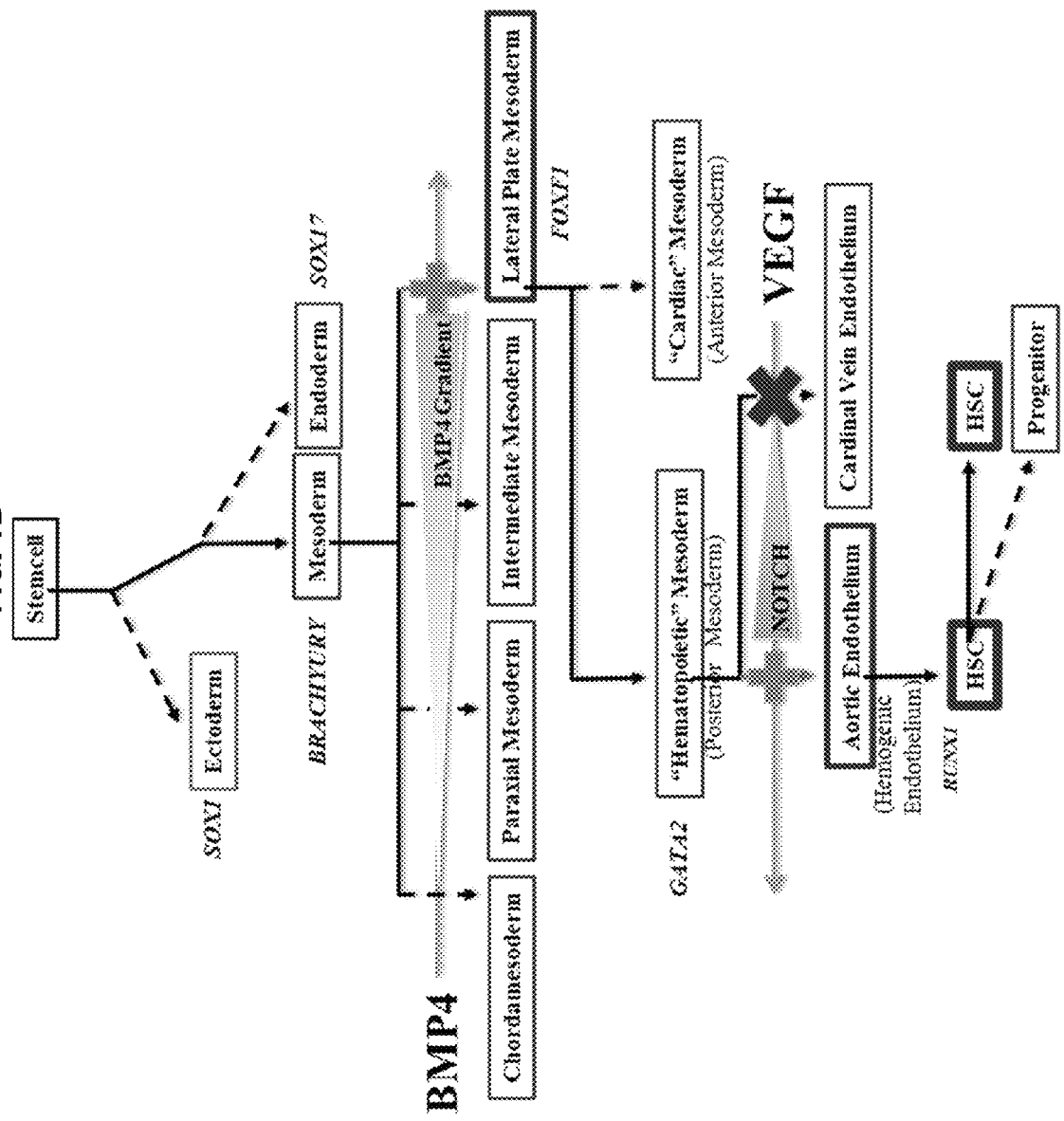

FIGS. 1A and B show the differentiation pathways exploited by the present invention in which stem cells (e.g., induced pluripotent stem cells (iPS) or embryonic stem (ES) cells) are differentiated into hematopoietic stem cells (HSCs) or hematopoietic progenitor cells. As depicted, stem cells sequentially differentiate into mesoderm, lateral plate mesoderm, hematopoietic mesoderm (posterior mesoderm), aortic endothelium (hemogenic endothelium), and then HSCs. A portion of the HSCs may further differentiate into progenitors. The HSCs also may expand to generate additional HSCs. Markers defining the above-mentioned cell types and those otherwise described herein are indicated in Table 1 and are selectively shown in FIG. 1B.

TABLE 1

Cell Markers

| Cell Type | Markers |
| --- | --- |
| Stem cell (ES or iPS) | OCT4, SSEA-3, SSEA-4, TRA-1-60, TRA-1-81, TRA-2-49/6E, SOX2, NANOG, DNMT3B, CRIPTO, KLF4, C-MYC, REX1 |
| Ectoderm | SOX1, Pax6 |
| Endoderm | SOX17, GATA4, SOX7 |
| Mesoderm | Brachyury, CD31 |
| Primitive streak mesoderm | MIXL1 |
| Paraxial mesoderm | FOXF1 |
| Lateral Plate Mesoderm | FOXC1 |
| Cardiac mesoderm (Anterior lateral plate mesoderm) | NKX2.5 |
| Hematopoietic mesoderm (Posterior lateral plate mesoderm) | SAL1, Wnt, GATA2, SCL, FOXC1, NKX2.5 (low) |
| Aortic endothelium (Hemogenic endothelium) | APLNR, PDGFRA (low), FLK1 |
| Hematopoietic progenitor cell (HPC) - Pluripotent stem cell-derived | (CD45+, CD43+, CD34+), (CD45+, CD34+), (CD43+, CD34+), (CD45+, CD90+), (CD43+, CD90+), (CD45+, CD43+, CD90+), (CD45+, CD43+, CD34+, CD38−), (CD45+, CD34+, CD38−), (CD43+, CD34+, CD38−) |
| Hematopoietic progenitor cell (HPC) - Cord blood-derived | (CD45+, CD43+, CD34+), (CD45+, CD34+), (CD43+, CD34+), (CD45+CD90+), (CD43+ CD90+), (CD45+, CD43+, CD90+), (CD45+, CD43+, CD34+, CD38−), (CD45+, CD34+, CD38−), (CD43+, CD34+, CD38−) |
| Multipotent progenitor cell (MPP) - Cord blood derived | (CD45+, CD43+, CD34+, CD38−, CD90−, CD45RA−), (CD43+, CD34+, CD38−, CD90−, CD45RA−), (CD45+, CD34+, CD38−, CD90−, CD45RA−), (CD45+, CD43+, CD34+, CD38−, CD90−), (CD43+, CD34+, CD38−, CD90−), (CD45+, CD34+, CD38−, CD90−), (CD45+, CD43+, CD34+, CD38−), (CD43+, CD34+, CD38−), (CD45+, CD34+, CD38−), (CD45+, CD43+, CD34+), (CD43+, CD34+), (CD45+, CD34+) |
| Hematopoietic stem cell (HSC), adult hematopoietic stem cell, phenotypic stem cell) - Pluripotent stem cell derived | (CD45+, CD43+, CD34+, CD90+, CD45RA−), (CD45+, CD43+, CD34+, CD90−, CD45RA−), (CD45+, CD43+, CD34+, CD90+, CD45RA−, CD49f+), (CD45+, CD43+, CD34+, CD90+, CD45RA−, Rhodamine (low)), (CD45+, CD43+, CD34+, CD90−), (CD45+, CD43+, CD34+, CD90+, CD45RA−, CD49f+, Rhodamine (low)), (CD45+, CD34+, CD90+, CD45RA−), (CD45+, CD34+, CD90−), (CD45+, CD34+, CD90+, CD45RA−, CD49f+), (CD45+, CD34+, CD90−), (CD45+, CD34+, CD90+, CD45RA−, Rhodamine (low)), (CD45+, CD34+, CD90−), (CD45+, CD34+, CD90+, CD45RA−, CD49f+, Rhodamine (low)), (CD43+, CD34+, CD90+, CD45RA−), (CD43+, CD34+, CD90−), (CD43+, CD34+, CD90+, CD45RA−, CD49f+), (CD43+, CD34+, CD90+, |

TABLE 1-continued

Cell Markers

| Cell Type | Markers |
|---|---|
|  | CD45RA−, Rhodamine (low)), (CD43+, CD34+, CD90+, CD45RA−, CD49f+, Rhodamine (low)), (CD45+, CD90+), (CD45+, CD90−), (CD45+, CD90+, CD49f+), (CD45+, CD90−), (CD45+, CD90+, Rhodamine (low)), (CD45+, CD90+, CD49f+, Rhodamine (low)), (CD43+, CD90+), (CD43+, CD90−), (CD43+, CD90+, CD49f+), (CD43+, CD90+, Rhodamine (low)), (CD43+, CD90+, CD49f+, Rhodamine (low)), (CD45+, CD43+, CD90+), (CD45+, CD43+, CD90−, CD45RA−), (CD45+, CD43+, CD90+, CD49f+), (CD45+, CD43+, CD90−), (CD45+, CD43+, CD90+, Rhodamine (low)), (CD45+, CD43+, CD90+, CD45RA−, CD49f+, Rhodamine (low)), (CD45+, CD43+, CD34+, CD38−, CD90+, CD45RA−), (CD45+, CD43+, CD34+, CD38−, CD90−), (CD45+, CD43+, CD34+, CD38−, CD90+, CD45RA−CD49f+), (CD45+, CD43+, CD34+, CD38−, CD90−), (CD45+, CD43+, CD34+, CD38−, CD90+, CD45RA−, Rhodamine (low)), (CD45+, CD43+, CD34+, CD38−, CD90−), (CD45+, CD43+, CD34+, CD38−, CD90+, CD45RA−, CD49f+, Rhodamine (low)), (CD45+, CD34+, CD38−, CD90+, CD45RA−), (CD45+, CD34+, CD38−, CD90−), (CD45+, CD34+, CD38−, CD90+, CD45RA−, CD49f+), (CD45+, CD34+, CD38−, CD90−), (CD45+, CD34+, CD38−, CD90+, CD45RA−, Rhodamine (low)), (CD45+, CD34+, CD38−, CD90+, CD45RA−, CD49f+, Rhodamine (low)), (CD43+, CD34+, CD38−, CD90+, CD45RA−), (CD43+, CD34+, CD38−, CD90−), (CD43+, CD34+, CD38−, CD90+, CD45RA−, CD49f+), (CD43+, CD34+, CD38−, CD90+, CD45RA−, Rhodamine (low)), (CD43+, CD34+, CD38−, CD90+, CD45RA−, CD49f+, Rhodamine (low)), (CD45+, CD38−, CD90+), (CD45+, CD38−, CD90−), (CD45+, CD38−, CD90+, CD45RA−, CD49f+), (CD45+, CD38−, CD90+, CD45RA−, Rhodamine (low)), (CD45+, CD38−, CD90+, CD45RA−, CD49f+, Rhodamine (low)), (CD43+, CD38−, CD90+), (CD43+, CD38−, CD90+, CD49f+), (CD43+, CD38−, CD90+, Rhodamine (low)), (CD43+, CD38−, CD90+, CD49f+, Rhodamine (low)), (CD43+, CD38−, CD90−), (CD45+, CD43+, CD34+CD38−, CD90+), (CD45+, CD43+, CD34+, CD38−, CD90−), (CD45+, CD43+, CD34+, CD38−, CD90+, CD49f+), (CD45+, CD43+, CD34+, CD38−, CD90−, CD49f+), (CD45+, CD43+, CD34+, CD38−, CD90+, Rhodamine (low)), (CD45+, CD43+, CD34+, CD38−, CD90−, Rhodamine (low)), (CD45+, CD43+, CD34+, CD38−, CD90+, CD49f+, Rhodamine (low)), (CD45+, CD43+, CD34+, CD38−, CD90−, CD49f+, Rhodamine (low)) |
| Hematopoietic stem cell (HSC, adult hematopoietic stem cell, phenotypic stem cell) - Cord blood derived | (CD45+, CD43+, CD34+, CD38−, CD90+, CD45RA−) or (CD45+, CD34+, CD38−, CD90+, CD45RA−) or (CD43+, CD34+, CD38−, CD90+, CD45RA−), (CD45+, CD43+, CD34+, CD38−, CD90+, CD45RA−, CD49f+) or (CD45+, CD34+, CD38−, CD90+, CD45RA−, CD49f+) or (CD43+, CD34+, CD38−, CD90+, CD45RA−, CD49f+), (CD45+, CD43+, CD34+, CD38−, CD90+, CD45RA−, CD49f+, Rhodamine (low)) or (CD45+, CD34+, CD38−, CD90+, CD45RA−, CD49f+, Rhodamine (low)) or (CD43+, CD34+, CD38−, CD90+, CD45RA−, CD49f+, Rhodamine (low)) |

FIG. 1A shows the effects of 4-diethylaminobenzaldehyde (DEAB) in the present invention. DEAB is a retinoic acid signaling inhibitor. DEAB promotes differentiation of stem cells toward mesoderm and away from ectoderm; promotes differentiation of mesoderm toward lateral plate mesoderm and away from chordamesoderm, paraxial mesoderm, and intermediate mesoderm; promotes differentiation of lateral plate mesoderm toward hematopoietic mesoderm and away from cardiac mesoderm (anterior mesoderm); promotes differentiation of hematopoietic mesoderm toward aortic endothelium and away from cardinal vein endothelium; promotes expansion of HSCs; and inhibits the differentiation of HSCs into progenitor cells. DEAB also inhibits RA production, which contributes to DEAB's effects at some of the aforementioned steps, as shown. In addition, stem cell leukemia (SCL; also known as TAL1 (T-cell acute lymphoblastic leukemia 1)) expression also promotes differentiation of lateral plate mesoderm toward hematopoietic mesoderm and away from cardiac mesoderm (see Ishiguro et al., *Leuk Res.*, 2009 September, 33(9):1249-1254; and Huang et al., *Mol Cell Biol.*, 2000 March, 20(6):2248-59).

Accordingly, some versions of the differentiation medium of the present invention include DEAB. In certain embodiments, DEAB is included in a differentiation medium of the present invention at a concentration of from about 0.1 to about 1,000 µM, from about 0.3 to about 300 µM, from about 1 to about 100 µM, from about 3 to about 30 µM, or any range derivable therein. In certain embodiments, DEAB is included in the differentiation medium at a concentration of about 0.1, about 0.3, about 1, about 5, about 10, about 15, about 20, about 25, about 30, about 40, about 50, about 100, about 300, or about 1,000 µM.

In certain embodiments, DEAB is included in a differentiation medium of the present invention in an amount sufficient to increase the total number of CD45+, CD43+, CD34+, CD38−, CD90+, CD45RA− cells obtained through differentiation therewith compared to the total number of CD45+, CD43+, CD34+, CD38−, CD90+, CD45RA− cells obtained through differentiation with an identical differentiation medium lacking DEAB. The increase in the total number of CD45+, CD43+, CD34+, CD38−, CD90+, CD45RA− cells may be at least about 1.1-fold, about 1.25-fold, about 1.5-fold, about 1.75-fold, about 2-fold, about 2.25-fold, about 2.5-fold, about 2.75-fold, about 3-fold, or more.

In certain embodiments, DEAB is included in a differentiation medium of the present invention in an amount sufficient to increase the proportion of CD45+, CD43+, CD34+, CD38−, CD90+, CD45RA− cells obtained through differentiation therewith compared to the proportion of CD45+, CD43+, CD34+, CD38−, CD90+, CD45RA− cells obtained through differentiation with an identical differentiation medium lacking DEAB. The increase in the proportion of CD45+, CD43+, CD34+, CD38−, CD90+, CD45RA− cells may be at least about 1.1-fold, about 1.25-fold, about 1.5-fold, about 1.75-fold, about 2-fold, about 2.25-fold, about 2.5-fold, about 2.75-fold, about 3-fold, or more.

In certain embodiments, DEAB is included in a differentiation medium of the present invention in an amount sufficient to increase the number of myeloid progenitor cells obtained through differentiation therewith compared to the number of myeloid progenitor cells obtained through differentiation with an identical differentiation medium lacking DEAB. The increase in the number of myeloid progenitor cells may be at least about 1.1-fold, about 1.25-fold, about 1.5-fold, about 1.75-fold, about 2-fold, about 2.25-fold, about 2.5-fold, about 2.75-fold, about 3-fold, or more.

In certain embodiments, DEAB is included in a differentiation medium of the present invention in an amount sufficient to increase the proportion of myeloid progenitor cells obtained through differentiation therewith compared to the proportion of myeloid progenitor cells obtained through differentiation with an identical differentiation medium lacking DEAB. The increase in the number of myeloid progenitor cells may be at least about 1.1-fold, about 1.25-fold, about 1.5-fold, about 1.75-fold, about 2-fold, about 2.25-fold, about 2.5-fold, about 2.75-fold, about 3-fold, or more.

The increase in myeloid progenitor cells may include increases in erythroid progenitors, granulocyte progenitors, macrophage progenitors, and multi-potential granulocyte, erythroid, macrophage, and megakaryocyte progenitors. Increases in such myeloid progenitor cells may be identified by testing for increases in erythroid burst-forming units (BFU-E), granulocyte colony-forming units (CFU-G), macrophage colony-forming units (CFU-M), and/or multi-potential granulocyte, erythroid, macrophage, megakaryocyte colony-forming units (CFU-GEMM), respectively, as shown herein.

In certain embodiments, DEAB is included in a differentiation medium of the present invention in an amount sufficient to generate HSCs and/or progenitor cells which are capable of differentiating into lymphoid cells. Such lymphoid cells may include B-lymphoid cells (CD33−, CD56−, CD10+, CD19+), T-lymphoid cells (CD56−, CD5+, CD7+), natural killer (NK) cells (CD3−, CD56+), and/or helper T-lymphoid cells (CD56−, CD4+, CD3+). Determining whether HSCs and/or progenitor cells are capable of differentiating into lymphoid cells can be carried out with a lymphocyte differentiation protocol as described in Charoudeh et al., *Blood*, 2010, 116(2):183-92, discussed in detail below.

In certain embodiments, DEAB is included in a differentiation medium of the present invention in an amount sufficient to increase the amount or proportion of HSCs and/or progenitor cells capable of differentiating into lymphoid cells compared to the amount or proportion of HSCs and/or progenitor cells capable of differentiating into lymphoid cells obtained with an identical differentiation medium lacking DEAB. Such lymphoid cells may include B-lymphoid cells (CD33−, CD56−, CD10+, CD19+), T-lymphoid cells (CD56−, CD5+, CD7+), natural killer (NK) cells (CD3−, CD56+), and/or helper T-lymphoid cells (CD56−, CD4+, CD3+). Determining an increase in the amount or proportion of HSCs and/or progenitor cells capable of differentiating into lymphoid cells can be carried out with a lymphocyte differentiation protocol as described in Charoudeh et al., *Blood*, 2010, 116(2):183-92.

In certain embodiments, DEAB is included in a differentiation medium of the present invention in an amount sufficient to generate HSCs and/or progenitor cells that are capable of differentiating into both lymphoid cells and myeloid cells. Such cells may include myeloid cells (CD33+) and B-lymphoid cells (CD33−, CD56−, CD10+, CD19+), T-lymphoid cells (CD56−, CD5+, CD7+), natural killer (NK) cells (CD3−, CD56+), and/or helper T-lymphoid cells (CD56−, CD4+, CD3+). Determining whether HSCs and/or progenitor cells are capable of differentiating into lymphoid cells can be carried out with a lymphocyte differentiation protocol as described in Charoudeh et al., *Blood*, 2010, 116(2):183-92, discussed in detail below.

In certain embodiments, DEAB is included in a differentiation medium of the present invention in an amount sufficient to decrease a level of PAX6 expression in cells exposed to the medium with respect to a level of PAX6 expression in cells exposed to an identical differentiation medium lacking DEAB. The relative decrease in the level of PAX6 expression preferably occurs on about day 4 and day 12 after exposure to the media.

In certain embodiments, DEAB is included in a differentiation medium of the present invention in an amount sufficient to increase a level of Brachyury expression in cells exposed to the medium with respect to a level of Brachyury expression in cells exposed to an identical differentiation medium lacking DEAB. The relative increase in the level of Brachyury expression preferably occurs on about day 4 after exposure to the media.

In certain embodiments, DEAB is included in a differentiation medium of the present invention in an amount sufficient to increase a level of MIXL.1 expression in cells exposed to the medium with respect to a level of MIXL.1 expression in cells exposed to an identical differentiation medium lacking DEAB. The relative increase in the level of MIXL.1 expression preferably occurs on about day 4 after exposure to the media.

In certain embodiments, DEAB is included in a differentiation medium of the present invention in an amount sufficient to decrease a level of SOX17 expression in cells exposed to the medium with respect to a level of SOX17 expression in cells exposed to an identical differentiation medium lacking DEAB. The relative decrease in the level of SOX17 expression preferably occurs on about day 4 after exposure to the media.

In certain embodiments, DEAB is included in a differentiation medium of the present invention in an amount sufficient to increase FOXF1 expression in cells exposed to the medium with respect to a level of FOXF1 expression in cells exposed to an identical differentiation medium lacking DEAB. The relative decrease in the level of FOXF1 expression preferably occurs on about day 4 after exposure to the media.

In certain embodiments, DEAB is included in a differentiation medium of the present invention in an amount sufficient to decrease a level of FOXC1 expression in cells exposed to the medium with respect to a level of FOXC1 expression in cells exposed to an identical differentiation medium lacking DEAB. The relative decrease in the level of FOXC1 expression preferably occurs on about day 8 after exposure to the media.

In certain embodiments, DEAB is included in a differentiation medium of the present invention in an amount sufficient to decrease a level of NKX2.5 expression in cells exposed to the medium with respect to a level of NKX2.5 expression in cells exposed to an identical differentiation medium lacking DEAB. The relative decrease in the level of NKX2.5 expression preferably occurs on about day 8 after exposure to the media.

In certain embodiments, DEAB is included in a differentiation medium of the present invention in an amount sufficient to decrease a level of APLNR expression in cells exposed to the medium with respect to a level of APLNR expression in cells exposed to an identical differentiation medium lacking DEAB. The relative decrease in the level of APLNR expression preferably occurs on about day 12 after exposure to the media.

In certain embodiments, DEAB is included in a differentiation medium of the present invention in an amount sufficient to decrease a level of PDGFRA expression in cells exposed to the medium with respect to a level of PDGFRA expression in cells exposed to an identical differentiation medium lacking DEAB. The relative decrease in the level of PDGFRA expression preferably occurs on about day 12 after exposure to the media.

In certain embodiments, DEAB is included in a differentiation medium of the present invention in an amount sufficient to increase a level of FLK1 expression in cells exposed to the medium with respect to a level of FLK1 expression in cells exposed to an identical differentiation medium lacking DEAB. The relative increase in the level of FLK1 expression preferably occurs on about day 15 after exposure to the media.

In certain embodiments, DEAB is included in a differentiation medium of the present invention in an amount sufficient to increase a level of RUNX1 expression in cells exposed to the medium with respect to a level of RUNX1 expression in cells exposed to an identical differentiation medium lacking DEAB. The relative increase in the level of RUNX1 expression preferably occurs on about day 15 after exposure to the media.

In certain embodiments, DEAB is included in a differentiation medium of the present invention in an amount sufficient to increase a level of SCL expression in cells exposed to the medium with respect to a level of SCL expression in cells exposed to an identical differentiation medium lacking DEAB. The relative increase in the level of SCL expression preferably occurs on about day 15 after exposure to the media.

In certain embodiments, DEAB is included in a differentiation medium of the present invention in an amount sufficient to decrease a level of RARbeta expression in cells exposed to the medium with respect to a level of RARbeta expression in cells exposed to an identical differentiation medium lacking DEAB. The relative decrease in the level of RARbeta expression preferably occurs on about days 8 and/or 12 after exposure to the media.

In certain embodiments, DEAB is included in a differentiation medium of the present invention in an amount sufficient to decrease a level of a gene upregulated by retinoic acid in cells exposed to the medium with respect to a level of the gene in cells exposed to an identical differentiation medium lacking DEAB. An exemplary gene upregulated by retinoic acid exposure includes CD38. The relative decrease in the level of the gene upregulated by retinoic acid preferably occurs on about days 8, 12, and/or 15 after exposure to the media.

In certain embodiments, DEAB is included in a differentiation medium of the present invention in an amount sufficient to increase the number and/or proportion of pluripotent stem cells differentiating to mesoderm when exposed to the medium with respect to the number and/or proportion of pluripotent stem cells differentiating to mesoderm when exposed to an identical differentiation medium lacking DEAB. Such a relative increase in the number and/or proportion of pluripotent stem cells differentiating to mesoderm can be identified by a DEAB-dependent increase in expression level of MIXL1 at about day 4 after exposure to the media, a DEAB-dependent increase in expression level of Brachyury at about day 4 and/or day 8 after exposure to the media, a DEAB-dependent decrease in expression level of PAX6 at about day 4 after exposure to the media, and/or a DEAB-dependent decrease in expression level of SOX17 at about day 4 after exposure to the media.

In certain embodiments, DEAB is included in a differentiation medium of the present invention in an amount sufficient to increase the number and/or proportion of mesoderm cells differentiating to lateral plate mesoderm when exposed to the medium with respect to the number and/or proportion of mesoderm cells differentiating to lateral plate mesoderm when exposed to an identical differentiation medium lacking DEAB. Such a relative increase in the number and/or proportion of mesoderm cells differentiating to lateral plate mesoderm can be identified by a DEAB-dependent increase in expression level of FOXF1 at about day 4 after exposure to the media and/or a DEAB-dependent decrease in expression level of FOXC1 at about day 8 after exposure to the media.

In certain embodiments, DEAB is included in a differentiation medium of the present invention in an amount sufficient to increase the number and/or proportion of lateral plate mesoderm cells differentiating to posterior mesoderm when exposed to the medium with respect to the number and/or proportion of lateral plate mesoderm cells differentiating to posterior mesoderm when exposed to an identical differentiation medium lacking DEAB. Such a relative increase in the number and/or proportion of lateral plate mesoderm cells differentiating to anterior mesoderm can be identified by a DEAB-dependent increase in expression level of NKX2.5 at about day 8 after exposure to the media.

In certain embodiments, DEAB is included in a differentiation medium of the present invention in an amount sufficient to decrease the number and/or proportion of lateral plate mesoderm cells differentiating to anterior mesoderm when exposed to the medium with respect to the number and/or proportion of lateral plate mesoderm cells differentiating to anterior mesoderm when exposed to an identical differentiation medium lacking DEAB. Such a relative decrease in the number and/or proportion of lateral plate mesoderm cells differentiating to anterior mesoderm can be identified by a DEAB-dependent decrease in expression level of APLNR at about day 8 after exposure to the media.

In certain embodiments, DEAB is included in a differentiation medium of the present invention in an amount sufficient to increase the number and/or proportion of lateral plate mesoderm cells differentiating to posterior mesoderm when exposed to the medium with respect to the number and/or proportion of lateral plate mesoderm cells differentiating to posterior mesoderm when exposed to an identical differentiation medium lacking DEAB. Such a relative increase in the number and/or proportion of lateral plate mesoderm cells differentiating to posterior mesoderm can be identified by a DEAB-dependent decrease in expression level of NKX2.5 at about day 8 after exposure to the media.

In certain embodiments, DEAB is included in a differentiation medium of the present invention in an amount sufficient to generate definitive HSCs when pluripotent stem cells are contacted with the medium. As used herein, "definitive" refers to the ability of an HSC to differentiate into all types blood cell, i.e., the HSC is not incapable of making any particular type of blood cell. Exemplary types of blood cells include lymphoid cells and myeloid cells. Exemplary lymphoid cells include B-lymphoid cells (CD33−, CD56−, CD10+, CD19+), T-lymphoid cells (CD56−, CD5+, CD7+), natural killer (NK) cells (CD3−, CD56+), and/or helper T-lymphoid cells (CD56−, CD4+, CD3+). Exemplary myeloid cells include erythrocytes, granulocytes, monocytes, and megakaryocytes. Definitive HSCs can be identified by differentiating the HSCs into the above cell types, preferably, in combination with expression of RUNX1, a definitive hematopoietic cell marker, at about day 15 after exposure to the media.

In certain embodiments, DEAB is included in a differentiation medium of the present invention in an amount sufficient to decrease a level of CD31 and/or SCL expression in cells exposed to the medium with respect to a level of CD31 and/or SCL expression, respectively, in cells exposed to an identical differentiation medium lacking DEAB. CD31 and/or SCL are indicators of precursors, progenitors, and/or cells of both primitive and definitive hematopoiesis and hemangioblast activity. Primitive hematopoiesis refers to an early wave ("primitive wave") of blood formation during development that is known to take place in the yolksac and is generally considered to occur outside of the AGM region during development. This primitive wave generates hemangioblasts from precursor cells. Hemangioblasts have limited differentiation ability, are restricted largely to the myeloid lineage, have lower proliferation capacity, and produce erythroid cells that express embryonic and fetal hemoglobins and show limited enucleation. The relative decrease in the level of CD31 and/or SCL expression preferably occurs on about day 8 after exposure to the media, when the primitive wave of hematopoiesis occurs. High levels of CD31 and/SCL expression without DEAB at day 8 is indicative of hemangioblast activity and primitive (not definitive) hematopoiesis at this time point.

In certain embodiments of a differentiation medium of the present invention, other retinoic acid (RA) signaling inhibitors may replace or be included with DEAB at the above-described amounts or concentrations. These other RA signaling inhibitors may act upstream or downstream of the RARa, RARb, or RARX receptor to inhibit signaling therefrom. The other RA signaling inhibitors may also inhibit RA production. Exemplary retinoic acid signaling inhibitors include disulfuram (tetraethylthiuram disulfide or bis(diethylthiocarbamyoyl)disulfide), retinoic acid receptor-β inhibitor LE135, the pan RA antagonist AGN 193109, and agonists of CYP26 or other molecules that aid in RA degradation.

FIG. 1B shows the role of bone morphogenetic protein-4 (BMP4) and vascular endothelial growth factor (VEGF) in the present invention. BMP4 promotes differentiation of mesoderm toward lateral plate mesoderm and away from chordamesoderm, paraxial mesoderm, and intermediate mesoderm. VEGF promotes differentiation of hematopoietic mesoderm toward aortic endothelium and away from cardinal vein endothelium. It is thought that VEGF, at least in part, carries out its effects by Notch signaling.

Accordingly, some versions of the differentiation medium of the present invention include BMP4. BMP4 is a member of the group of bone morphogenic proteins and is a ventral mesoderm inducer. BMPs are expressed in adult human bone marrow (BM) and are important for bone remodeling and growth. In differentiation media described herein, BMP4 biases differentiation towards lateral plate mesoderm and away from chordamesoderm, paraxial mesoderm, or intermediate mesoderm, thereby enhancing generation of HSCs. See FIG. 1B. BMP4 promotes mesoderm formation from pluripotent stem cells by inducing expression of primitive streak and early hematopoietic mesoderm genes, such as Brachyury and MIXL1, and by activating SMAD. BMP4 also enhances progenitor self-renewal and development of primitive hematopoietic cells. In certain embodiments, BMP4 is included in a differentiation medium of the present invention at a concentration of from about 0.1 to about 1,000 ng/mL, from about 0.3 to about 300 ng/mL, from about 1 to about 100 ng/mL, from about 3 to about 30 ng/mL, or any range derivable therein. In certain embodiments, BMP-4 is included in the differentiation medium at a concentration of about 0.1, about 0.3, about 1, about 5, about 10, about 15, about 20, about 25, about 30, about 40, about 50, about 100, about 300, or about 1,000 ng/mL. Some versions of the differentiation medium of the present invention include vascular endothelial growth factor (VEGF). VEGF is an important signaling protein that is involved in formation of the embryonic circulatory system and angiogenesis. VEGF can affect a variety of cell types including vascular endothelium and other cell types (e.g., neurons, cancer cells, kidney epithelial cells). In vitro, VEGF can stimulate endothelial cell mitogenesis and cell migration. VEGF function also has been shown to be important in a variety of disease states including cancer, diabetes, autoimmune diseases, and ocular vascular diseases. In the present system, VEGF increases definitive hematopoietic progenitor and HSC output. In certain embodiments, VEGF is included in a differentiation medium of the present invention at a concentration of from about 0.01 to about 100 ng/mL, from about 0.03 to about 30 ng/mL, from about 0.1 to about 10 ng/mL, from about 0.3 to about 3 ng/mL, or any range derivable therein. In certain embodiments, VEGF is included in the differentiation medium at a concentration of about 0.01, about 0.03, about 0.1, about 0.2, about 0.4, about 0.6, about 0.8, about 1, about 1.2, about 1.4, about 1.6, about 1.8, about 3, about 10, about 15, about 20, about 30, about 40, about 50, about 60, about 70, about 80, about 90, or about 100 ng/mL.

Some versions of the differentiation medium of the present invention include stem cell factor (also known as SCF, kit-ligand, KL, or steel factor). SCF is a cytokine that plays a role in hematopoiesis. SCF enhances survival, proliferation, and differentiation of hematopoietic stem cells and lineage-committed hematopoietic progenitor cells. In certain embodiments, SCF is included in a differentiation medium of the present invention at a concentration of from about 0.2 to about 2,000 ng/mL, from about 0.6 to about 600 ng/mL, from about 2 to about 200 ng/mL, from about 6 to about 60 ng/mL, or any range derivable therein. In certain embodiments, SCF is included in a differentiation medium of the present invention at a concentration of about 0.2, about 0.6, about 1, about 5, about 10, about 15, about 20, about 25, about 30, about 35, about 40, about 50, about 60 about 200, about 600, or about 2,000 ng/mL.

Some versions of the differentiation medium of the present invention include thrombopoietin (TPO). TPO is a lineage specific growth factor that plays a role in the proliferation and maturation of megakaryocytes. TPO regulates cell cycle inhibitors Cdkn1c (p57) and Cdkn2d (p19) and helps to maintain HSC quiescence. When included with SCF and FLT3, TPO may expand and differentiate HSCs and progenitors. In certain embodiments, TPO is included in a differentiation medium of the present invention at a concentration of from about 0.2 to about 2,000 ng/mL, from about 0.6 to about 600 ng/mL, from about 2 to about 200 ng/mL, from about 6 to about 60 ng/mL, or any range derivable therein. In certain embodiments, TPO is included in a differentiation medium of the present invention at a concentration of about 0.2, about 0.6, about 1, about 5, about 10, about 15, about 20, about 25, about 30, about 35, about 40, about 50, about 60 about 200, about 600, or about 2,000 ng/mL.

Some versions of the differentiation medium of the present invention include fms-related tyrosine kinase 3 ligand (FLT3). FLT3 aids in expansion and differentiation of HSCs. FLT3 synergizes with other factors and interleukins and regulates proliferation of early hematopoietic cells. In certain embodiments, FLT3 is included in a differentiation medium of the present invention at a concentration of from about 0.2 to about 2,000 ng/mL, from about 0.6 to about 600 ng/mL, from about 2 to about 200 ng/mL, from about 6 to about 60 ng/mL, or any range derivable therein. In certain embodiments, FLT3 is included in a differentiation medium of the present invention at a concentration of about 0.2, about 0.6, about 1, about 5, about 10, about 15, about 20, about 25, about 30, about 35, about 40, about 50, about 60, about 200, about 600, or about 2,000 ng/mL.

Some versions of the differentiation medium of the present invention include erythropoietin (EPO). EPO promotes erythrocyte formation and prevents apoptosis. EPO also promotes HSC maintenance. In certain embodiments, EPO is included in a differentiation medium of the present invention at a concentration of from about 0.2 to about 2,000 ng/mL, from about 0.6 to about 600 ng/mL, from about 2 to about 200 ng/mL, from about 6 to about 60 ng/mL, or any range derivable therein. In certain embodiments, EPO is included in a differentiation medium of the present invention at a concentration of about 0.2, about 0.6, about 1, about 5, about 10, about 15, about 20, about 25, about 30, about 35, about 40, about 50, about 60 about 200, about 600, or about 2,000 ng/mL. In some versions, high doses of thrombopoietin may be included in place of EPO.

Some versions of the differentiation medium of the present invention include transforming growth factor beta (TGFβ1). TGFβ1 increases HSC yield by increasing mesoderm specification, promotes HSC quiescence, upregulates p57 cyclin-dependent kinase inhibitor, modulates SMAD signaling induced by BMP4, and enhances total blood output. In certain embodiments, TGFβ1 is included in a differentiation medium of the present invention at a concentration of from about 0.05 to about 500 ng/mL, from about 0.15 to about 150 ng/mL, from about 0.5 to about 50 ng/mL, from about 1.5 to about 15 ng/mL, or any range derivable therein. In certain embodiments, TGFβ1 is included in a differentiation medium of the present invention at a concentration of about 0.05, about 0.15, about 0.5, about 1, about 2.5, about 5, about 7.5, about 10, about 15, about 20, about 30, about 40, about 50, about 100, about 150, or about 500 ng/mL.

Some versions of the differentiation medium of the present invention include rapamycin. Rapamycin is an inhibitor of the mTOR pathway. Rapamycin is a cell cycle inhibitor that induces HSC quiescence and limits proliferation and differentiation of the cells. As shown in FIGS. 3A-3D, rapamycin also increases yields of blood cells (CD45+, CD43+), HSCs (CD45+, CD43+, CD34+, CD38−, CD90+, CD45RA−), and myeloid progenitors differentiated from pluripotent stem cells. In certain embodiments, rapamycin is included in a differentiation medium of the present invention at a concentration of from about 1 to about 10,000 nM, from about 3 to about 3,000 nM, from about 10 to about 1,000 nM, from about 30 to about 300 nM, or any range derivable therein. In certain embodiments, rapamycin is included in the differentiation medium at a concentration of about 1, about 3, about 10, about 50, about 60, about 70, about 80, about 90, about 100, about 110, about 120, about 130, about 140, about 150, about 300, about 1,000, about 3,000 or about 10,000 nM. In some versions, other cell cycle inhibitors may be included in place of rapamycin or in addition to rapamycin at the above-described concentrations. Cell cycle inhibitors are well known in the art. See, e.g., Murphey et al. *Chem Biol Drug Des.*, 2006 68(4):213-9.

Some versions of the differentiation medium of the present invention include norepinephrine. Norepinephrine is a beta adrenergic receptor agonist. Norepinephrine can serve as a maturing signal for HSCs to respond to the sympathetic nervous system. In the media described herein, norepinephrine increases HSC output. In certain embodiments, norepinephrine is included in a differentiation medium of the present invention at a concentration of from about 3 to about 30,000 µM, from about 10 to about 10,000 µM, from about 30 to about 3,000 µM, from about 10 to about 1,000 µM, or any range derivable therein. In certain embodiments, norepinephrine is included in the differentiation medium at a concentration of about 1, about 3, about 10, about 50, about 100, about 200, about 250, about 300, about 350, about 400, about 500, about 1,000, about 10,000, or about 30,000 µM. In certain embodiments, norepinephrine is included in the differentiation medium at a concentration sufficient to increase the total number of cells derived from pluripotent stem cells exposed to the medium compared to the number of cells derived from pluripotent stem cells exposed to an identical differentiation medium lacking norepinephrine. In certain embodiments, norepinephrine is included in a differentiation medium of the present invention in an amount sufficient to increase the number and/or proportion of pluripotent stem cells differentiating to hematopoietic stem cells when exposed to the medium with respect to the number and/or proportion of pluripotent stem cells differentiating to hematopoietic stem cells when exposed to an identical differentiation medium lacking norepinephrine. In some versions, other beta adrenergic receptor agonists, such as epinephrine, salmeterol, and/or isoproterenol, may be included in place of norepinephrine or in addition to norepinephrine at the above-described concentrations.

Some versions of the differentiation medium of the present invention include LG101506. LG101506 is a selective RXR agonist that alters the cellular response to retinoic acid signaling by activating RXR PPARgamma, RXR PPARalpha, and RXR PPARdelta heterodimers. LG101506 increases the output of CD90+ HSCs generated from pluripotent stem cells, increases the number and proportion of CD38− cells, and enhances CFU cellularity and output. In certain embodiments, LG101506 is included in a differentiation medium of the present invention at a concentration of from about 0.01 to about 100 µM, from about 0.03 to about 30 µM, from about 0.1 to about 10 µM, from about 0.3 to about 3 µM, or any range derivable therein. In certain embodiments, LG101506 is included in the differentiation medium at a concentration of about 0.01, about 0.03, about 0.1, about 0.2, about 0.4, about 0.6, about 0.8, about 1, about 1.2, about 1.4, about 1.6, about 1.8, about 3, about 10, about 15, about 20, about 30, about 40, about 50, about 60, about 70, about 80, about 90, or about 100 µM. In certain embodiments, LG101506 is included in the differentiation medium at a concentration sufficient to increase the total number of cells derived from pluripotent stem cells exposed to the medium compared to the number of cells derived from pluripotent stem cells exposed to an identical differentiation medium lacking LG101506.

Some versions of the differentiation medium of the present invention include valproic acid. Valproic acid, a chromatin remodeler, is an inhibitor of histone deacetylases (HDAC) that affects chromatin remodeling by maintaining open chromatin. Valproic acid blocks HSC differentiation and promotes primitive HSC maintenance and repopulating ability. In the present system, valproic acid increases the proportion of CD34+, CD38− cells that are CD90+. In certain embodiments, valproic acid is included in a differentiation medium of the present invention at a concentration of from about 0.01 to about 100 mM, from about 0.03 to about 30 mM, from about 0.1 to about 10 mM, from about 0.3 to about 3 mM, or any range derivable therein. In certain embodiments, valproic acid is included in the differentiation medium at a concentration of about 0.01, about 0.03, about 0.1, about 0.2, about 0.4, about 0.6, about 0.8, about 1, about 1.2, about 1.4, about 1.6, about 1.8, about 3, about 10, about 15, about 20, about 30, about 40, about 50, about 60, about 70, about 80, about 90, or about 100 mM. In certain embodiments, valproic acid is included in the differentiation medium at a concentration sufficient to increase the total number of cells derived from pluripotent stem cells exposed to the medium compared to the number of cells derived from pluripotent stem cells exposed to an identical differentiation medium lacking valproic acid. In certain embodiments, valproic acid is included in a differentiation medium of the present invention in an amount sufficient to increase the number and/or proportion of pluripotent stem cells differentiating to hematopoietic stem cells when exposed to the medium with respect to the number and/or proportion of pluripotent stem cells differentiating to hematopoietic stem cells when exposed to an identical differentiation medium lacking valproic acid. In some versions, other chromatin remodelers, such as chlamodicin, sodium buterate, mocetinostat, NVP-LAQ824, Mi-2beta, inositol, vorinostat, may be included with or in place of valproic acid at the above-described concentrations.

Some versions of the differentiation medium of the present invention include Cripto. Cripto is a protein expressed in hypoxic endosteal niche cells. Cripto promotes primitive HSC development and regulates HSC quiescence. Cripto induces HSCs to respond as though they are in a hypoxic environment. In the present system, Cripto increases the size of CFU colonies. In certain embodiments, Cripto is included in a differentiation medium of the present invention at a concentration of from about 5 to about 50,000 ng/mL, from about 15 to about 15,000 ng/mL, from about 50 to about 5,000 ng/mL, from about 150 to about 1,500 ng/mL, or any range derivable therein. In certain embodiments, Cripto is included in a differentiation medium of the present invention at a concentration of about 5, about 15, about 50, about 100, about 200, about 300, about 400, about 500, about 600, about 700, about 800, about 900, about 1,000, about 1,500, about 5,000, about 15,000 ng/mL, or about 50,000 ng/mL.

Some versions of the differentiation medium of the present invention include the p38 mitogen-activated protein kinase (p38 MAPK) inhibitor LY2228820. LY2228820 indirectly inhibits NF-κB signaling, reduces cellular inflammation responses, and reduces cellular damage and stress. In the present system, LY2228820 results in an increase of the most primitive fraction of blood cells (CD90+) and increases CFU size. In certain embodiments, LY2228820 is included in a differentiation medium of the present invention at a concentration of from about 1 to about 10,000 nM, from about 3 to about 3,000 nM, from about 10 to about 1,000 nM, from about 30 to about 300 nM, or any range derivable therein. In certain embodiments, LY2228820 is included in the differentiation medium at a concentration of about 1, about 3, about 10, about 50, about 60, about 70, about 80, about 90, about 100, about 110, about 120, about 130, about 140, about 150, about 300, about 1,000, about 3,000 or about 10,000 nM. In certain embodiments, LY2228820 is included in the differentiation medium at a concentration sufficient to increase the total number of cells derived from pluripotent stem cells exposed to the medium compared to the number of cells derived from pluripotent stem cells exposed to an identical differentiation medium lacking LY2228820. In certain embodiments, LY2228820 is included in a differentiation medium of the present invention in an amount sufficient to increase the number and/or proportion of pluripotent stem cells differentiating to hematopoietic stem cells when exposed to the medium with respect to the number and/or proportion of pluripotent stem cells differentiating to hematopoietic stem cells when exposed to an identical differentiation medium lacking LY2228820. In some versions, other p38 MAPK inhibitors, such as SB 203580, BIRB 796 (Doramapimod), SB 202190, VX-702, VX-745, or PH-797804, may be included with or in place of LY2228820 at the above-described concentrations.

Some versions of the differentiation medium of the present invention include one or more antioxidants that protect against stress from reactive oxygen species. The inventors have found that simple culture differentiation of pluripotent cells results in many double strand (DS) DNA breaks, as marked by phosphorylated histone H2A variant gamma (gH2AX) staining. DS DNA breaks reduce transplant efficiency of repopulating HSCs. Inhibiting DNA damage of the DNA damage response resulting from reactive oxygen species or other sources of damage (radiation, chemical, etc.) in the present pluripotent differentiation system will increase hematopoietic cell number, repopulating ability, and cell differentiation potential. Preferred antioxidants that may be included in the medium of the present invention comprise ascorbic acid, NAC (N-Acetyl Cysteine), glutathione, sodium selenite, and butein, either alone or in combination.

In certain embodiments, sodium selenite is included in a differentiation medium of the present invention at a concentration of from about 1 to about 10,000 nM, from about 3 to about 3,000 nM, from about 10 to about 1,000 nM, from about 30 to about 300 nM, or any range derivable therein. In certain embodiments, sodium selenite is included in the differentiation medium at a concentration of about 1, about 3, about 10, about 50, about 60, about 70, about 80, about 90, about 100, about 110, about 120, about 130, about 140, about 150, about 300, about 1,000, about 3,000 or about 10,000 nM. In certain embodiments, sodium selenite is included in the differentiation medium at a concentration sufficient to increase the total number of cells derived from pluripotent stem cells exposed to the medium compared to the number of cells derived from pluripotent stem cells exposed to an identical differentiation medium lacking sodium selenite.

In certain embodiments, butein is included in a differentiation medium of the present invention at a concentration of from about 0.1 to about 1,000 µM, from about 0.3 to about 300 µM, from about 1 to about 100 µM, from about 3 to about 30 µM, or any range derivable therein. In certain embodiments, butein is included in the differentiation medium at a concentration of about 0.1, about 0.3, about 1, about 5, about 10, about 15, about 20, about 25, about 30, about 40, about 50, about 100, about 300, or about 1,000 µM. In certain embodiments, butein is included in the differentiation medium at a concentration sufficient to increase the total number of cells derived from pluripotent stem cells exposed to the medium compared to the number of cells derived from pluripotent stem cells exposed to an identical differentiation medium lacking butein.

In certain embodiments, NAC is included in a differentiation medium of the present invention at a concentration of from about 0.2 to about 2,000 mM, from about 0.6 to about 600 mM, from about 2 to about 200 mM, from about 6 to about 60 mM, or any range derivable therein. In certain embodiments, NAC is included in a differentiation medium of the present invention at a concentration of about 0.2, about 0.6, about 1, about 5, about 10, about 15, about 20, about 25, about 30, about 35, about 40, about 50, about 60 about 200, about 600, or about 2,000 mM.

In certain embodiments, ascorbic acid is included in a differentiation medium of the present invention at a concentration of from about 0.5 to about 5,000 ng/mL, from about 1.5 to about 1,500 ng/mL, from about 5 to about 500 ng/mL, from about 15 to about 150 ng/mL, or any range derivable therein. In certain embodiments, Cripto is included in a differentiation medium of the present invention at a concentration of about 0.5, about 1.5, about 5, about 10, about 20, about 30, about 40, about 50, about 60, about 70, about 80, about 90, about 100, about 150, about 500, about 1,500 ng/mL, or about 5,000 ng/mL. In certain versions, other reactive oxygen species may be included in place of ascorbic acid at the above-described concentrations. These include N-tert-butyl-α-phenylnitrone (PBN), 4-hydroxy-2,2,6,6-tetramethylpiperidine-1-oxyl (TEMPOL), diphenyliodonium (DPI), propyl gallate (PG), octyl gallate (OG), nordihydroguaiaretic acid (NDGA), tert-butylhydroquinone (TBHQ), ethoxyquin, 2,6-di-tert-butyl-4-hydroxymethylphenol (Ionox 100), or butylated hy-droxyanisole (BHA).

In certain embodiments, any one or combination of Cripto, LY2228820, valproic acid, sodium selenite, butein, or alternatives thereof are included in a differentiation medium of the present invention in an amount sufficient to increase the number and/or proportion of quiescent hematopoietic stem cells when exposed to the medium with respect to the number and/or proportion of quiescent hematopoietic stem cells when exposed to an identical differentiation medium lacking the any one or combination of Cripto, LY2228820, valproic acid, sodium selenite, butein, or alternatives thereof.

Some versions of the differentiation medium of the present invention include one or more agents that stimulate the prostaglandin $E_2$ pathway to promote HSC self-renewal and to increase RUNX1 expression. A preferred agent is prostaglandin $E_2$. In certain embodiments, prostaglandin $E_2$ is included in a differentiation medium of the present invention at a concentration of from about 0.02 to about 200 µM, from about 0.06 to about 60 µM, from about 0.2 to about 20 µM, from about 0.6 to about 6 µM, or any range derivable therein. In certain embodiments, prostaglandin $E_2$ is included in a differentiation medium of the present invention at a concentration of about 0.02, about 0.06, about 0.1, about 0.5, about 1, about 1.5, about 2, about 2.5, about 3, about 3.5, about 4, about 5, about 6 about 20, about 60, or about 200 µM. In certain versions, other agents that stimulate the prostaglandin $E_2$ pathway may be included in place of prostaglandin $E_2$ at the above-described concentrations. These include PGE2, PGI2, linoleic acid, 13(s)-HODE, LY171883, mead acid, eicosatrienoic acid, epoxyeicosatrienoic acid, ONO-259, Cay1039, 19(R)-hydroxy PGE2, 16,16-dimethyl PGE2 p-(p-acetamidobenzamido) phenyl ester, 11-deoxy-16,16-dimethyl PGE2, 9-deoxy-9-methylene-16,16-dimethyl PGE2, 9-deoxy-9-methylene PGE2, butaprost, sulprostone, PGE2 serinol amide, PGE2 methyl ester, 16-phenyl tetranor PGE2,15(S)-15-methyl PGE2, 15(R)-15-methyl PGE2, BIO, 8-bromo-cAMP, forskolin, bapta-AM, fendiline, nicardipine, nifedipine, pimozide, strophanthidin, lanatoside, L-Arg, sodium nitroprus side, sodium vanadate, bradykinin, mebeverine, flurandrenolide, atenolol, pindolol, gaboxadol, kynurenic acid, hydralazine, thiabendazole, bicuculline, vesamicol, peruvoside, imipramine, chlorpropamide, 1,5-pentamethylenetetrazole, 4-aminopyridine, diazoxide, benfotiamine, 12-methoxydodecenoic acid, N-formyl-Met-Leu-Phe, gallamine, IAA 94, and chlorotrianisene. See U.S. Pat. No. 8,168,428 to Zon et al.

Some versions of the differentiation medium of the present invention include an anti-inflammatory agent. Exemplary anti-inflammatory agents include p38 MAPK inhibitors, butein, and sodium selenite, among others, which can be included at the concentrations described above.

Other components that may be included in the media of the present invention include serum, a glutamine supplement, a sodium pyruvate supplement, a non-essential amino acid supplement, holo-transferrin, and a reducing agent. The serum may be fetal bovine serum, such as heat-inactivated fetal bovine serum. The serum may be included in a final amount of about 15% v/v. The glutamine supplement, sodium pyruvate supplement, and non-essential amino acid supplement may comprise any of such supplements known in the art. An exemplary glutamine source is Glutamax™ (Life Technologies, Carlsbad, Calif.), which may be added at 1× according to the manufacturer's instructions. The holo-transferrin may be included in an amount from about 2 μg/ml to about 20,000 μg/ml, such as about 2, 50, 100, 150, 200, 150, 300, 350, 400, 450 μg/ml or more. The reducing agent may include any reducing agent. Exemplary reducing agents are betamercaptoethanol and dithiothreitol.

The components described above are preferably included in a minimal essential medium. Many minimal essential media are well known in the art. The minimal essential media typically include glucose, amino acids, vitamins, inorganic salts, and other basic components to support cellular maintenance. Exemplary minimal essential media include Dulbecco's Modified Eagle Medium: Nutrient Mixture F-12 (DMEM/F-12) (Life Technologies, Carlsbad, Calif.), Iscove's Modified Dulbecco's Medium (IMDM) (Life Technologies, Carlsbad, Calif.), any of the various Ham's media, and alpha minimum essential medium, among others.

The differentiation medium of the present invention may include any one, all, or any combination or subcombination of the components described above, which are all available from commercial vendors. In certain embodiments, the differentiation medium of the present invention comprises a retinoic acid signaling inhibitor in combination with any one, all, or subcombinations of BMP4, VEGF, an antioxidant, a stimulant of the prostaglandin E2 pathway, TPO, SCF, FLT-3, EPO, TGFβ1, a p38 MAPK inhibitor, a beta adrenergic receptor agonist, a cell cycle inhibitor, an RXR agonist, a chromatin remodeler, and Cripto. In certain embodiments, the differentiation medium of the present invention comprises BMP4 in combination with any one, all, or subcombinations of a retinoic acid signaling inhibitor, VEGF, an antioxidant, a stimulant of the prostaglandin E2 pathway, TPO, SCF, FLT-3, EPO, TGFβ1, a p38 MAPK inhibitor, a beta adrenergic receptor agonist, a cell cycle inhibitor, an RXR agonist, a chromatin remodeler, and Cripto. In certain embodiments, the differentiation medium of the present invention comprises VEGF in combination with any one, all, or subcombinations of a retinoic acid signaling inhibitor, BMP4, an antioxidant, a stimulant of the prostaglandin E2 pathway, TPO, SCF, FLT-3, EPO, TGFβ1, a p38 MAPK inhibitor, a beta adrenergic receptor agonist, a cell cycle inhibitor, an RXR agonist, a chromatin remodeler, and Cripto. In certain embodiments, the differentiation medium of the present invention comprises an antioxidant in combination with any one, all, or subcombinations of a retinoic acid signaling inhibitor, BMP4, VEGF, an antioxidant, a stimulant of the prostaglandin E2 pathway, TPO, SCF, FLT-3, EPO, TGFβ1, a p38 MAPK inhibitor, a beta adrenergic receptor agonist, a cell cycle inhibitor, an RXR agonist, a chromatin remodeler, and Cripto. In certain embodiments, the differentiation medium of the present invention comprises a stimulant of the prostaglandin E2 pathway in combination with any one, all, or subcombinations of a retinoic acid signaling inhibitor, BMP4, VEGF, an antioxidant, TPO, SCF, FLT-3, EPO, TGFβ1, a p38 MAPK inhibitor, a beta adrenergic receptor agonist, a cell cycle inhibitor, an RXR agonist, a chromatin remodeler, and Cripto. In certain embodiments, the differentiation medium of the present invention comprises TPO in combination with any one, all, or subcombinations of a retinoic acid signaling inhibitor, BMP4, VEGF, an antioxidant, a stimulant of the prostaglandin E2 pathway, SCF, FLT-3, EPO, TGFβ1, a p38 MAPK inhibitor, a beta adrenergic receptor agonist, a cell cycle inhibitor, an RXR agonist, a chromatin remodeler, and Cripto. In certain embodiments, the differentiation medium of the present invention comprises SCF in combination with any one, all, or subcombinations of a retinoic acid signaling inhibitor, BMP4, VEGF, an antioxidant, a stimulant of the prostaglandin E2 pathway, TPO, FLT-3, EPO, TGFβ1, a p38 MAPK inhibitor, a beta adrenergic receptor agonist, a cell cycle inhibitor, an RXR agonist, a chromatin remodeler, and Cripto. In certain embodiments, the differentiation medium of the present invention comprises FLT-3 in combination with any one, all, or subcombinations of a retinoic acid signaling inhibitor, BMP4, VEGF, an antioxidant, a stimulant of the prostaglandin E2 pathway, TPO, SCF, EPO, TGFβ1, a p38 MAPK inhibitor, a beta adrenergic receptor agonist, a cell cycle inhibitor, an RXR agonist, a chromatin remodeler, and Cripto. In certain embodiments, the differentiation medium of the present invention comprises EPO in combination with any one, all, or subcombinations of a retinoic acid signaling inhibitor, BMP4, VEGF, an antioxidant, a stimulant of the prostaglandin E2 pathway, TPO, SCF, FLT-3, TGFβ1, a p38 MAPK inhibitor, a beta adrenergic receptor agonist, a cell cycle inhibitor, an RXR agonist, a chromatin remodeler, and Cripto. In certain embodiments, the differentiation medium of the present invention comprises TGFβ1 in combination with any one, all, or subcombinations of a retinoic acid signaling inhibitor, BMP4, VEGF, an antioxidant, a stimulant of the prostaglandin E2 pathway, TPO, SCF, FLT-3, EPO, a p38 MAPK inhibitor, a beta adrenergic receptor agonist, a cell cycle inhibitor, an RXR agonist, a chromatin remodeler, and Cripto. In certain embodiments, the differentiation medium of the present invention comprises a p38 MAPK inhibitor in combination with any one, all, or subcombinations of a retinoic acid signaling inhibitor, BMP4, VEGF, an antioxidant, a stimulant of the prostaglandin E2 pathway, TPO, SCF, FLT-3, EPO, TGFβ1, a beta adrenergic receptor agonist, a cell cycle inhibitor, an RXR agonist, a chromatin remodeler, and Cripto. In certain embodiments, the differentiation medium of the present invention comprises a beta adrenergic receptor agonist in combination with any one, all, or subcombinations of a retinoic acid signaling inhibitor, BMP4, VEGF, an antioxidant, a stimulant of the prostaglandin E2 pathway, TPO, SCF, FLT-3, EPO, a p38 MAPK inhibitor, TGFβ1, a cell cycle inhibitor, an RXR agonist, a chromatin remodeler, and Cripto. In certain embodiments, the differentiation medium of the present invention comprises a cell cycle inhibitor in combination with any one, all, or subcombinations of a retinoic acid signaling inhibitor, BMP4, VEGF, an antioxidant, a stimulant of the prostaglandin E2 pathway, TPO, SCF, FLT-3, EPO, a p38 MAPK inhibitor, TGFβ1, a beta adrenergic receptor agonist, an RXR agonist, a chromatin remodeler, and Cripto. In certain embodiments, the differentiation medium of the present invention comprises an RXR agonist in combination with any one, all, or subcombinations of a retinoic acid signaling inhibitor, BMP4, VEGF, an antioxidant, a stimulant of the prostaglandin E2 pathway, TPO, SCF, FLT-3, EPO, a p38 MAPK inhibitor, TGFβ1, a beta adrenergic receptor agonist, a cell cycle inhibitor, a chromatin remodeler, and Cripto. In certain embodiments, the differentiation medium of the present invention comprises a chromatin remodeler in combination with any one, all, or subcombinations of a retinoic acid signaling inhibitor, BMP4, VEGF, an antioxidant, a stimulant of the prostaglandin E2 pathway, TPO, SCF, FLT-3, EPO, a p38 MAPK inhibitor, TGFβ1, a beta adrenergic receptor agonist, a cell cycle inhibitor, an RXR agonist, and Cripto. In certain embodiments, the differentiation medium of the present invention comprises Cripto in combination with any one, all, or subcombinations of a retinoic acid signaling inhibitor, BMP4, VEGF, an antioxidant, a stimulant of the prostaglandin E2 pathway, TPO, SCF, FLT-3, EPO, a p38 MAPK inhibitor, TGFβ1, a beta adrenergic receptor agonist, a cell cycle inhibitor, an RXR agonist, and a chromatin remodeler. In these embodiments, the retinoic acid inhibitor may include any one, all, or any subcombinations of DEAB, disulfuram (tetraethylthiuram disulfide or bis(diethylthiocarbamyoyl)disulfide), retinoic acid receptor-β inhibitor LE135, the pan RA antagonist AGN 193109, and agonists of CYP26 or other molecules that aid in RA signaling inhibition or degradation. The antioxidant may include any one, all, or any subcombinations of sodium selenite, butein, N-acetyl cysteine, glutathione, and ascorbic acid. The chromatin remodeler may include any one, all, or any subcombinations of valproic acid, chlamodicin, sodium buterate, mocetinostat, NVP-LAQ824, Mi-2beta, inositol, and vorinostat. The stimulant of prostaglandin E2 pathway may include any one, all, or any subcombinations of prostaglandin E2, PGE2, PGI2, linoleic acid, 13(s)-HODE, LY171883, mead acid, eicosatrienoic acid, epoxyeicosatrienoic acid, ONO-259, Cay1039, 19(R)-hydroxy PGE2, 16,16-dimethyl PGE2 p-(p-acetamidobenzamido) phenyl ester, 11-deoxy-16,16-dimethyl PGE2, 9-deoxy-9-methylene-16,16-dimethyl PGE2, 9-deoxy-9-methylene PGE2, butaprost, sulprostone, PGE2 serinol amide, PGE2 methyl ester, 16-phenyl tetranor PGE2, 15(S)-15-methyl PGE2, 15(R)-15-methyl PGE2, BIO, 8-bromo-cAMP, forskolin, bapta-AM, fendiline, nicardipine, nifedipine, pimozide, strophanthidin, lanatoside, L-Arg, sodium nitroprusside, sodium vanadate, bradykinin, mebeverine, flurandrenolide, atenolol, pindolol, gaboxadol, kynurenic acid, hydralazine, thiabendazole, bicuculline, vesamicol, peruvoside, imipramine, chlorpropamide, 1,5-pentamethylenetetrazole, 4-aminopyridine, diazoxide, benfotiamine, 12-methoxydodecenoic acid, N-formyl-Met-Leu-Phe, gallamine, IAA 94, and chlorotrianisene. The p38 MAPK inhibitor may include any one, all, or any subcombinations of LY2228820 SB 203580, BIRB 796 (Doramapimod), SB 202190, VX-702, VX-745, and PH-797804. The beta adrenergic receptor agonist may include any one, all, or any subcombinations of norepinephrine, epinephrine, salmeterol, and isoproterenol.

One exemplary version of the differentiation medium of the present invention includes DMEM/F12, characterized FBS, Glutamax™ (100×), sodium pyruvate (100×), non-essential amino acids (100×), holo-transferrin, ascorbic acid, BME (1000×), $PGE_2$, TPO (human), SCF (human), FLT-3 (human), EPO, BMP4 (human), TGFb1 (human), VEGF (human), and DEAB. Another exemplary version includes a retinoic acid signaling inhibitor such as DEAB and/or an RXR agonist with BMP4. Another exemplary version includes BMP4 in combination with norepinephrine and/or in the presence of neural crest stem cells or their differentiation progeny. Another exemplary version includes one, all, or any subcombination of ascorbic acid, butein, sodium selenite, NAC (N-Acetyl Cysteine), and glutathione in combination with BMP4 and a retinoic acid signaling inhibitor such as DEAB. Another exemplary version includes an anti-inflammatory (p38 inhibitor, butein, and/or sodium selenite) with BMP4 and DEAB. Other exemplary versions are described in the Examples that follow.

In addition to the differentiation media, the invention also provides methods of generating a second type of cell from a first type of cell with the differentiation media described herein. The cells are preferably from mammalian origin and more preferably from human origin. One method comprises differentiating pluripotent stem cells into primitive blood cells. The pluripotent stem cells may comprise ES cells or iPS cells. The primitive blood cells may comprise parental cells of the blood cell lineage (e.g., CD45+, CD43+), hematopoietic progenitor cells (e.g., CD45+, CD43+, CD34+), and/or hematopoietic stem cells (e.g., CD45+, CD43+, CD34+, CD38−, CD90+, CD45RA−).

Some of the molecular pathways targeted by the compounds and their effects on developmental processes are conserved across species from zebrafish to frog to mammals and as such may have applications where cellular expansion of one type of cell in one species can be used and is ideal for production of biologically useful (including therapeutically useful) molecules or cells for similar or different species.

An exemplary method is shown in FIGS. 2A and B, wherein pluripotent stem cells (ES cells or iPS cells) are differentiated through mesoderm, lateral plate mesoderm, hematopoietic mesoderm, and hemogenic endothelium to form hematopoietic stem cells or hematopoietic progenitor cells. An advantage of the present invention is that a single differentiation medium as described herein can be used in differentiating pluripotent stem cells all the way to hematopoietic stem cells or hematopoietic progenitor cells without changing components thereof. Furthermore the invention described herein takes advantage of the broad function of RA inhibition to slow differentiation and proliferation, particularly of sensitive cell types such as HSCs, and also takes advantage of the broad role of reduced RA signaling in directed differentiation of cell types that are precursors of blood in the majority of developmental stages during embryonic development. The differentiation media can also be used in any substep between differentiating from pluripotent stem cells to hematopoietic stem cells or hematopoietic progenitor cells, such as differentiating mesoderm to lateral plate mesoderm, differentiating lateral plate mesoderm to hematopoietic mesoderm, differentiating hematopoietic mesoderm to aortic endothelium, etc.

As shown in FIGS. 2A and 2B, the exemplary method of differentiating pluripotent stem cells to hematopoietic stem cells or hematopoietic progenitor cells is carried out over a period of about 16 days or more. Human pluripotent stem cells are expanded in standard expansion conditions until large, undifferentiated colonies are present (compared to a size normally observed before a standard split). The colonies are maintained daily with standard stem cell expansion procedures. Differentiated colonies are marked and removed. Remaining colonies are then transferred to a dish (e.g., 10-cm dish) for EB suspension culture. Media used for this first step may be about 10 ml of EB media (DMEM/F12+ 15% heat-inactivated fetal bovine serum (hiFBS), 1× non-essential amino acids (NEAA), 1× Glutamax). This day of the experiment is referred to as Day 0. The following day (Day 1), the EBs are brought up from the suspension dish and washed in a fitting conical tube. They are returned to their dish with 10 ml fresh media composed of about 50% EB medium and 50% differentiation medium. The following day (Day 2), the procedure is repeated but with 100% differentiation medium. Thereafter, 50% of the media is replaced for each dish with fresh media every second day. At Day 8, the EBs are transferred from their suspension dish to Matrigel™ (BD Biosciences, San Diego, Calif., www.bdbiosciences.com) coated wells on a 6-well plate. Cystic EBs are a good sign but no guarantee for good EB quality in regard to final blood output. When the EBs are plated into the 6 wells, their total medium volume per well (2-3 ml) is preferably 50% old media and 50% fresh differentiation medium. Additional differentiation medium is added to each well (preferably 1 ml of additional fresh media) every second day until the endpoint of the protocol. The EBs will settle down on the surface of the wells and initiate rapid spread of endothelial-like cells into their surroundings. At Day 12, one can start to observe small round cells budding from certain endothelial spreads. These cells are likely to be the first emerging cells of hematopoietic potential. The cultures are preferably allowed to keep going until Day 16. At the last day of the protocol (preferably Day 16), the cultures are singularized, preferably by using TrypLE (Life Technologies, Carlsbad, Calif.), mechanical shearing, and cell filtration (30 micron). Once harvested, the cells are ready for analysis (FACS, CFU-assay, transplantation, or other methods of analysis or treatment). This exemplary method is provided only as an example and can be modified in a number of ways.

As described above, large, dense embryoid bodies (EBs) are preferably formed from the pluripotent stem cells prior to exposing the cells to the differentiation medium. Accordingly, the EBs are preferably formed for a period of at least about 6.5, about 7, about 7.5, about 8, or more days before exposing the EBs to the differentiation medium. The EBs initially exposed to the differentiation medium preferably are between about 0.5 mm and about 3 mm in diameter, such as between about 1 mm and 2 mm in diameter. The EBs initially exposed to the differentiation medium preferably are cystic, having "bubble"-like masses of cells protruding about the EB periphery. Although, it is initially preferred to expose EBs to the differentiation medium as described above, the invention also can be performed by initially exposing the differentiation medium to dispersed cells, dissociated cells, cell colonies, non-cystic EBs, or EBs having a diameter smaller than the ranges specified above.

The 50% EB medium and 50% differentiation medium used to culture the cells (e.g., EBs, etc.) at Day 0 may be called a "mixed medium," as opposed to a pure non-differentiation medium (e.g., EB medium) or a pure differentiation medium. The cells (e.g., EBs, etc.) may be cultured in the mixed medium for a period other than about 24 hours, such as a period ranging from about 12 to about 48 hours.

After replacing the mixed medium, it is preferred that fresh differentiation medium is added only to existing differentiation medium such that at no point after replacing the mixed medium is existing medium entirely removed from the cells. "Fresh medium" as used herein refers to medium that has not been exposed to cells intended to be differentiated. "Existing medium" as used herein refers to medium that has been exposed to cells being differentiated or intended to be differentiated for a period of at least about 15 minutes, 30 minutes, 1 hour, 2 hours, 6 hours, 12 hours, 18 hours, or 24 hours. The partial exchange of medium and addition of medium help to dilute toxic byproducts and replenish nutrients while maintaining possible unknown factors made by the cells that aid in the differentiation process. Although it is preferred that fresh differentiation medium is added only to existing differentiation medium after replacing the mixed medium, the invention also can be performed by entirely replacing the differentiation medium after replacing the mixed medium.

It is preferred that the cells are exposed to the differentiation medium for a period of at least about 5 days prior to plating the cells. The cells may be plated on any adherent surface. The surface may be a 2-dimensional surface or a 3-dimensional surface. The surface may be coated with one, all, or any combination of the components selected from the group consisting of BD Matrigel™ (BD Biosciences, San Diego, Calif., www.bdbiosciences.com) Geltrex® (Life Technologies, Carlsbad, Calif.), Laminin and/or its derivatives, Entactin (and its derivatives), vitronectin or one or more fragments or peptides of vitronectin (e.g., Vitronectin XF™ from Primorigen Biosciences, Madison, Wis., www.primorigen.com), collagen (one or more fractions I-IV), or synthetic or RGD-containing peptide coated surfaces (e.g., Synthemax® from Corning, Tewksbury, Mass.).

It is preferred that the cells are plated in the absence of feeder cells. However, the invention also may be performed by plating in the presence of feeder cells.

After plating, it is preferred that fresh volumes of the differentiation medium are added only to existing volumes of the differentiation medium without removing any of the existing volume of the differentiation medium. However, the invention also may be performed by completely replacing the existing volume of differentiation medium with a fresh volume of differentiation medium or by removing only some of the existing volume of differentiation medium.

In some versions of the invention, the cells are cultured in the presence of neural crest stem cells in addition to or as an alternative to exposing the cells to the differentiation medium. Neural crest stem cells and their progeny cells appear to provide multiple additional factors promoting the generation of HSCs (e.g., via cell contact, secreted factors, etc).

The method of differentiating cells described above may additionally comprise further differentiating the generated primitive hematopoietic cells into more highly differentiated blood cells. The more highly differentiated blood cells may include any differentiated blood cells described herein. Exemplary differentiated blood cells include any of the various types of myeloid cells and any of the various types of lymphoid cells. The primitive hematopoietic cells may be further differentiated in vitro or in vivo. In vitro methods of differentiating primitive hematopoietic blood cells are well known in the art. See, e.g., Charoudeh et al. Blood. 2010 Jul. 15; 116(2):183-92 for methods for differentiating primitive hematopoietic blood cells into lymphocytes. In addition, any methods currently used to differentiate cord blood cells can be used to further differentiate the primitive hematopoietic blood cells generated as described herein. In vivo methods of differentiating the primitive hematopoietic blood cells include administering the cells into the bloodstream of an animal, as occurs during engraftment with cord blood cells. The administered cells will differentiate into various forms within the animal.

Accordingly, and as described in further detail below, the invention also provides methods of engrafting a blood cell in an animal. The animal is preferably a human. The methods generally comprise administering a primitive hematopoietic stem cell generated by the methods described herein or a cell differentiated therefrom to the animal. Methods of engraftment are described in U.S. Pat. No. 8,168,428 to Zon et al. In some versions, the animal is a candidate for bone marrow or stem cell transplantation, or an animal that has received bone marrow ablating chemotherapy or irradiation therapy.

The differentiation media, the differentiation methods, and the cells generated therewith may be used in any of a number of embodiments.

One embodiment comprises differentiating pluripotent stem cells (ES or iPS) to a definitive HSC phenotype (CD45+, CD43+, CD34+, CD38−, CD90+, CD45RA−) with lymphoid and myeloid differentiation capacity for research and therapeutic purposes.

Another embodiment comprises using such cells for in vitro studies of hematological diseases. This may comprise further differentiating the HSC phenotype cells as produced herein, themselves differentiated from pluripotent stem cells, into various terminal blood cells and used to build assays for the disease or to identify drugs and medicines to treat such diseases. For example, in certain osteoporosis diseases, iPS cells generated from a patient can be used to generate HSCs and then principle blood components therefrom. See, e.g., Example 5. One can then identify reduced macrophage function as a surrogate for the disease. One can further devise treatments for the disease using the cells produced herein or derived from the cells produced herein to identify gene therapy based treatments to restore macrophage function and ameliorate the manifestations of the disease.

In another embodiment, in vitro studies of developmental hematopoiesis can be performed by investigating the precursors to the HSCs generated with the methods described herein. Such precursors can be used to identify developmental factors that influence the cells toward a particular cell type or other condition of interest. For example, one could explore potential molecules and other treatments to study posterior lateral plate mesoderm formation by looking at markers of FOXC1, FOXF1, SALL1, or others, as described herein.

In another embodiment, in vitro studies of hematopoietic stress responses can be performed by focusing on the most primitive hematopoietic cells resulting from the invention described herein. For example, using p38, a molecule that reduces NFKb signaling and inflammation responses, can increase HSC output. See Example 1 for an example of a screen that can be used in such a study.

In another embodiment, in vivo zenograft studies can be performed using cells produced from the methods described herein to better evaluate disease cells and genetically corrected disease cells. Such studies can also be performed to assess compounds applied to the disease cells or to the animal itself for their ability to correct the disease phenotype when the animal is administered the HSCs or progenitors produced as described herein.

In another embodiment, HSCs produced in vitro from pluripotent stem cells using the methods described herein can also be used to evaluate, screen, and identify additional novel factors to generate definitive HSCs with clinically relevant transplantation potential.

In another embodiment, patients with hematological disease, or disease where blood cell transfusion can alleviate, reduce, or abrogate symptoms, can be transfused with the HSCs or progenitors produced as described herein. For example, patient-derived iPS cells from a patient suffering from sickle cell anemia can be used to produce HSCs and progenitors using the invention described herein and can be further differentiated into erythrocytes (following genetic correction at some point whether prior to iPS generation, at the iPS stage, or downstream of the iPS) to treat the sickle cell anemia.

In another embodiment, HSCs or progenitors produced according to the methods described herein can be used to produce granulocytes and macrophages for therapeutic purposes. For example, HSCs and progenitors produced using the invention described herein can be differentiated further into neutrophils, eosinophils, monoblasts, myeloblasts, macrophages, or megakaryocytes (for platelet production). These terminal cells can be transplanted into a patient or otherwise used for therapeutic purposes. Alternatively, patient iPS-derived HSCs produced according to the methods described herein can be transplanted (following genetic correction at some point whether prior to iPS generation, at the iPS stage, or downstream of the iPS) into chronic granulomatous disease patients. Alternatively, myeloid progenitors or their progeny (mature macrophages and granulocytes) derived from progenitors and HSCs differentiated from pluripotent stem cells using the invention described herein can be transfused into these patients to treat the disease.

In another embodiment, HSCs and progenitors produced from pluripotent stem cells using the invention described herein can be further differentiated into B, T, and NK (lymphoid cells), and these terminally differentiated cells can then be transplanted into a human in order to treat symptoms of a disease resulting from abnormalities in their in vivo lymphoid cell production systems.

In another embodiment, T-cells generated from progenitors or HSCs differentiated from pluripotent stem cells according to the invention described herein can be engineered at either the iPS cell stage or later in differentiation to have anti-tumor activity by selectively targeting the tumor for destruction by immune cells initiated by T-cell anti-tumor response. T-cells can be engineered to specifically target epitopes uniquely expressed on tumor cells as reported in Morgan et al., *Human Gene Therapy*. October 2012, 23(10): 1043-1053.

In another embodiment, HSCs and progenitors produced from patient-derived pluripotent stem cells according to the invention described herein can be used directly for drug screens to identify promising drug candidates for treating hematological diseases. Additionally, HSCs and progenitors produced from pluripotent stem cells according to the invention described herein can be further differentiated using many different methods into terminal blood cell types. The terminally differentiated cells can then be used to construct and conduct drug screens to identify promising drug candidates for treatment of the various hematological diseases. For example, large numbers of helper t1 (Th1) cells and helper t2 (Th2) cells can be derived from progenitors and HSCs produced from pluripotent stem cells according to the invention described herein. The cells can then be immobilized in a high throughput surface, such as a 96-well or 384-well microtiter plate coated with a supportive coating and immersed in a medium supporting the Th1 and Th 2 cells. The Th1 and Th2 cells can then be used to screen drug candidates for the ability to modulate the immune responses facilitated or generated from Th1 and Th2 cells. For example, libraries of compounds could be added to the wells containing the Th1 and/or Th2 cells and after an appropriate incubation time, any number of outputs could be measured using fluorescence, chemiluminesence, or other enzymatic or other methods to record the output and thus identify the effect of the compound on Th1 and/or Th2 cell activity. A further example would be using the Th1 and Th2 cells derived as described herein to screen derivatives of prostaglandins for their ability to effect production of cytokines such as interleukin-2 (IL-2), IL-4, IL-5, and Interferon Gamma and others.

There are approximately 120 hematological disorders, all of which could benefit from HSCs and progenitors differentiated from pluripotent stem cells according to the invention described herein. These progenitors and HSCs differentiated from pluripotent stem cells according to the invention described herein could be used directly to treat these diseases following proper conditioning of the patient or further differentiated into the terminal cell directly affected in the particular disease and delivered to the patient who had a deficiency or defect in a particular terminal cell type. For example, X-Linked severe combined immunodeficiency disease patients are missing entire lymphoid lineages (B cells, T cells, NK cells). Transplanting these patients with progenitors and/or HSCs differentiated from pluripotent stem cells according to the invention described herein or with terminal B cells, T cells, NK cells further differentiated from progenitors and HSCs differentiated from pluripotent stem cells according to the invention described herein with the corrected gene could restore lineage function to these patients. For example, transplanting the patients suffering from diamond blackfan anemia (red cell deficiency) with progenitors and/or HSCs differentiated from pluripotent stem cells according to the invention described herein, with erythroid progenitors derived from progenitors and HSCs differentiated from pluripotent stem cells according to the invention described herein, or with terminal red blood cells (erythrocytes) cells further differentiated from progenitors and HSCs differentiated from pluripotent stem cells according to the invention described herein could provide a significant treatment for these patients.

In another embodiment, HSCs, progenitors or mature blood cells produced from pluripotent stem cells according to the invention described herein can be used to provide therapeutic factors generated within the cells following genetic manipulation of the cells for treating non-hematological diseases. For example, blood cells generated from pluripotent stem cells can be modified to overexpress clotting factor genes (Factor IX) and transplanted/transfused into hemophilia patients. These clotting factors normally are produced in the liver but could be produced in blood cells allowing for systemic delivery of therapeutic proteins and factors.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Materials and Methods

Overview

Human ES cell lines and iPS cell lines were differentiated towards the blood lineage using modified version of a previously described protocol (Woods et al. *Stem Cells*, 2011, 29(7):1158-1164). The modifications, which improved the efficiency of blood cell output, are described as follows.

For embryoid body (EB) formation, pluripotent stem cell colonies were cultured an additional 24 hours to increase colony cell density. During the EB formation stage following pluripotent stem cell colony peeling, the suspension culture was extended to 8 days with a 1.5-fold increase in media volume. A low-adherence, round 10-cm dish was used in place of low-adherence T25 flasks. The round dish prevents the accumulation of EBs in corners and reduces EB aggregation that reduces blood cell output. Together, these modifications allow for a 3-fold increase number of EBs generated per square cm.

For the adherence plating of the EBs for endothelial and hematopoietic cell expansion, the murine OP9 feeder layer was replaced with Matrigel™ (RD Biosciences, San Diego, Calif., www.bdbiosciences.com) or Vitronectin XF™ (Primorigen Biosciences, Madison, Wis., www.primorigen-.com), both of which increased hematopoietic cell output and increased primitive cell output with an HSC phenotype. Differentiation Medium 1 (defined below) was used continuously throughout the protocol and was not changed to a hematopoietic expansion media during the last week. Differentiation Medium 1 was added every second day to the adherent EB wells and none was removed to reduce dilution of secreted factors from the cultured cells. The duration of the protocol was reduced to a total of 16 days by removing the final 5 days of the published protocol.

DEAB was used throughout the differentiation protocol at various concentrations. DEAB was found to maintain cells with an HSC phenotype by increasing the numbers of cells with a capacity for both lymphoid and myeloid differentiation capacity, to increase mesodermal precursors of blood during the differentiation process, and to block endoderm and cardiac mesoderm cell lineage specification. The long duration of the protocol and the ability to generate both lymphoid and myeloid cells, including erythrocytes with beta hemoglobin, indicate that the protocol is capable of generating definitive hematopoietic cells.

Additional factors intended to influence mesoderm cell expansion and differentiation, hemogenic endothelial cell propagation, and hematopoietic cell expansion (including primitive and definitive hematopoietic), self-renewal, and maintenance were applied to the DEAB-containing Differentiation Medium 1 medium individually at varying concentrations and times during the differentiation protocol. Results were analyzed to determine additional molecules that increased further the yield of progenitors and phenotypic stem cells in our differentiation system.

The resulting protocol is described in detail as follows.

Pluripotent Stem Cell Validation and Culture

Human ES cell lines and iPS cell lines that were karyotypically normal and shown to be pluripotent by in vivo teratoma histological assays and polymerase chain reaction (PCR) were obtained. The pluripotent cell lines were cultured and expanded using either Matrigel™ (BD Biosciences, San Diego, Calif.) or murine embryonic fibroblast feeder cells in stem cell media (mTeSR1 or DMEM/F12 media, respectively) containing FGfb to maintain pluripotency.

Embryoid Body Formation

Embryoid bodies (EBs) were generated from ES cells or iPS cells grown on mouse embryonic fibroblasts or Matrigel-coated 10-cm dishes for 8 days, so that colonies appeared large and dense. Colonies were separated from the plate with 4 ml of dispase (0.5 mg/ml, Life Technologies, Carlsbad, Calif., www.lifetechnologies.com) for 30-45 minutes. Colonies were collected in EB medium (Iscove's modified Dulbecco's medium supplemented with 15% fetal bovine serum (FBS) Scientific Hyclone, Rockford, Ill., www.thermoscientific.com), 1% nonessential amino acids (Life Technologies, Carlsbad Calif.), and 1% GlutaMax (Life Technologies, Carlsbad Calif.), allowed to settle at the bottom of a 15-ml conical tube, rinsed twice with EB medium, and placed in a non-adherent round dish in EB medium overnight.

Mesoderm Generation with Posterior Lateral Plate Mesoderm Specification

Early stage EB colonies (at 24 hours) were then cultured in mesoderm-specifying Differentiation Medium 1 (described below) for a total of 8 days with partial medium changes made every other day. Cells were harvested at day 0, 4 and 8 for RT-PCR analysis of marker genes of mesoderm lineage development.

Differentiation Medium 1 is composed of Dulbecco's modified Eagle medium/F12 supplemented with batch selected FBS 15%, 10 ng/ml bone morphogenetic protein 4 (BMP4), 5 ng/ml transforming growth factor beta 1 (TGFb1), 1 ng/ml vascular endothelial growth factor (VEGF), 20 ng/ml thrombopoietin (TPO), 20 ng/ml erythropoietin (EPO), 20 ng/ml stem cell factor (SCF), 20 ng/ml FMS-like tyrosine kinase 3 ligand (FLT3L), 200 µg/ml holotransferrin, 2 µM prostaglandin E2 (PGE2), 50 µg/ml ascorbic acid, and 10 M DEAB. Differentiation Medium 1 includes DEAB except when explicitly indicated otherwise. The components in Differentiation Medium 1 were obtained from commercial vendors. EB plating on Extra Cellular Matrix for Definitive Hematopoietic Cell Generation and Expansion Whole, day 8 EBs were then plated on growth factor reduced Matrigel™ (BD Biosciences)-coated six-well plates. The mesoderm-specifying medium (Differentiation Medium 1) was added every other day until day 16 (termination of the blood generation protocol) without removal of the conditioned media.

Analysis by Flow Cytometry

Cells from the differentiation cultures were collected at time points indicated and washed in phosphate-buffered saline (PBS) supplemented with 2% FBS. Adherent cells were individualized using TrypLE (Life Technologies, Carlsbad Calif.), passed through a 27.5-gauge needle and filtered through a 40-70 µm cell strainer (BD Falcon, San Diego, Calif., www.bdbiosciences.com). Cells were treated with 7-aminoactinomycin D (7AAD) before analysis, and positive cells were gated out of results. Cells were stained with fluorescence-conjugated antibodies for the hematopoietic stem and progenitor cell markers CD45, CD43, CD34, CD38, CD90; CD45RA. Cells were analyzed on a FACS Canto (BD, Franklin Lakes, N.J., www.bd.com).

Hematopoietic Progenitor Cell Differentiation Assays

The differentiation cultures were trypsinized at the indicated time points and single-cell suspensions were generated following trypsinization. For the Colony Forming Unit (CFU) assays using methyl cellulose cultures, 25% of the cells were plated in 2 ml of MethoCult H4435 (STEMCELL Technologies, Vancouver, BC) in six-well plates. Alternatively, sorted CD45+, CD43+, CD34+, 7AAD-cells were sorted and plated at 500 cells per 2 ml Methocult media. Cells were incubated for 14 days in a humidified incubator at 37° C. with 5% $CO_2$ and evaluated for colonies by bright-field microscopy (Zeiss (Oberkochen, Germany, www.zeiss.com) Axiovert 200 with a Zeiss Axiocam), Cells were resuspended in PBS supplemented with 2% FBS. For the lymphoid myeloid differentiation assays, either CD45+, CD43+, CD34+, 7AAD-hematopoietic progenitors, or CD45+, CD43+, CD34+, CD38-, CD90+, CD45RA- phenotypic HSCs were plated at 20-40 cells per well onto OP9 and OP9delta feeder lines for B-cell and T-cell differentiation, respectively, as previously described (Nozad Charoudeh H, Tang Y, Cheng M, Cilio C M, Jacobsen S E, Sitnicka E., Identification of an NK/T cell-restricted progenitor in adult bone marrow contributing to bone marrow- and thymic-dependent NK cell, *Blood,* 2010 Jul. 15; 116(2):183-92. NK cell differentiation as well as myeloid cell differentiation was also detected in this differentiation system. FACS analysis was performed 4-6 weeks after plating for markers of lymphoid cell differentiation with the markers indicated. Similar cell sortings were performed for single cell Terasaki plate assays of myeloid differentiation and expansion using StemSpan media (STEMCELL Technologies, Vancouver, BC) supplemented with TPO, SCF, FLT3, IL3, GM-CSF. Colony size was estimated by microscopy.

Mesoderm Gene Expression Analysis

RNA from the pluripotent stem cell differentiation cultures was harvested at multiple time points corresponding to stages of development from pluripotent stem cells to hematopoietic lineages during in vitro culture. Cells were lysed using Trizol (Life Technologies, Carlsbad Calif.), and RNA was isolated according to the manufacturer's specifications. A cDNA library was reverse transcribed by the High Capacity RNA-to-cDNA Kit from Applied Biosystems (Life Technologies, Carlsbad, Calif.). PCR products were amplified for 40 cycles using primers designed for the gene of interest.

Quantitative Analysis of Cell Numbers and Statistical Analyses

Cells were counted using the FACS cell counter feature (BD) or by cytometer using a bright-field microscope to obtain viable cell numbers. The total numbers of cells of each subpopulation were calculated by multiplying the number of cells by the proportion of cells of that lineage as determined by flow cytometry. Statistical analyses of data points and error bars of this study show mean and standard deviation, with statistical significance assessed by the Student's t-test.

Pluripotent Stem Cell Derived Hematopoietic Cell Transplantation Assays

Single-cell suspensions of the pluripotent stem cell differentiation cultures described herein were injected into sublethally irradiated (325 rad) NOD.Cg-Prkdc$^{scid}$Il2rg$^{tm1Wjl}$/SzJ mice (JAX, Bar Harbor, Me., www.jax.org) via tail vein injections, intrafemoral injection, or cardiac injection. Peripheral blood was harvested at times indicated via tail vein or retro-orbital eye bleed or cardiac puncture on anesthetized mice. Bone marrow and spleen cells were harvested at the terminal stage of the transplant experiment. Bone marrow cells were isolated via pestle mortar crushing of bone followed by rinsing and 70 micron filtering. Cells were analyzed by FACS, CFU assay, or transplanted serially into secondary and tertiary mice. FACS analysis for the human pan hematopoietic marker CD45, progenitor marker CD34, myeloid markers CD11b, CD15, CD33 and lymphoid markers CD19, CD56 and CD132, and erythroid markers CD235. When erythrocytes were not being analyzed, the red cells were lysed using ammonium chloride solution (0.8% $NH_4Cl$ with 0.1 mM EDTA) (STEMCELL Technologies, Vancouver, BC), spun, and stained with antibodies against the above-mentioned markers. All animal experiments were conducted in accordance with Institutional Animal ethical use protocols.

Example 1

Small Molecule Screen

Figure 3A:
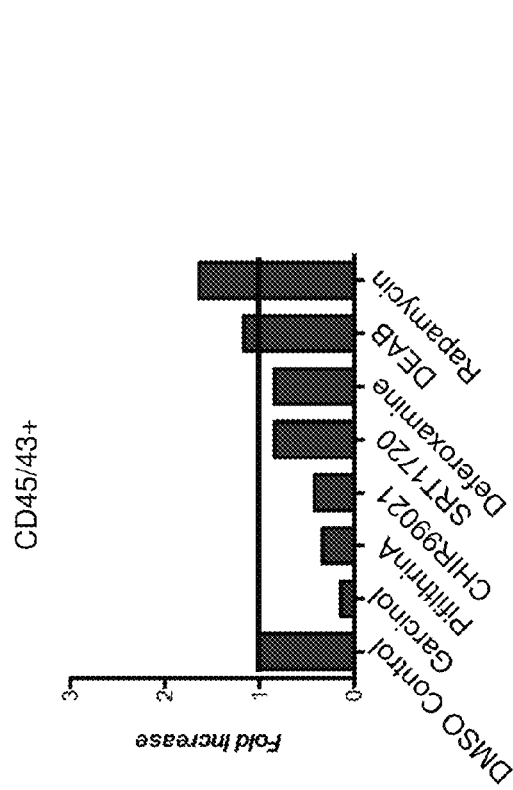
FIGS. 3A-C depicts results of a small molecule screen to identify compounds that improve the output of phenotypic hematopoietic stem cells and hematopoietic progenitor cells.
Figure 3B:
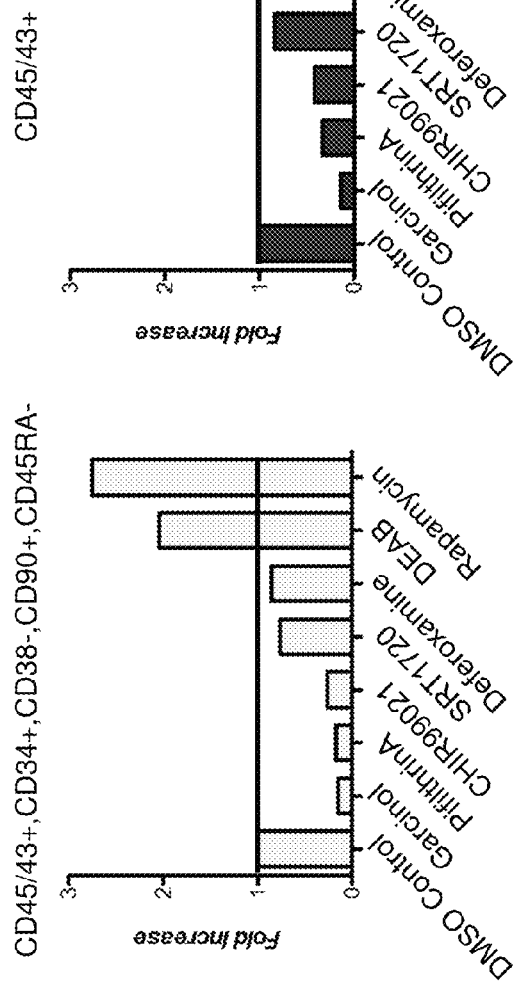
Figure 3C:
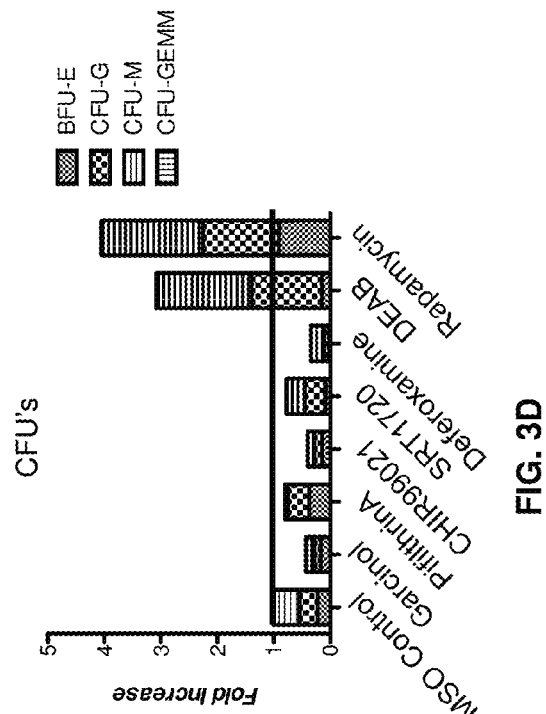
Figure 3D:
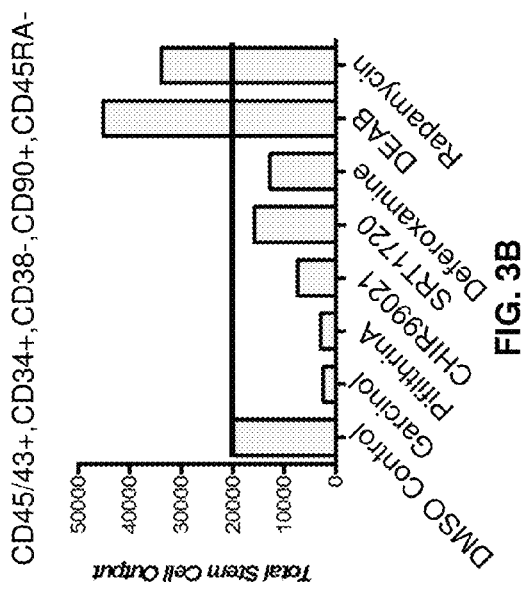
FIG. 3D shows the fold increase in the colony/burst forming units (CFU/BFU) of myeloid hematopoietic progenitors for each screened compound relative to a DMSO control, depicting in detail the changes in erythroid burst-forming units (BFU-E), granulocyte colony-forming units (CFU-G), macrophage colony-forming units (CFU-M), and multi-potential granulocyte, erythroid, macrophage, megakaryocyte colony-forming units (CFU-GEMM).

A small molecule screen was performed to identify compounds that improve the output of hematopoietic progenitor cells (HPCs; CD45+, CD43+, CD34+) and phenotypic hematopoietic stem cells (HSCs; CD45+, CD43+, CD34+, CD38−, CD90+, CD45RA−) differentiated from pluripotent stem cells. Molecules targeting pathways known or suspected of being important in hematopoiesis were screened. The screened molecules included garcinol (10 µM), a histone acetyltransferases (HATs) inhibitor; pifithrinA (10 µM), a p53 tumor suppressor protein inhibitor, to minimize DNA damage from oxidative stress; CHIR99021 (1 µM), a GSK3 inhibitor, to activate the Wnt pathway for enhancing specification of lateral plate mesoderm to posterior lateral plate mesoderm; SRT1720 (1 µM), an activator or enhancer of SIRT1 enzymatic efficiency; deferoxamine (1 µM), an inducer of hypoxia-like responses in cells through induction/activation of HIF-1a; diethylaminobenzaldehyde (DEAB; 10 µM), a retinoic acid synthesis or accumulation inhibitor; and rapamycin (0.1 µM), an inhibitor or silencer of the mTOR pathway. Each of the above molecules was added to a base medium essentially as published in Woods et al. *Stem Cells*, 2011, 29(7):1158-1164 at the above-described final concentrations and used to differentiate ES and iPS cells. Cells were analyzed using fluorescence activated cell sorting (FACS; FIGS. 3A, 3B, and 3C) and CFU-GEMM assays (FIG. 3D). As shown in FIGS. 3A-D, both DEAB and rapamycin increased the output of total blood cells (CD45+, CD43+; FIG. 3C), HSCs (FIGS. 3A and B), and myeloid progenitors (FIG. 3D).

Example 2

Effects of DEAB

From Example 1, DEAB was selected to move forward into an experiment further establishing the phenotypes of blood cells emerging from the differentiation in order to identify at what stage of differentiation DEAB may exert its effects. Pluripotent stem cells (iPS and ES) were grown and induced to produce embryoid bodies on Day 8 as described. The EBs were then exposed to Differentiation Medium 1 for a total of 8 days with partial medium changes made every other day as described. Cells were harvested on Day 16 and washed in phosphate-buffered saline (PBS) supplemented with 2% FBS. Adherent cells were individualized using TrypLE (Life Technologies, Carlsbad Calif.), passed through a 27.5-gauge needle and filtered through a 40-70 µm cell strainer (BD Falcon, San Diego, Calif., www.bdbiosciences.com). Cells were treated with 7-aminoactinomycin D before analysis and positive cells were gated out of results. Cells were stained with fluorescence conjugated antibodies for the hematopoietic stem and progenitor cell markers CD45, CD43, CD34, CD38, CD90, CD45RA. Cells were analyzed on an FACS Canto (BD, Franklin Lakes, N.J., www.bd.com).

Figures 4A, 4B:
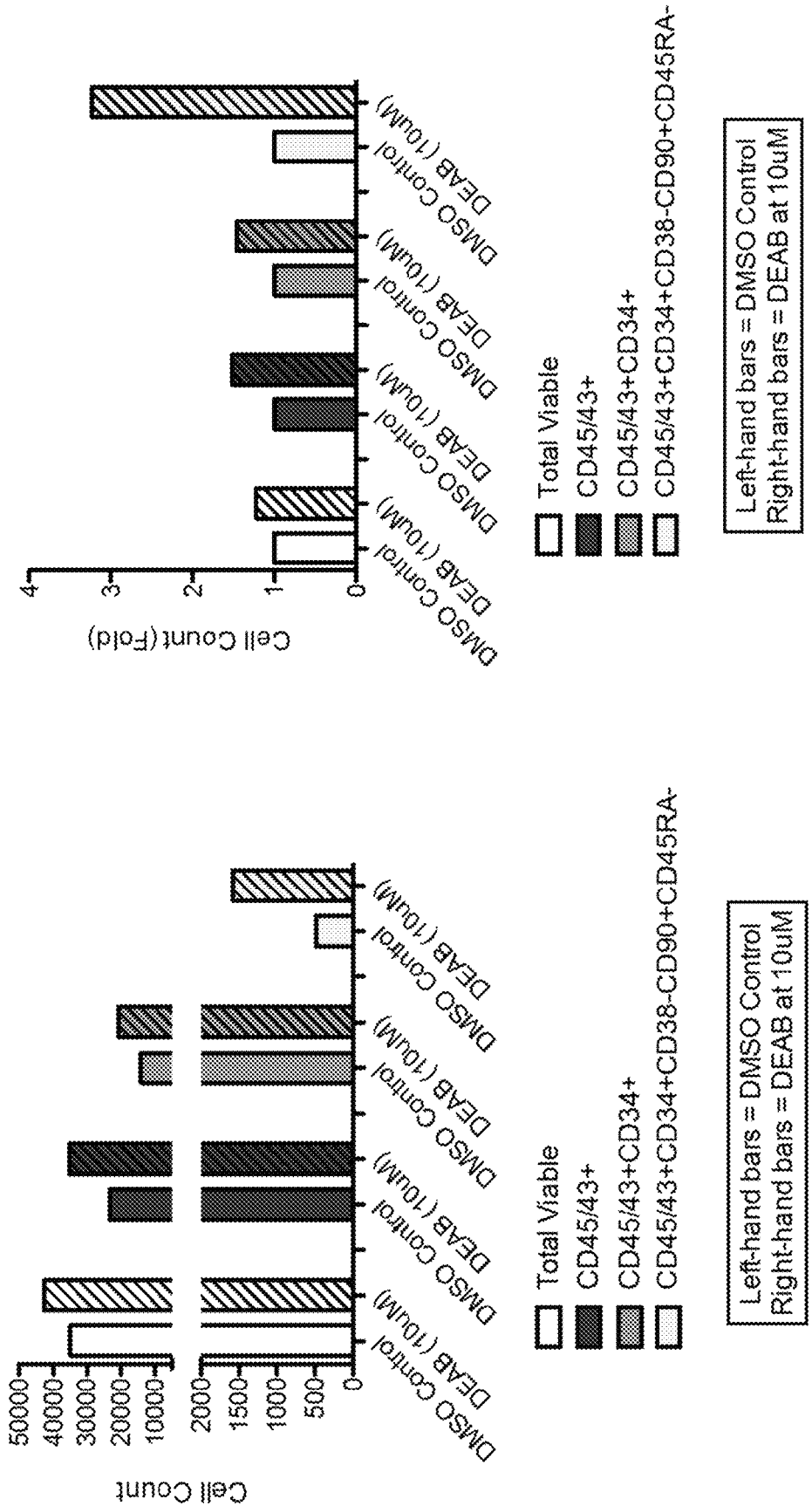

Results are presented in FIG. 4A (total cell counts), FIG. 4B (fold change in total cell counts), FIG. 3C (percentage of harvested cells expressing these markers), and FIG. 4D (fold change in total cell percentages expressing these markers). Taken together, these results show that presence of DEAB at 10 uM results in modestly higher values of total viable cells, blood cells (CD45+, CD43+), hematopoietic progenitor cells (CD45+, CD43+, CD34+), and substantial improvement in the population of cells exhibiting a hematopoietic stem cell phenotype (CD45+, CD43+, CD34+, CD38−, CD90+, CD45RA−). Collectively these data show that DEAB when used in this differentiation system exerts an effect on increasing the generation of the most primitive cells (FIGS. 4A and 4C), with generation of the phenotypic stem cell phenotype increasing over 3-fold (FIGS. 4B and 4D).

Example 3

CFU Results with DEAB

For the Colony Forming Unit (CFU) assays using methyl cellulose cultures, 25% of the cells harvested for Example 2 were plated into in 2 ml of MethoCult H4435 (STEMCELL Technologies, Vancouver, BC) in six-well plates. Alternatively, sorted CD45+, CD43+, CD34+, 7AAD-cells were sorted and plated at 500 cells per 2 ml MethoCult media. Cells were incubated for 14 days in a humidified incubator at 37° C. with 5% $CO_2$ and evaluated for colonies by bright-field microscopy (Zeiss, Oberkochen, Germany, www.zeiss.com) Axiovert 200 with a Zeiss Axiocam).

Figure 5:
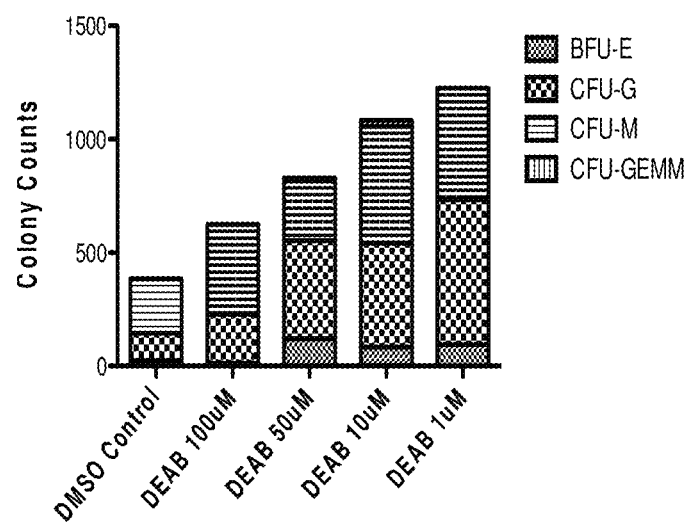
FIG. 5 depicts an increase in colony counts of hematopoietic progenitor cells differentiated from iPS cells in media containing increasing concentrations of DEAB, depicting in detail the changes in erythroid burst-forming units (BFU-E), granulocyte colony-forming units (CFU-G), macrophage colony-forming units (CFU-M), and multi-potential granulocyte, erythroid, macrophage, megakaryocyte colony-forming units (CFU-GEMM).

The results of this experiment are shown in FIG. 5. The data show that 10 UM DEAB enables measurable levels of all four major CFU assay types (CFU-G, CFU-M, CFU-GEMM, BFU-E to be obtained and that the total number of colonies counted in the assay more than double the number of colonies obtained from identical assay when using cells not differentiated in the presence of DEAB (DMSO control).

Example 4

Gene Expression Results

Gene expression studies were carried out to determine expression of key genes for the major divergences in the pathway from iPS to HSC. Briefly, RNA from the differentiation cultures was harvested at multiple time points (Day 0, 4, 8, 12, 15), corresponding to stages of development during in vitro culture and differentiation of pluripotent stem cells to hematopoietic lineages using Differentiation Medium 1. Cells were lysed using Trizol (Life Technologies, Carlsbad Calif.) and RNA was isolated according to manufacturer's specifications. A cDNA library was reverse transcribed using the RNA-to-cDNA Kit from Applied Biosystems (Life Technologies, Carlscad, Calif.). PCR products were amplified using appropriate primers designed for the genes of interest for 40 cycles.

To understand how RA-signaling inhibition with DEAB may lead to increased output of the most primitive blood cells (phenotypic HSCs: CD45+, CD43+, CD34+, CD38−, CD90+, CD45RA−) from pluripotent stem cells without an increase in the total blood (mature cells and progenitors), we performed quantitative gene expression analyses for key development markers at various time points during the differentiation protocol. As the developmental marker genes we surveyed are not known to be direct targets of RA signaling, we can expect the marker gene expression levels to correlate to the cell numbers in culture.

Figure 6A:
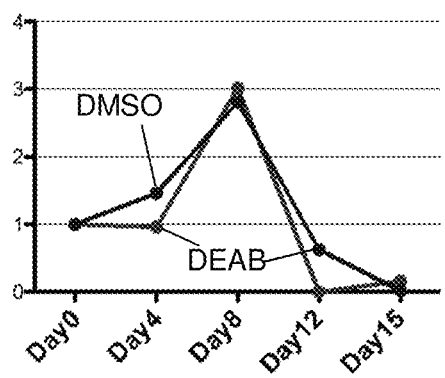
FIGS. 6A-P depict changes in gene expression at days 0, 4, 8, 12, and 15 of differentiation of pluripotent stem cells to hematopoietic lineages in the presence of DEAB in accordance with a method of the present invention.
Figure 6B:
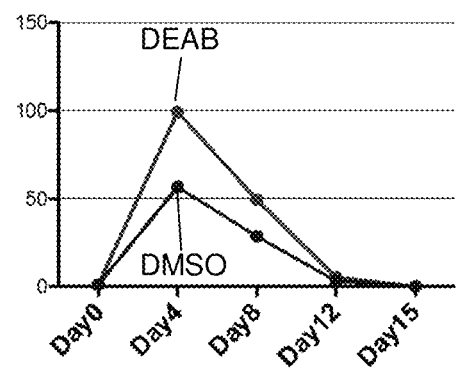
FIG. 6B shows expression of Brachyury.
Figure 6C:
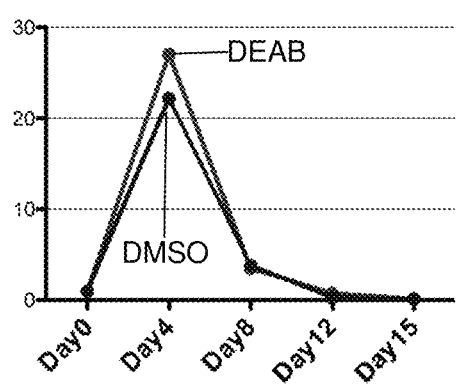
FIG. 6C shows expression of MIXL1.
Figure 6D:
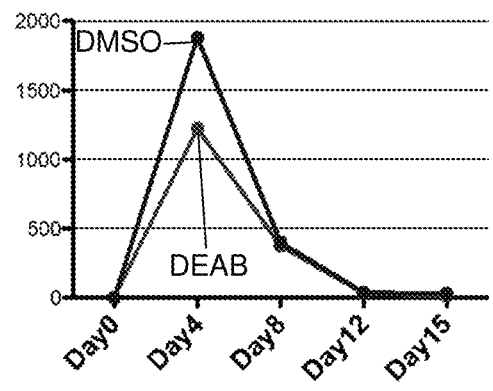
FIG. 6D shows expression of SOX17.

The expression analyses identified differential expression in genes ranging from early germ layer specification (PAX6, Brachyury, MIXL1, SOX17), mesodermal sub specifications (FOXF1, FOXC1, NKX2.5), hemogenic endothelial specifications (APLNR, PDGFRA (low), FLK1), and hematopoietic specifications (RUNX1). The first days of the differentiation involve the formation of embryoid bodies in a mesoderm biasing media (primarily due to BMP4), we saw that RA signaling inhibition by DEAB significantly increased overall expression of the mesoderm marker, Brachyury (FIG. 6B), slightly increased (20%) expression of the primitive streak mesoderm marker MIXL1 (FIG. 6C), significantly reduced expression of the endoderm specific marker SOX17 (FIG. 6D), and the early ectoderm and neuroectoderm marker PAX6 showed reduced expression at early time point with the inhibitor but this level later equalized (FIG. 6A). These results suggest that RA inhibition by DEAB during germ layer specification of differentiating pluripotent stem cells increased mesoderm lineage specification at the expense of endoderm, and had limited effect on ectodermal lineage.

Figure 6E:
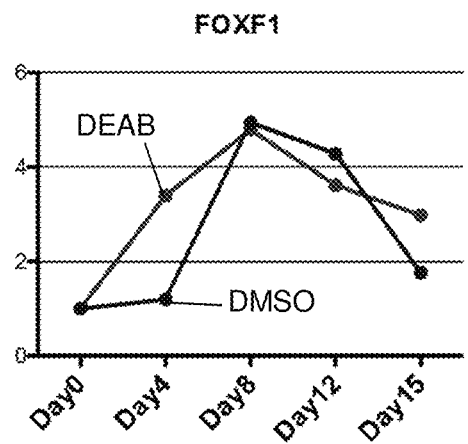
FIG. 6E shows expression of FOXF1.
Figure 6F:
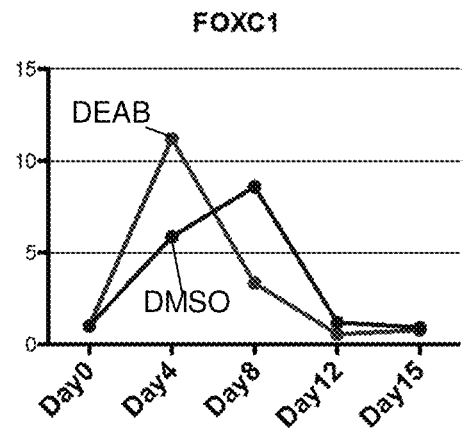
FIG. 6F shows expression of FOXC1.
Figure 6G:
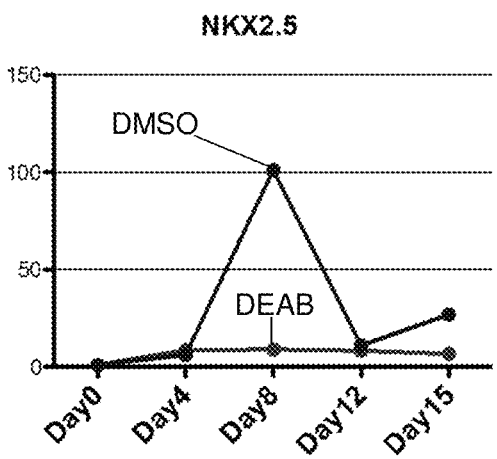
FIG. 6G shows expression of NKX2.5.

Within the mesoderm lineage we then quantified the expression of markers of the paraxial (FOXC1) and lateral plate (FOXF1, hematopoietic and cardiac precursor) mesoderm. As expected both these markers show elevated levels (FIGS. 6F and 6E, respectively) at early time points in comparison to the DMSO control, likely as a result of the increased mesodermal specification from the inhibitor earlier in the protocol. However the paraxial mesoderm marker levels FOXC1 became significantly reduced over time with the RA inhibitor DEAB compared to the DMSO control (FIG. 6F, Days 6-12), despite the initial increase in mesoderm specification, suggesting further specification of lateral plate mesoderm. The lateral plate mesoderm marker levels of FOXF1 in the DMSO control eventually increased to levels comparable to the RA inhibitor DEAB (FIG. 6E, Day 8 onward). This is likely the result of anterior lateral plate mesoderm formation (precursors of the heart). We saw a dramatic upregulation of the cardiogenic mesoderm marker NKX2.5 in the DMSO control at this time point (FIG. 6G, Day 12 onward). The reduced expression of the cardiogenic lateral plate mesoderm marker NKX2.5 using the RA inhibitor DEAB is in agreement with the significantly reduced numbers of beating cardiomyocytes colonies seen in our cultures using the RA inhibitor DEAB (data not shown).

Together these data suggest that using the RA inhibitor DEAB in our pluripotent stem cell differentiation system recapitulates the known embryonic developmental processes through mesoderm specification towards hemogenic endothelium.

Figure 6H:
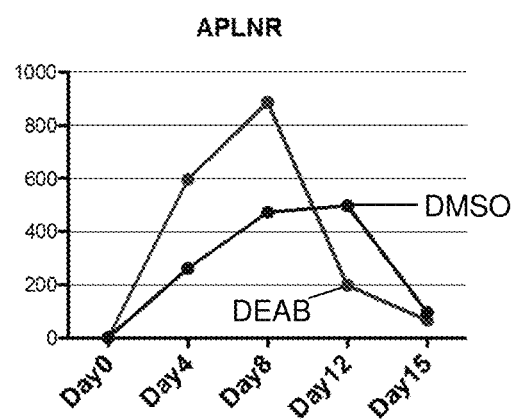
FIG. 6H shows expression of APLNR.
Figure 6I:
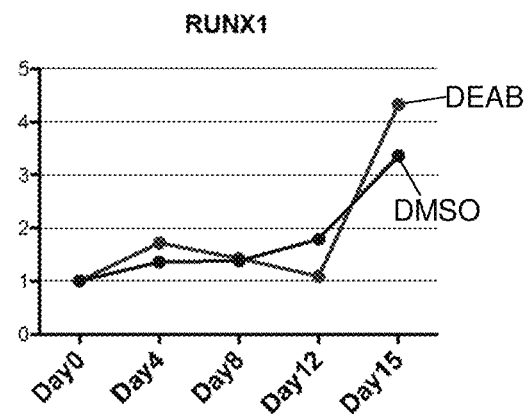
FIG. 6I shows expression of RUNX1.
Figure 6J:
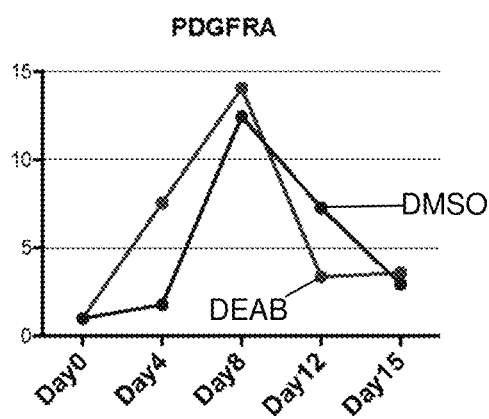
FIG. 6J shows expression of PDGFRA.
Figure 6K:
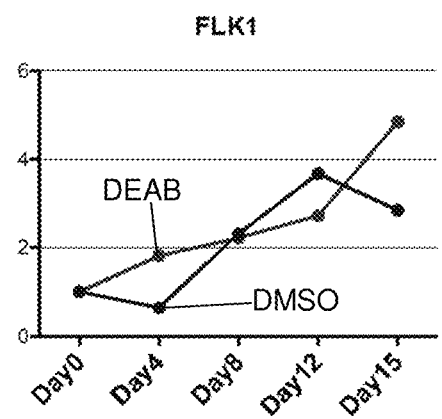
FIG. 6K shows expression of FLK1.

Because the markers of lateral plate mesoderm were elevated using the RA inhibitor DEAB, we then looked at two newly identified markers specifying mesodermal cells with hematopoietic potential, APLNR and PDGFRA. APLNR has been shown to be upregulated in mesodermal cells with definitive or primitive blood potential (Choi et al. Cell Rep. 2012, 2(3):553-67)). PDGFRA has been shown to be upregulated in mesodermal cells with mostly primitive blood potential and hemangioblast activity (Choi et al. Cell Rep. 2012, 2(3):553-67)). In definitive type hematopoietic precursors, namely hemogenic endothelium, APLNR is expressed highly, however PDGFRA is downregulated. APLNR and PDGFRA show this expression pattern at Day 12 in the DEAB suggesting definitive hematopoietic cell potential (FIGS. 6H and 6J, respectively). This was subsequently confirmed by the increased expression of RUNX1 (a definitive hematopoietic cell marker) (FIG. 6I) in the later stages of the differentiation (Day 12-15) compared to the DMSO control.

Interestingly, in the presence of the RA inhibitor DEAB, the marker gene FLK1 which is an endothelial cell marker but also a broad mesoderm marker (including of mesoderm with cardiac potential) (Ema et al., "Deletion of the selection cassette, but not cis-acting elements, in targeted Flk1-lacZ allele reveals Flk1 expression in multipotent mesodermal progenitors," Blood, 2006, 107:111-117), showed high levels at the early time point (Day 4), when primitive hematopoietic cell generation is possible, and showed similar expression compared to DMSO in the intermediate time point (Day 8), when mesoderm cells were committing to the cardiac mesoderm in the DMSO. At later time points (Days 12-15), however, FLK expression increased in the presence of DEAB, indicating an increase endothelial cell number that agrees with the increased blood potential seen by FACS and definitive hematopoietic cell output of RUNX1.

Figure 6L:
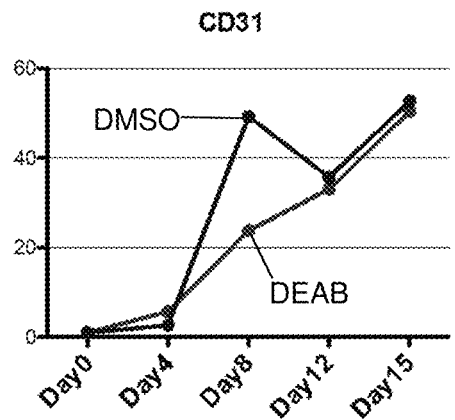
FIG. 6L, shows expression of CD31.

The marker gene CD31, which is expressed primarily on endothelial cells during development, was very highly expressed in the primitive wave early time point. However, following the primitive wave, its expression followed that of DEAB, suggesting that these primitive wave endothelial cells are maintained in the culture but are reduced with the RA inhibitor DEAB (FIG. 6L).

Figure 6M:
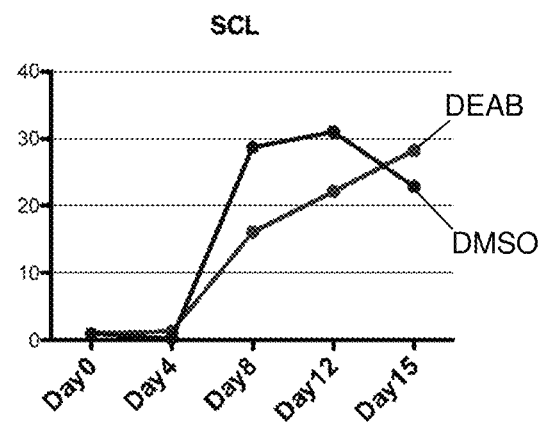
FIG. 6M shows expression of SCL.

SCL is a marker of both primitive and definitive hematopoiesis. Increased SCL expression with DMSO compared to DEAB in the early time points (FIG. 6M, Day 8-12) agrees with the above assessment of DMSO having more primitive wave hematopoiesis than DEAB at these time points. However, increased SCL expression was observed with DEAB compared to DMSO at later time points (FIG. 6M, Day 15), indicating definitive hematopoiesis with DEAB. See Zhang Y, Payne K J, Zhu Y, Price M A, Parrish Y K, Zielinska E, Barsky L W, Crooks G M, "SCL expression at critical points in human hematopoietic lineage commitment," Stem Cells. 2005 June-July; 23(6):852-60.

Based on these marker expression profiles in combination with the in vitro differentiation data (functional and FACS where we demonstrate significant numbers of cells with definitive hematopoietic phenotype (CD45+, CD43+), and generate lymphoid lineages, see at least Examples 1-3 above and Example 5 below), the data strongly suggest that definitive hematopoietic cells are the predominant hematopoietic cells generated in our system with the RA inhibitor DEAB.

Figure 6N:
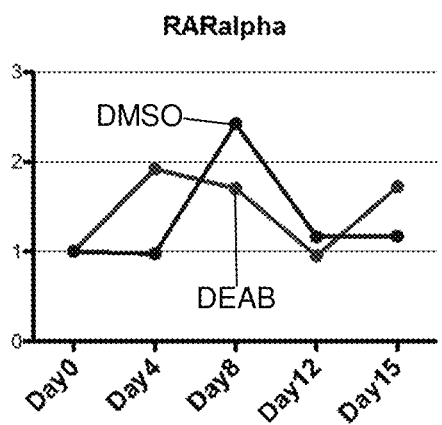
FIG. 6N shows expression of RARalpha.
Figure 6O:
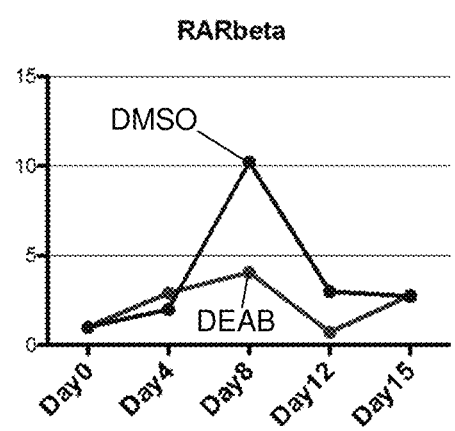
FIG. 6O shows expression of RARbeta.
Figure 6P:
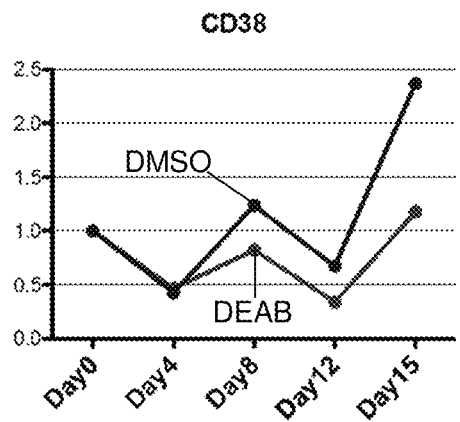

To confirm the RA signaling inhibition using DEAB, we measured the levels of expression of known gene targets of RA. We detected reduced levels of RARa (FIG. 6N, Day 8) and RARb (FIG. 6O, Day 8) expression, demonstrating inhibition of the feed forward regulation of RA signaling. Similarly, reduction of the known RA target, CD38, was also confirmed by PCR (FIG. 6P), confirming the reduced CD38 expression seen by FACS as described earlier.

Example 5

Differentiation into Lymphocytes

Figure 7F:
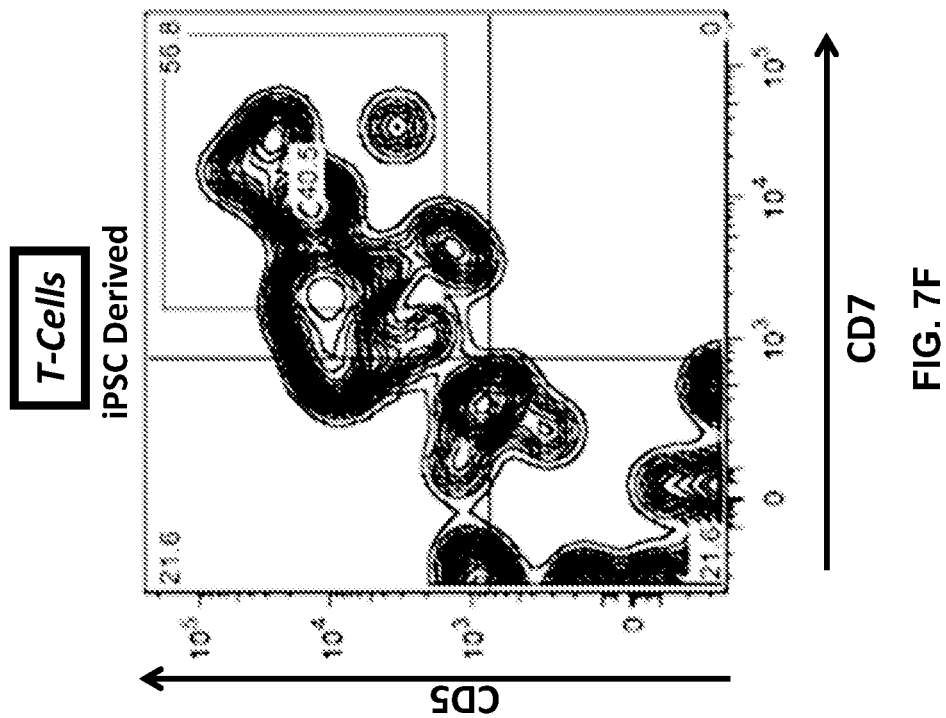
Figure 7E:
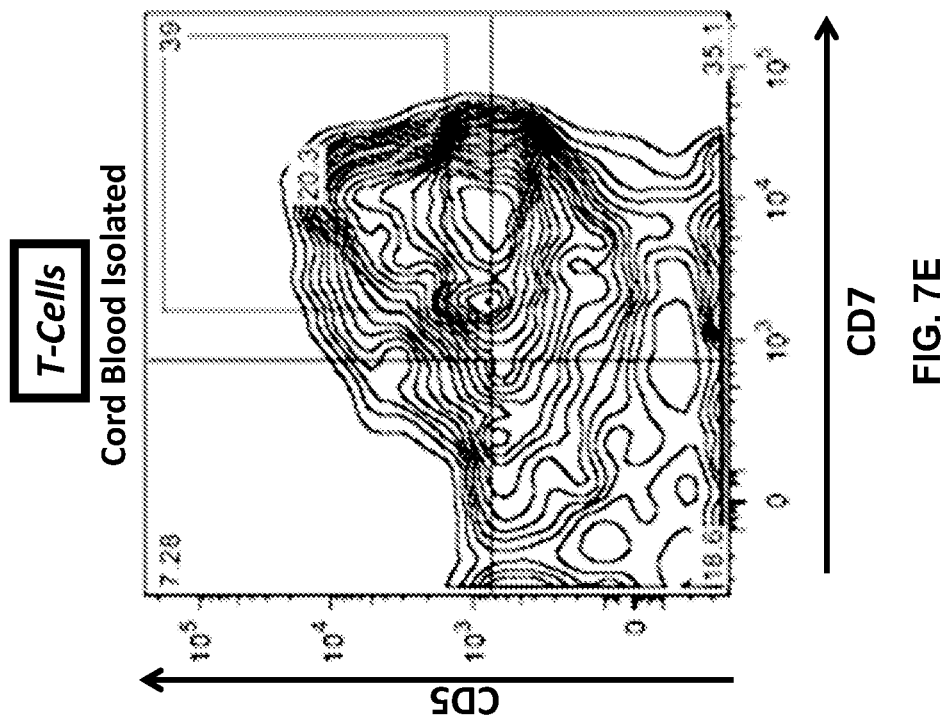
Figure 7H:
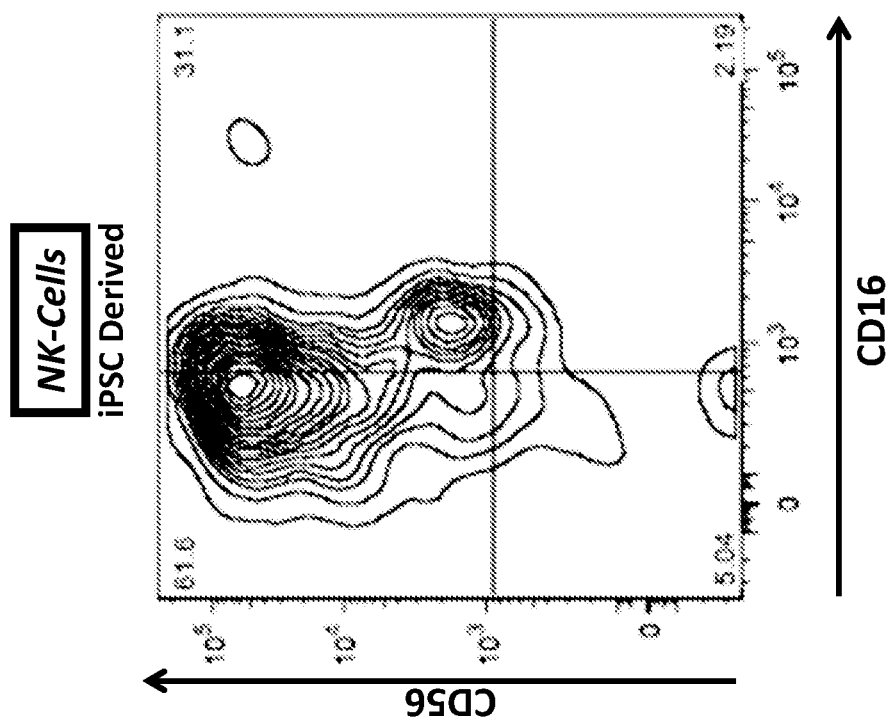
Figure 7G:
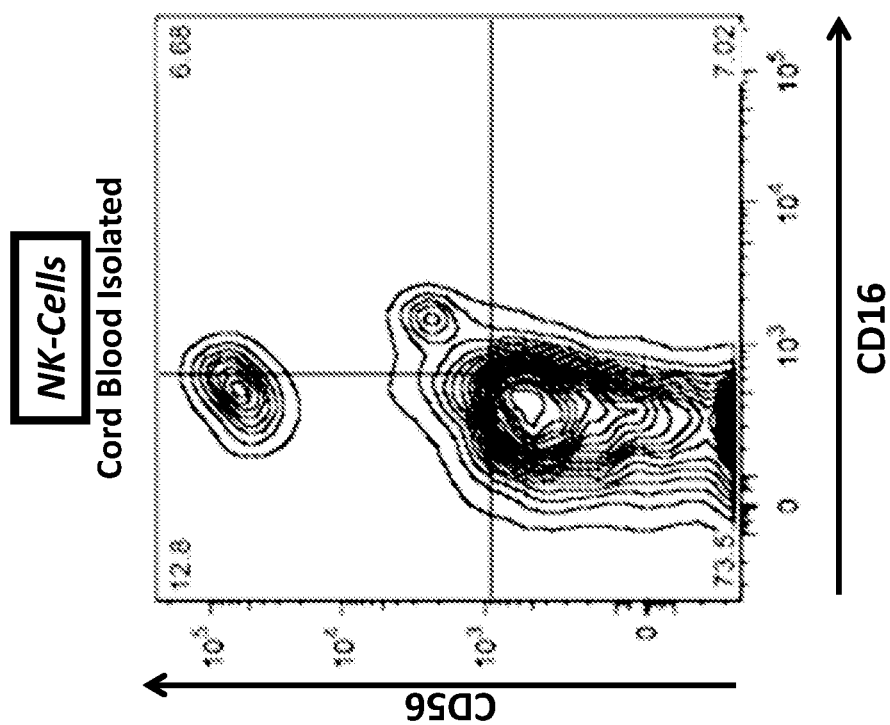
Figure 7J:
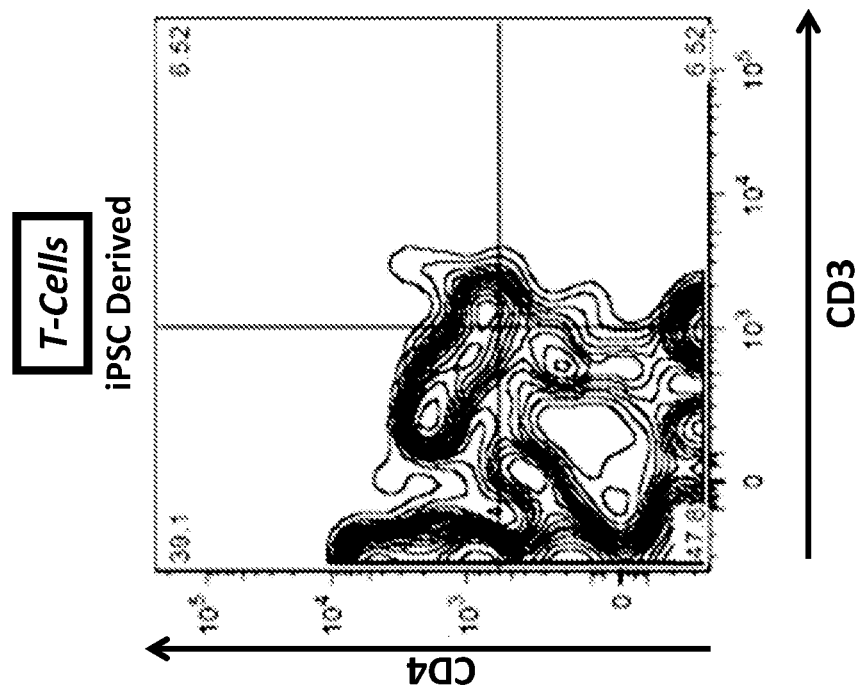
Figure 7I:
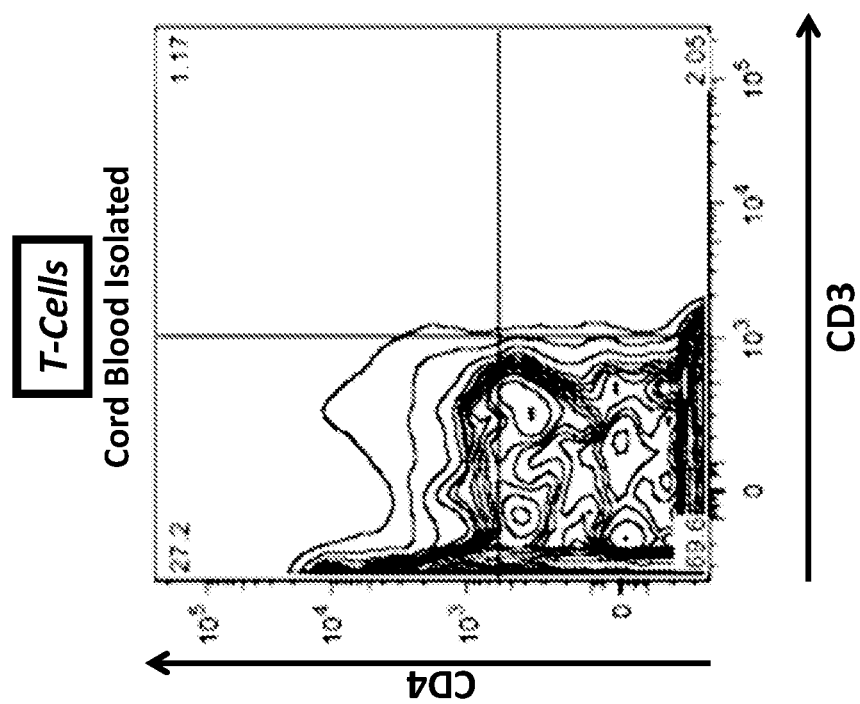

Hematopoietic progenitors and phenotypic stem cells obtained by differentiating iPS cells using the basal medium supplemented with DEAB at 10 uM were differentiated into lymphoid cells (B, NK, T) as described in Nozad Charoudeh H, Tang Y, Cheng M, Cilio C M, Jacobsen S E, Sitnicka E, "Identification of an NK/T cell-restricted progenitor in adult bone marrow contributing to bone marrow- and thymic-dependent NK cells.," Blood. 2010 Jul. 15; 116(2):183-92. Briefly, either CD45+, CD43+, CD34+, 7AAD-hematopoietic progenitors, or CD45+, CD43+, CD34+, CD38−, CD90+, CD45RA− phenotypic HSCs were plated side by side with cord blood isolated hematopoietic progenitors at 20-40 cells per well onto previously established, approximately 80% confluent stroma cell monolayers of OP9 and OP9delta feeder lines for B-cell and T-cell differentiation respectively in 48-well plates in 1 mL of Opti MEM plus GlutaMax (Life Technologies, Carlsbad Calif.) containing 10% fetal calf serum (FCS; Sigma-Aldrich), 1% penicillin/streptomycin (Sigma-Aldrich), 1% 2M 2-mercaptoethanol (Sigma-Aldrich) supplemented with cytokines with final concentrations: FLT3 ligand (FL, 25 ng/mL), interleukin-7 (IL-7, 20 ng/mL), KIT ligand (KL, 25 ng/mL), IL-15 (25 ng/mL), and IL-2 (50 ng/mL). Cells were cultured at 37° C. for 14 to 21 days, and half of the coculture medium was replaced weekly. Between 14 and 21 days after differentiation, cells were harvested and analyzed by FACS side by side with the cord blood isolated progenitors differentiated to B, NK, and T cells under the identical method as described above for pan-lymphoid lineage (CD33−, FIGS. 7A and 7B) and lymphoid committed progeny (B cell (CD19+, CD10+; FIGS. 7C and 7D), T cell (CD3+, CD4+; FIGS. 7I and 7J) (CD5+, CD7; FIGS. 7E and 7F), and NK cell (CD56+, CD16+; FIGS. 7G and 7H)). The results show that the HSCs generated as described above are capable of differentiating to each type of tested lymphocyte.

Example 6

LY2228820

We conducted experiments to determine whether the p38 inhibitor LY2228820 could further increase hematopoietic progenitor and phenotypic stem cell outputs by acting in concert with DEAB when added to Differentiation Medium 1. Human ES and iPS cells were differentiated to progenitors and phenotypic stem cells as described, except 100 nM of LY2228820 was added to Differentiation Medium 1. Cells were then harvested as described and subjected to flow cytometry and FACS analysis using fluorescently labeled antibodies for CD45, CD43, CD34, CD38, CD90, CD45RA as described. Results show that the phenotypic hematopoietic stem cell phenotype (CD45+, CD43+, CD34+, CD38−, CD90+, CD45RA−) was increased by nearly 20% over the DEAB-containing Differentiation Medium 1 control, whereas levels of the intermittent progenitor phenotype (CD45+, CD43+, CD34+, CD38−) were unaffected (FIG. 8A). Conversely for iPS cells, the addition of 100 nM of LY2228820 increased numbers of all cells with the progenitor and phenotypic stem cell phenotypes (FIG. 8B). These results suggest that progenitor and/or phenotypic stem cell yields can be further increased when using LY2228820 in concert with DEAB in our differentiation medium and protocol.

Example 7

Norepinephrine

We conducted experiments to reveal if human embryo AGM region-harvested cells generate neurospheres in culture to confirm the presence of neural crest cells in the AGM region. We further completed some experiments to identify a component secreted from the neural crest cells that may be involved in definitive hematopoiesis. We harvested human embryo AGM region tissue and, using fluorescent labeled antibodies specific for neural crest cells, were able to identify the presence of neural crest cells in the AGM hematopoietic niche. This suggested that neural crest cells play a role in hematopoiesis. Hypothesizing norepinephrine as a potential effector secreted from the neural crest cells, we tested it for its ability to further increase progenitor and phenotypic stem cell yields when added to Differentiation Medium 1 at a concentration of 10 uM or 300 uM. Human ES and iPS cells were differentiated to progenitors and phenotypic stem cells with Differentiation Medium 1 as described. The only difference is that 10 uM or 300 uM of norepinephrine was added to Differentiation Medium 1. Cells were then harvested as described and subjected to flow cytometry and FACS analysis using fluorescently labeled antibodies for CD45, CD43, CD34, CD38, CD90, CD45RA as described. The results of this experiment reveal statistically significant increases in fold improvement of numbers of phenotypic hematopoietic stem cells (CD45+, CD34+, CD43+, CD38−, CD90+, CD45RA−, FIG. 9C) whereas insignificant improvements were observed in the total viable blood cells (CD45+, FIG. 9A) and the intermediate cells (CD45+, CD43+, CD34+, CD38−, FIG. 9B). The results demonstrate that norepinephrine has an effect on the most primitive fraction of hES-derived hematopoietic cells (150% increase in HSC number) and on colony forming ability (data not shown). These data suggest that norepinephrine is an effector secreted from neural crest cells. Given the verified presence of neural crest cells in the AGM niche, we are confident that these cells play a role in establishing definitive hematopoiesis in the developing embryo. As such, long term engraftment and reconstitution ability of hematopoietic progenitors and phenotypic stem cells produced from iPS and ES cells differentiated with Differentiation Medium 1 plus norepinephrine as described above are currently underway. The engraftment and reconstitution studies will be conducted as described by the protocol outlined above in the Materials and Methods.

Example 8

Additional Molecules

Figure 14:
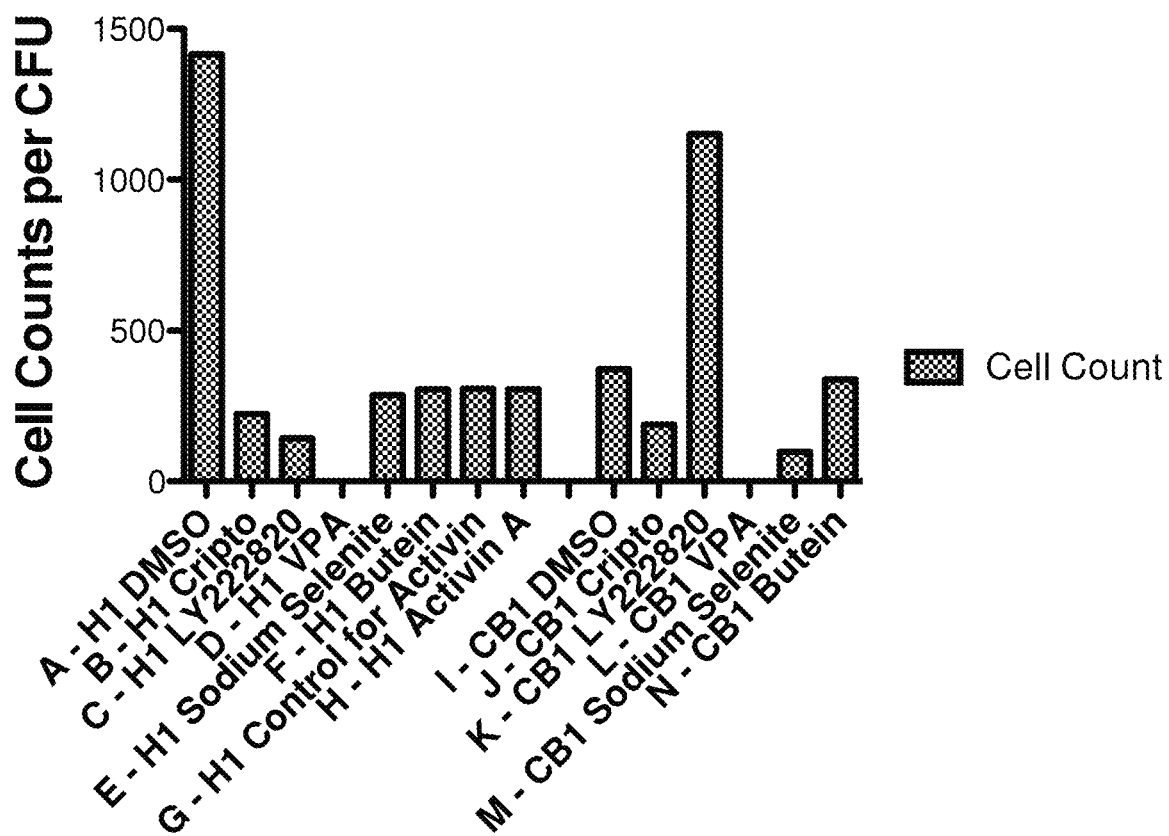
FIG. 14 depicts myeloid CFU cell count data for cells differentiated from pluripotent stem cells (H1 ES cells and CB1 iPS cells) in the presence of DEAB and each of Cripto (500 ng/ml), LY2228820 (shown as "LY222820", 100 nM), Activin A, valproic acid (VPA, 1 mM), sodium selenite (100 nM), and butein (10 µM).

We have completed a number of studies to establish other molecules that may further improve the yields and phenotypes of hematopoietic cells derived using Differentiation Medium 1. Tested compounds were Cripto, LY2228820, valproic acid (VPA), sodium selenite, and butein. Data for these are defined below. In all instances, each molecule below was supplemented into Differentiation Medium 1 to study their effect in concert with DEAB. All control experiments for these molecules were cells differentiated using Differentiation Medium 1 (which already contains DEAB). The data we report below for these molecules illustrates how they may improve the yield of hematopoietic progenitors and phenotypic stem cells measured by FACS, flow cytometry, and CFU assays. It is important to note when interpreting these results that the definitive hematopoietic stem cells in vivo do exist in a quiescent, non-proliferative state during part of their life cycle. As such, molecules that do not dramatically improve CFU counts of these cells may still contribute to improving HSC quiescence, thought to be necessary for high levels of engraftment. The in vivo engraftment studies to confirm this for these molecules are underway. See FIG. 14 for the CFU data. This data taken in context with FIGS. 10A, 10B, 11A, 11B, 12A, 12B, 13A, and 13B showing increased fraction of phenotypic HSCs suggest that cells produced with Differentiation Medium 1 supplemented with these compounds reduces stress and increases production of quiescent HSCs.

As shown in FIGS. 10A and 10B, LG101506 (1 uM) when used in the Differentiation Medium 1 medium increased the total number of cells (similar to the DEAB results) for both pluripotent lines (ES, iPS), indicating that this also increases the total output of CD90+ cells. Interestingly, the combination of DEAB with LG101506 further increased the numbers of CD38− cells compared to either compound alone, and generates the highest numbers of phenotypic HSCs.

It has been shown that DS DNA breaks reduce transplant efficiency of repopulating HSCs. In vitro derived blood from pluripotent stem cell has high levels of DNA damage. Inhibition of DNA damage and the DNA damage response, from reactive oxygen species (ROS) or other sources of damage (radiation, chemical etc) in pluripotent stem cell differentiation systems will decrease DNA damage and increase hematopoietic cell number, repopulating ability and increase the differentiation potential of the cells (i.e. expansion of downstream lineages). See Yahata et al. *Blood,* 2011, 118(11):2941-50). We show that simple culture differentiation of pluripotent cells results in many double strand (DS) DNA breaks as marked by gH2AX staining. Adding sodium selenite (100 nM) and butein (10 uM) independently to Differentiation Medium 1 increased enzyme activity for protection against reactive oxygen species (ROS). Each of sodium selenite (100 nM) and butein (10 uM) independently added to Differentiation Medium 1 also increased CD34+, CD38− cells as well as total cells. See FIGS. 11A and 11B for sodium selenite and FIGS. 12A and 12B for butein. These studies are being expanded into dose response experiments from which we expect to identify optimal concentrations.

From the pluripotent stem cells differentiated with Differentiation Medium 1 supplemented with 1 mM of valproic acid, we see that all CD34+CD38− cells were 100% CD90+. The total number of cells was also increased. See FIGS. 13A and 13B. These results are being expanded further into a dose response study from which we expect to identify the optimal concentration. Engraftment studies as described are also being conducted.

Example 9

Pluripotent Stem Cell Derived Hematopoietic Cell Transplantation

We have confirmed short-term engraftment and reconstitution ability of hPSC-derived HSCs produced as described in Example 1, by injecting them into sublethally irradiated (325 rad) NOD.Cg-Prkdc$^{scid}$Il2rg$^{tm1Wjl}$/SzJ mice (JAX, Bar Harbor, Me., www.jax.org) via tail vein injections, intrafemoral injection, or cardiac injection. We transplanted NOD.Cg-Prkdc$^{scid}$Il2rg$^{tm1Wjl}$/SzJ mice with 3×10$^6$ unsorted cells or 5000 FACS sorted phenotypic HSCs (CD45+, CD43+, CD34+, CD38−, CD90+, CD45RA−) from differentiations using Differentiation Medium 1 medium not including with DEAB (Control) and Differentiation Medium 1 medium including DEAB (DEAB HSCs). We analyzed the red blood cell-lysed, mononuclear fraction of peripheral blood samples collected 4 weeks post-transplant for the percentage of cells exhibiting the pan-hematopoietic human blood cell marker CD45+ by FACS or flow cytometry. Typical published values range from 0.1%-1.0%, including those obtained from our control where DEAB was not used to generate the HSCs (0.34%±0.1%). (See Wang et al. *The Journal of Experimental Medicine,* 2005, 201(10):1603-14; Lu et al. *Experimental hematology,* 2009, 37(8): 924-36; Tian et al. *Stem cells,* 2009, 27(11): 2675-85; Ledran et al. *Cell stem cell,* 2008, 3(1):85-98; Bhatia, M., Hematopoietic development from human embryonic stem cells. Hematology/the Education Program of the American Society of Hematology. American Society of Hematology. Education Program, 2007: p. 11-6; and Bhatia, M. *Annals of the New York Academy of Sciences,* 2007, 1106:219-22.) We demonstrated 2-fold higher engraftment (2.2%±0.2%, n=4), suggesting that HSCs differentiated from pluripotent stem cells using Differentiation Medium 1 medium containing DEAB significantly improves engraftment outcome upon transplantation and is ideal for testing and incorporating additional factors to improve hPSC-derived HSC engraftment and reconstitution to levels required for therapeutics.

Further engraftment studies are underway with the HSC cells generated as described above. We predict that phenotypic HSC cells produced with Differentiation Medium 1 (containing DEAB) supplemented with any of one or more of Cripto, LY222820, valproic acid (VPA), sodium selenite, butein, norepinephrine, and LG101506 will generate cells suitable for successful in vivo engraftment.

We claim:
1. A differentiation medium comprising:
a retinoic acid signaling inhibitor comprising DEAB;
an antioxidant comprising ascorbic acid;
a stimulant of prostaglandin $E_2$ pathway comprising prostaglandin $E_2$ (PGE2);
a P38 MAPK inhibitor comprising LY2228820;
BMP4;
vascular endothelial growth factor (VEGF); and
a beta adrenergic receptor agonist comprising norepinephrine.
2. The differentiation medium of claim 1 wherein:
the DEAB is present in an amount of from about 0.3 µM to about 300 µM;
the PGE2 is present in an amount of from about 0.6 µM to about 60 µM;
the LY2228820 is present in an amount of from about 3 nM to about 3 µM;
the BMP4 is present in an amount of from about 0.3 ng/ml to about 300 ng/mL;
the VEGF is present in an amount of from about 0.01 ng/mL to about 30 ng/mL; and
the norepinephrine is present in an amount of from about 10 µM to about 10 mM.
3. The differentiation medium of claim 1, further comprising thrombopoietin (TPO), stem cell factor (SCF), fms-related tyrosine kinase 3 (FLT3), erythropoietin (EPO), and transforming growth factor beta (TGFβ1).
4. The differentiation medium of claim 3 wherein:
the TPO is present in an amount of from about 0.6 ng/mL to about 600 ng/mL;
the SCF is present in an amount of from about 0.6 ng/mL to about 600 ng/mL;
the FLT3 is present in an amount of from about 0.6 ng/mL to about 600 ng/mL;
the EPO is present in an amount of from about 0.6 ng/mL to about 600 ng/mL; and
the TGFβ1 is present in an amount of from about 0.15 ng/mL to about 150 ng/mL.
5. The differentiation medium of claim 3 wherein:
the DEAB is present in an amount of from about 0.3 µM to about 300 µM;
the PGE2 is present in an amount of from about 0.6 µM to about 60 µM;
the LY2228820 is present in an amount of from about 3 nM to about 3 µM;
the BMP4 is present in an amount of from about 0.3 ng/ml to about 300 ng/mL;
the VEGF is present in an amount of from about 0.01 ng/mL to about 30 ng/mL; and
the norepinephrine is present in an amount of from about 10 µM to about 10 mM the TPO is present in an amount of from about 0.6 ng/mL to about 600 ng/mL;

the SCF is present in an amount of from about 0.6 ng/mL to about 600 ng/mL;

the FLT3 is present in an amount of from about 0.6 ng/mL to about 600 ng/mL;

the EPO is present in an amount of from about 0.6 ng/mL to about 600 ng/mL; and the TGFβ1 is present in an amount of from about 0.15 ng/mL to about 150 ng/mL.

6. A method of differentiation comprising contacting a cell with the differentiation medium of claim 1.

7. The method of claim 6 wherein the cell comprises a pluripotent stem cell and wherein the contacting comprises contacting for a time and under conditions sufficient to generate a hematopoietic stem cell.

8. The method of claim 7 wherein the hematopoietic stem cell is capable of further differentiating into a myeloid cell and is also capable of further differentiating into a lymphoid cell.

9. The method of claim 7 further comprising differentiating the hematopoietic stem cell into a cell selected from the group consisting of a myeloid cell and a lymphoid cell.

10. The method of claim 9 wherein the differentiating the hematopoietic stem cell is performed in vitro.

11. The method of claim 9 wherein the differentiating the hematopoietic stem cell is performed in vivo.

12. The method of claim 6 wherein the cell is a human cell.

13. The method of claim 6 wherein the contacting comprises initially contacting the cell with the differentiation medium by adding a volume of the differentiation medium to an existing volume of non-differentiation medium to generate a mixed medium, contacting the cell with the mixed medium, and subsequently replacing substantially all the mixed medium after about 12-48 hours from the initial contacting with a fresh volume of the differentiation medium.

14. The method of claim 13 wherein after the replacing substantially all the mixed medium the contacting further comprises adding a fresh volume of the differentiation medium only to an existing volume of the differentiation medium, wherein the existing volume comprises medium contacting the cell for a period of at least two hours.

15. The method of claim 6 wherein the cell comprises an intact embryoid body formed for a period of at least 7 days prior to the contacting.

16. The method of claim 15 wherein the contacting comprises contacting the intact embryoid body with the differentiation medium for a period of at least 5 days prior to plating the embryoid body, and then plating the embryoid body.

17. The method of claim 16 wherein the contacting, after the plating, further comprises adding a fresh volume of the differentiation medium only to an existing volume of the differentiation medium without removing any of the existing volume of the differentiation medium, wherein the existing volume comprises medium contacting the cell for a period of at least 15 minutes.

18. The method of claim 6 wherein the contacting comprises contacting the cell with the differentiation medium in the absence of feeder cells.

19. A method of engrafting a blood cell in a human subject comprising administering a hematopoietic stem cell or a cell differentiated therefrom to the subject, wherein the hematopoietic stem cell is generated by contacting a cell with the differentiation medium of claim 1.

* * * * *